United States Patent
Ito et al.

(10) Patent No.: US 7,887,920 B2
(45) Date of Patent: Feb. 15, 2011

(54) BORATE AND NEAR-INFRARED RAY ABSORPTION MATERIAL

(75) Inventors: Akio Ito, Toyonaka (JP); Satoshi Ishida, Kyoto (JP); Toshiya Iida, Sakai (JP); Takako Ishii, Osaka (JP); Nobuhiro Kobayashi, Toyonaka (JP)

(73) Assignee: Nippon Shokubai Co., Ltd., Osaka (JP)

( * ) Notice: Subject to any disclaimer, the term of this patent is extended or adjusted under 35 U.S.C. 154(b) by 383 days.

(21) Appl. No.: 11/795,320

(22) PCT Filed: Jan. 30, 2006

(86) PCT No.: PCT/JP2006/301914
§ 371 (c)(1),
(2), (4) Date: Jul. 16, 2007

(87) PCT Pub. No.: WO2006/082945
PCT Pub. Date: Aug. 10, 2006

(65) Prior Publication Data
US 2008/0102279 A1     May 1, 2008

(30) Foreign Application Priority Data

Feb. 4, 2005 (JP) ............... 2005-029504
May 10, 2005 (JP) ............... 2005-137530
May 10, 2005 (JP) ............... 2005-137561

(51) Int. Cl.
*B32B 33/00* (2006.01)
*G02B 5/22* (2006.01)
*C08K 5/55* (2006.01)
*C07F 5/02* (2006.01)

(52) U.S. Cl. ............... 428/409; 428/913; 428/432; 524/183; 252/587; 568/1; 568/16; 564/8

(58) Field of Classification Search .................. None
See application file for complete search history.

(56) References Cited

U.S. PATENT DOCUMENTS

| | | | |
|---|---|---|---|
| 5,362,592 A | 11/1994 | Murofushi et al. | |
| 5,567,778 A | 10/1996 | Sakagami et al. | |
| 5,607,803 A | 3/1997 | Murofushi et al. | |
| 5,989,772 A * | 11/1999 | Tutt et al. ............... | 430/201 |
| 6,110,987 A | 8/2000 | Kamata et al. | |
| 6,255,031 B1 | 7/2001 | Yao et al. | |
| 6,522,463 B1 | 2/2003 | Shimomura et al. | |
| 7,193,779 B2 | 3/2007 | Kim et al. | |
| 2004/0137367 A1 | 7/2004 | Kitayama et al. | |
| 2006/0199105 A1* | 9/2006 | Cahill ............... | 430/270.11 |

FOREIGN PATENT DOCUMENTS

| | | |
|---|---|---|
| EP | 0 841 189 A1 | 5/1998 |
| JP | 10-142722 A | 5/1998 |
| JP | 2001-296652 A | 10/2001 |
| JP | 2003-096040 A | 4/2003 |
| JP | 2004-246365 A | 9/2004 |
| JP | 2004-263084 A | 9/2004 |
| JP | 2004-264416 A | 9/2004 |
| WO | WO 2005/005140 A1 | 1/2005 |
| WO | WO 2006/096476 A2 | 9/2006 |

OTHER PUBLICATIONS

Translation of JP-10142722.*
European Office Action dated Dec. 17, 2007.
Database CA, Database Accession No. 129:88060 (of JP 10-142722), May 29, 1998, XP-002396545.
European Office Action dated Apr. 9, 2009.
Chinese Office Action dated Jul. 17, 2009, and issued in Application No. 2006800030602, and English translation thereof.
Korean Office Action dated dated Jun. 22, 2009, and issued in Application No. 10-2007-7017497, and English translation thereof.
Form PCT/ISA/210 (International Search Report) dated Sep. 19, 2006.
Form PCT/ISA/237 (Written Opinion of the International Searching Authority) Sep. 19, 2006.
Chinese Office Action dated Apr. 13, 2010, and issued in Application No. 200680003060.2, and English translation thereof.
Korean Office Action dated Apr. 13, 2010, and issued in Application No. 10-2007-7017497, and English translation thereof.
Korean Office Action dated Oct. 11, 2010, and issued in corresponding Korean Application No. 10-2007-7017497, and English translation thereof.

* cited by examiner

*Primary Examiner* — Ling Xu
(74) *Attorney, Agent, or Firm* — Buchanan Ingersoll & Rooney PC

(57) ABSTRACT

A borate for a near-infrared ray absorption material, having an anion represented by the formula (1): $[BR^1_m R^2_{4-m}]^-$ (wherein $R^1$ represents an aryl group having an electron withdrawing group; $R^2$ represents an organic group, a halogen group or a hydroxyl group; and m is an integer in the range of 1 to 4) is provided. The borate of the present invention enables to improve durability, in particular, heat resistance and moisture resistance of a near-infrared ray absorbing dye.

16 Claims, 15 Drawing Sheets

BORATE AND NEAR-INFRARED RAY ABSORPTION MATERIAL

TECHNICAL FIELD

The present invention relates to a borate for a near-infrared ray absorption material, a near-infrared ray absorption material containing the borate, and a filter for a plasma display and an optical semiconductor element using the near-infrared ray absorption material. In particular, the present invention relates to a borate having improved durability of a near-infrared ray absorbing dye, a near-infrared ray absorption material containing the borate superior in transparency in visible region and durability, and a filter for a plasma display and an optical semiconductor element using the near-infrared ray absorption material.

BACKGROUND ART

Recently, PDP (Plasma Display Panel) applicable to a thin and large area screen has been noticed. PDP generates near-infrared ray of a wavelength of 800 nm to 1000 nm on plasma discharge, and it has been a problem that this near-infrared ray induces improper operation of a remote controller of home electric appliances. In addition, because an optical semiconductor element used in a CCD camera, and the like has a high sensitivity in near-infrared region, the removal of near-infrared ray is required. Under such circumstance, near-infrared ray absorption material having high near-infrared ray absorption ability and high transparency in visible region has been required.

As near-infrared ray absorption material, material added with a dye capable of absorbing near-infrared ray has widely been known. As such a near-infrared ray absorbing dye, a cyanine based dye, polymethine based dye, squarylium based dye, porphyrin based dye, a dithiol metal complex based dye, phthalocyanine based dye, a diimmonium based dye, and the like have conventionally been used. Among these, a diimmonium based dye has been widely used due to its high near-infrared ray absorption ability at a wavelength of not shorter than 900 nm and high transparency in visible light region (for example, see U.S. Pat. No. 6,255,031 and U.S. Pat. No. 6,522,463). As near-infrared ray absorption material for an optical semiconductor element, one containing a copper phosphate-based compound has been also used (for example, see U.S. Pat. No. 5,567,778).

Furthermore, because PDP generates discharge in gas atmosphere mainly composed of rare gas, in particular neon, encapsulated inside a panel, and by means of vacuum ultraviolet ray generated on the discharge, fluorescent substances, R, G and B installed in a cell inside the panel are made to emit luminescence. In this emission process, electromagnetic wave unnecessary to PDP operation is also discharged simultaneously, and therefore, shielding of electromagnetic wave is also required. In addition, to suppress reflection light, an antireflection film and a glare prevention film (an antiglare film) are also necessary. Therefore, an optical filter for a plasma display is generally prepared by laminating a near-infrared ray absorption film, an electromagnetic interference shielding film and an antireflection film on glass or an impact absorption sheet as a supporting substrate. Such an optical filter for a plasma display may be used by mounting at the front surface side of PDP or by directly adhering using an adhesive or a pressure-sensitive adhesive.

DISCLOSURE OF INVENTION

However, a near-infrared ray absorbing dye representing a diimmonium-based dye may sometimes be poor in durability, and deterioration of near-infrared ray absorption ability or coloring can incur a serious problem in display or optical semiconductor element applications. This deterioration is considered to be brought about by degeneration of a dye, caused by various factors such as heat, moisture and light. Therefore, various improvements of durability of a near-infrared ray absorbing dye have conventionally been challenged, however, the effects are not yet sufficient. In addition, because increase in content of a copper phosphate-based compound in near-infrared ray absorption material is difficult, it is difficult to obtain a thin film material superior in near-infrared ray absorption ability.

An object of the present invention, therefore, is to provide a borate which can advantageously be used in near-infrared ray absorption material (dye) to improve durability, in particular, heat resistance and moisture resistance of a near-infrared ray absorbing dye.

Another object of the present invention is to provide a near-infrared ray absorption material superior in transparency in visible region and durability.

Further another object of the present invention is to provide an optical filter for a plasma display, a filter for an optical semiconductor element, a plasma display and an optical semiconductor element using the near-infrared ray absorption material.

The present inventors have intensively studied a way to improve durability of a near-infrared ray absorbing dye, in particular, near-infrared ray absorption material used in an optical filter, to find that a borate having an aryl group having an electron withdrawing group bound to a boron atom enables to improve durability, in particular, heat resistance and moisture resistance of a near-infrared ray absorbing dye, and that a near-infrared ray absorption material added with such a borate is superior in transparency in visible region and durability (in particular, heat resistance and moisture resistance). In addition, the present inventors have found that by using this near-infrared ray absorption material, an optical filter for a plasma display and an optical filter for an optical semiconductor element superior in durability and transparency in visible region can be obtained. Based on the findings, the present invention has been completed.

Namely, the object can be attained by a borate for a near-infrared ray absorption material, having an anion represented by the following formula (1):

$$[BR^1{}_m R^2{}_{4-m}]^- \tag{1}$$

wherein $R^1$ represents an aryl group having an electron withdrawing group; $R^2$ represents an organic group, a halogen group or a hydroxyl group; and m is an integer in the range of 1 to 4.

In addition, the another object can be attained by a near-infrared ray absorption material containing the borate of the present invention and a near-infrared ray absorbing dye.

The further another object can be attained by an optical filter for a plasma display and a filter for an optical semiconductor element using the near-infrared ray absorption material of the present invention, along with a plasma display and an optical semiconductor element using these filters.

Since a borate of the present invention improves durability, in particular, heat resistance and moisture resistance of a near-infrared ray absorbing dye and further, does not impair transparency in visible region, it can advantageously be used in various near-infrared ray absorption materials (dyes) including a diimmonium-based dye which conventionally had a problem in durability.

In addition, by applying an optical filter using a near-infrared ray absorption material containing the borate of the present invention, to a plasma display or an optical semiconductor element, due to maintaining near-infrared ray absorption ability and transparency in visible region for a long time, appearance of a display or an optical semiconductor element can be improved.

The above and other objects, embodiments and other advantages of the present invention will be clear by explanation of the following preferable embodiments and drawings attached.

BEST MODE FOR CARRYING OUT THE INVENTION

Figure 1:
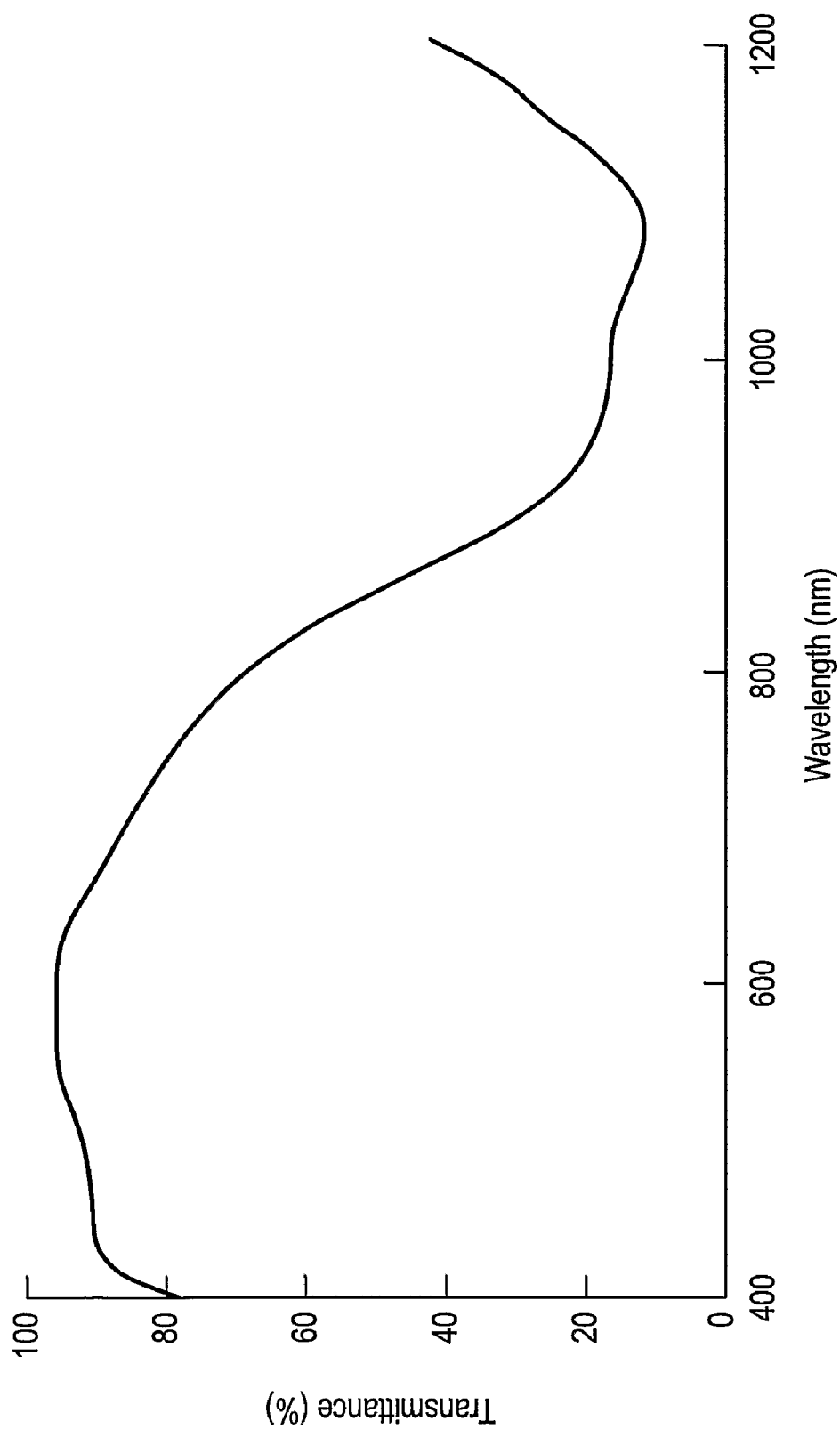
FIG. 1 is a visible-near-infrared absorbing spectrum of a diimmonium TEPB salt obtained in Example 3-1.

The present invention will be explained in detail below.

The first aspect of the present invention relates to a borate for a near-infrared ray absorption material, having an anion represented by the following formula (1):

$$[BR^1_m R^2_{4-m}]^- \quad (1)$$

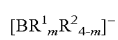

wherein $R^1$ represents an aryl group having an electron withdrawing group; $R^2$ represents an organic group, a halogen group or a hydroxyl group; and m is an integer in the range of 1 to 4.

(1) Anion of the Formula (1)

An anion used in the present invention is a borate anion represented by the formula (1), and by bonding an aryl group having an electron withdrawing group to a boron atom, durability of a near-infrared ray absorbing dye can be improved.

$R^1$ in the formula (1) represents an aryl group having an electron withdrawing group, and is not especially limited. It is preferably an aryl group of carbon atoms having 6 to 12 having an electron withdrawing group bound thereto, and includes, for example, phenyl group, naphthyl group and biphenyl group having an electron withdrawing group bound thereto. Among the aryl groups cited above, a phenyl group having an electron withdrawing group bound thereto (that is, $R^1$ is a phenyl group having an electron withdrawing group bound thereto) is economically preferable.

Although the electron withdrawing group in the $R^1$ in the formula (1) is not especially limited, it is specifically preferable to be at least one substituent selected from the group consisting of $-C_pF_{2p+1}$ (p is a natural number), $-NO_2$, $-CN$, $-F$, $-Cl$ and $-Br$, and it is more preferable to be at least one substituent selected from the group consisting of $-CF_3$, $-C_2F_5$ and $-F$, and it is particularly preferable to be $-F$. When a plurality of electron withdrawing groups are contained in an aryl group, each electron withdrawing group may be the same or different. In the present invention, in particular, the use of $-F$ enables to improve heat resistance and moisture resistance. Accordingly, $R^1$ in the formula (1) is preferably a pentafluorophenyl group ($-C_6F_5$), $-C_6HF_4$, $-C_6H_2F_3$, $-C_6H_3F_2$, $-C_6H_4F$, $-C_6F_4CF_3$, $-C_6F_3(CF_3)_2$, $-C_6F_2(CF_3)_3$, $-C_6F(CF_3)_4$, $-C_6(CF_3)_5$, and the like, and a pentafluorophenyl group is particularly preferable.

In the present invention, by the addition of a borate anion having an aryl group having an electron withdrawing group introduced thereto, heat resistance and moisture resistance of a near-infrared ray absorbing dye can be improved.

The substituent represented by $R^2$ in the formula (1) is not particularly limited so long as it is an organic group, a halogen atom or a hydroxyl group, and the organic group may have an electron withdrawing group. The organic group includes, for example, an aryl group having carbon atoms of 1 to 12 (for example, phenyl group, naphthyl group and biphenyl group) and an alkyl group having carbon atoms of 1 to 12, which may have a substituent, and the like, but is not especially limited thereto. Specifically, a linear, branched or alicyclic alkyl group such as methyl group, ethyl group, n-propyl group, isopropyl group, n-butyl group, isobutyl group, sec-butyl group, tert-butyl group, n-pentyl group, 1-methylbutyl group, 1-ethylpropyl group, 1,2-dimethylpropyl group, 1,1-dimethylpropyl group, neopentyl group, n-hexyl group and cyclohexyl group may be cited. Particularly, when the organic group is an alkyl group, it preferably has an electron withdrawing group, and it is more preferable that all of or a part of hydrogen atoms therein are substituted with a fluorine atom. Specifically, trifluoromethyl group, 2,2,2-trifluoroethyl group, 3,3,3-trifluoropropyl group, 4,4,4-trifluorobutyl group, perfluoroethyl group, perfluoropropyl group, perfluorobutyl group, and the like may be cited. A halogen atom specifically includes, for example, $-F$, $-Cl$, $-Br$ and $-I$, and $-F$ is more preferable.

In the present invention, m in the formula (1) is not especially limited so long as it is 1 to 4, however, it is preferably 4, namely, one having a structure represented by $[B(R^1)_4]^-$.

When m is not smaller than 2 in the present invention, a plurality of $R^1$'s may be included in a borate anion, and in this case, each of multiple $R^1$'s may be the same or different.

As a borate anion represented by the formula (1), for example, $[B(C_6F_5)_4]^-$ (tetrakis(pentafluorophenyl) borate), $[B(C_6F_4CF_3)_4]^-$, $[B(C_6F_5)_3(C_6H_5)]^-$, $[B(C_6F_5)_2(C_6H_5)_2]^-$, $[B(C_6F_5)(C_6H_5)_3]$, $[B(C_6F_5)_3F]^-$, $[B(C_6F_5)_2F_2]^-$, $[B(C_6F_5)F_3]^-$, $[B(C_6F_5)_3(CF_3)]^-$, $[B(C_6F_5)_2(CF_3)_2]$, $[B(C_6F_5)(CF_3)_3]^-$, $[B(C_6F_5)_3(C_6F_4CF_3)]^-$, $[B(C_6F_5)_2(C_6F_4CF_3)_2]^-$, $[B(C_6F_5)(C_6F_4CF_3)_3]^-$, $[B(C_6F_4CF_3)_3F]^-$, $[B(C_6F_4CF_3)_2F_2]^-$, $[B(C_6F_4CF_3)F_3]^-$, $[B(C_6F_4CF_3)_3(CF_3)]^-$, $[B(C_6F_4CF_3)_2(CF_3)_2]^-$, $[B(C_6F_4CF_3)(CF_3)_3]^-$, $[B(C_6F_5)_3(C_6H_{13})]^-$, $[B(C_6F_5)_2(C_6H_{13})_2]^-$, $[B(C_6F_5)(C_6H_{13})_3]^-$, $[B(C_6H_4CF_3)_4]^-$, $[B(C_6H_3F_2)_4]^-$, and the like may be cited. In the present invention, among the examples of the borate anion, $[B(C_6F_5)_4]^-$ is more preferable. In the present invention, the borate anion may be used singly or in a mixed form of two more members.

(2) A Salt Containing an Anion of the Formula (1)

A salt containing an anion of the formula (1) may be a salt formed between the borate anion of the formula (1) and a cation having near-infrared ray absorption ability, or a salt formed between the borate anion of the formula (1) and a cation having no near-infrared ray absorption ability. In the former case, a borate can act as a near-infrared ray absorption material (dye), and also can manifest improved durability, in particular, heat resistance and moisture resistance. In the latter case, because it does not manifest near-infrared ray absorption ability by itself, by being mixed with a near-infrared ray absorbing dye, durability, in particular, heat resistance and moisture resistance of the resultant mixed near-infrared ray absorption material (dye) can be significantly improved.

An embodiment of the latter case, namely, a borate of the present invention is a salt formed between the borate anion of the formula (1) and a cation having no near-infrared ray absorption ability, will be explained below.

As a salt containing an anion of the formula (1) according to the present invention, the following salt of the borate anion can be used: a salt of an alkaline metal such as lithium, sodium, potassium, rubidium and cesium; a salt of an alkaline earth metal such as beryllium, magnesium, calcium, strontium and barium; a salt of a transition metal salt such as silver, copper; a salt of an ammonium such as ammonium, n-butylammonium, dimethylammonium, trimethylammonium, triethylammonium, triisopropylammonium, tri-n-butylammonium, tetramethylammonium, tetraethylammonium, tetra-n-butylammonium and N,N-dimethylcyclohexylammonium; a salt of an anilinium such as N-methyanilinium, N,N-dimethylanilinium, N,N-dimethyl-4-methylanilinium, N,N-diethylanilinium, N,N-diphenylanilinium and N,N,N-trimethylanilinium; a salt of an pyridinium such as pyridinium, N-methylpyridinium, N-butylpyridinium, N-methyl-4-methylpyridinium, N-benzylpyridinium, 3-methyl-N-butylpyridinium, 2-methylpyridinium, 3-methylpyridinium, 4-methylpyridinium, 2,3-dimethylpyridinium, 2,4-dimethylpyridinium, 2,6-dimethylpyridinium, 3,4-dimethylpyridinium, 3,5-dimethylpyridinium, 2,4,6-trimethylpyridinium, 2-fluoropyridinium, 3-fluoropyridinium, 4-fluoropyridinium, 2,6-difluoropyridinium, 2,3,4,5,6-pentafluoropyridinium, 2-chloropyridinium, 3-chloropyridinium, 4-chloropyridinium, 2,3-dichloropyridinium, 2,5-dichloropyridinium, 2,6-dichloropyridinium, 3,5-dichloropyridinium, 3,5-dichloro-2,4,6-trifluoropyridinium, 2-bromopyridinium, 3-bromopyridinium, 4-bromopyridinium, 2,5-dibromopyridinium, 2,6-dibromopyridinium, 3,5-dibromopyridinium, 2-cyanopyridinium, 3-cyanopyridinium, 4-cyanopyridinium, 2-hydroxypyridinium, 3-hydroxypyridinium, 4-hydroxypyridinium, 2,3-dihydroxypyridinium, 2,4-dihydroxypyridinium, 2-methyl-5-ethylpyridinium, 2-chloro-3-cyanopyridinium, 4-carboxamide pyridinium, 4-carboxyaldehydepyridinium, 2-phenylpyridinium, 3-phenylpyridinium, 4-phenylpyridinium, 2,6-diphenylpyridinium, 4-nitropyridinium, 4-methoxypyridinium, 4-vinylpyridinium, 4-mercaptopyridinium, 4-t-butylpyridinium, 2,6-di-t-butylpyridinium, 2-benzylpyridinium, 3-acetylpyridinium, 4-ethylpyridinium, 2-carboxylic acid pyridinium, 4-carboxylic acid pyridinium, 2-benzoylpyridinium; a salt of an imidazolium such as imidazolium, 1-methylimidazolium, 1-ethyl-3-methylimidazolium, 1-propyl-3-methylimidazolium, 1-butyl-3-methylimidazolium, 1-hexyl-3-methylimidazolium, 1-methyl-3-octylimidazolium, 1-methyl-N-benzylimidazolium, 1-methyl-3-(3-phenylpropyl)imidazolium, 1-butyl-2,3-dimethylimidazolium, 1-ethyl-2,3-dimethylimidazolium; a salt of a pyrrolidinium such as 1-ethyl-1-methylpyrrolidinium and 1-butyl-1-methylpyrrolidinium; a salt of a quinolinium such as quinolinium, isoquinolinium; a salt of carbenium such as triphenylcarbenium and tri-4-methoxyphenylcarbenium; a salt of a phosphonium such as dimethylphenylphosphonium, triphenylphosphonium, tetraethylphosphonium and tetraphenylphosphonium; a salt of a sulfonium such as trimethylsulfonium and triphenylsulfonium; a salt of an iodonium such as diphenyl iodonium and di-4-methoxyphenyl iodonium, and the like. In this case, when a borate anion is used as a form of the alkaline earth metal salt, a salt according to the present invention takes a form wherein two borate anions are bonded per one alkaline earth metal.

Among the salts, a preferable cation having no near-infrared ray absorption ability includes an alkali metal salt, an ammonium salt and an organic cation salt containing nitrogen. Specifically, a salt comprising a cation having any of structure of sodium, ammonium, pyridinium, anilinium, imidazolium, pyrrolidinium, and quinolinium is preferably used. Preferably in particular, for example, N,N-dimethylcyclohexylammonium salt, N,N-dimethyl-4-methylcyclohexylammonium salt, N,N-diethylanilinium salt, 1-methyl-imidazolium salt and quinolinium salt of tetrakis (pentafluorophenyl) borate can be used. Because the borate does not have near-infrared ray absorption ability, it is preferably used with a near-infrared ray absorbing dye. In this case, a borate may be used singly or in a mixed form of two more members.

In this connection, in the present invention, the cation may be used alone as a counter ion of a borate anion, or as a mixed form of two or more members as counter ions of a borate anion.

Although an amount of a salt of an anion of the formula (1) formulated in near-infrared ray absorption material of the present invention can be selected, as appropriate, depending on applications, it is preferably in the range of 0.5 to 8 moles, and more preferably 1 to 5 moles, based on 1 mole of a near-infrared ray absorbing dye to be used in combination. In this case, the formulated amount of a salt of an anion below 0.5 mole would provide insufficient amount to be added of a boron atom bonded with an aryl group having an electron withdrawing group, which may not provide sufficient improvement of durability, while the amount over 8 moles would not provide effects comparable to the addition and may not be economical.

Then, explanation is given on the former case, namely, an embodiment wherein a borate of the present invention is a salt formed between a borate anion of the formula (1) and a cation having near-infrared ray absorption ability, in particular, an organic cation having near-infrared ray absorption ability. In this case, because a borate of itself also can serve as a near-infrared ray absorbing dye, a borate itself of the present invention can act as a near-infrared ray absorption material, and by the presence of a borate anion, the near-infrared ray absorption material has superior durability, in particular, heat resistance and moisture resistance.

A cation formable a counter ion with a borate anion of the formula (1) and having near-infrared ray absorption ability is not especially limited, so long as it is a cation having excellent near-infrared ray absorption ability at a wavelength in the range of 700 to 1200 nm. For example, a diimmonium cation and a cyanine dye based cation may be included. Among these, a diimmonium cation is superior in near-infrared ray absorption ability at a wavelength in the range of 900 to 1200 nm, while a cyanine dye based cation is superior in near-infrared ray absorption ability at a wavelength in the range of 700 to 1000 nm.

When a cation formable a counter ion with a borate anion of the formula (1) and having near-infrared ray absorption ability is a diimmonium cation, a diimmonium cation is not especially limited, so long as it has excellent efficiency of cutting near-infrared ray at a wavelength in the range of 900 to 1200 nm, and preferably a cation of the following formula (2). Such a diimmonium cation represented by the following formula (2) has high transparency invisible region, and by using in plasma display optics, it enables to improve appearance of a display, or by using in an optical filter for optical semiconductor element, it enables to enhance sensitivity of a CCD camera.

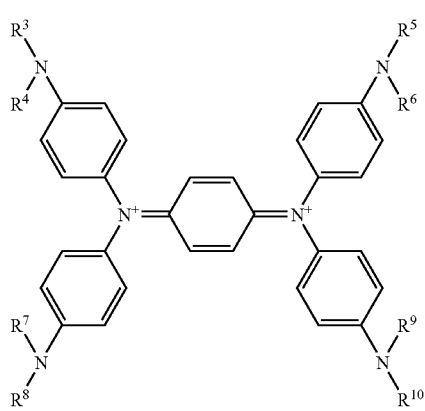

(2)

In the formula (2) representing the diimmonium cation, substituents represented by $R^3$ to $R^{10}$ include a hydrogen atom, a halogen atom and an alkyl group having carbon atoms of 1 to 10, or an alkyl group having carbon atoms of 1 to 10 and having a substituent.

As a halogen atom, for example, fluorine atom, chlorine atom, bromine atom and iodine atom may be included.

As an alkyl group having carbon atoms of 1 to 10, for example, linear, branched, or alicyclic alkyl groups such as methyl group, ethyl group, n-propyl group, isopropyl group, n-butyl group, isobutyl group, sec-butyl group, tert-butyl group, n-pentyl group, 1-methylbutyl group, 1-ethylpropyl group, 1,2-dimethylpropyl group, 1,1-dimethylpropyl group, neopentyl group, n-hexyl group and cyclohexyl group may be included.

As a substituent bondable to an alkyl group having carbon atoms of 1 to 10 which may have a substituent, cyano group; hydroxyl group; halogen atom such as fluorine atom, chlorine atom and bromine atom; an alkoxyl group having carbon atoms of 1 to 6, such as methoxy group, ethoxy group, n-propoxy group and n-butoxy group; an alkoxyalkoxy group having carbon atoms of 2 to 8 such as methoxymethoxy group, ethoxymethoxy group, methoxyethoxy group, ethoxyethoxy group, methoxypropoxy group, methoxybutoxy group and ethoxybutoxy group; an alkoxyalkoxyalkoxy group having carbon atoms of 3 to 15, such as methoxymethoxymethoxy group, methoxymethoxyethoxy group, methoxyethoxyethoxy group and ethoxyethoxyethoxy group; an allyloxy group; aryloxy group having carbon atoms of 6 to 12 such as phenoxy group, tolyloxy group, xylyloxy group and naphthyloxy group; an alkoxycarbonyl group having carbon atoms of 2 to 7 such methoxycarbonyl group, ethoxycarbonyl group, n-propoxycarbonyl group, isopropoxycarbonyl group and n-butoxycarbonyl group; an alkylcarbonyloxy group having carbon atoms of 2 to 7 such as methylcarbonyloxy group, ethylcarbonyloxy group, n-propylcarbonyloxy group and n-butylcarbonyloxy group; an alkoxycarbonyloxy group having carbon atoms of 2 to 7 such as methoxycarbonyloxy group, ethoxycarbonyloxy group, n-propoxycarbonyloxy group, n-butoxycarbonyloxy group, and the like may be included. Specifically, $R^3$ to $R^{10}$ include trifluoromethyl group, 2,2,2-trifluoroethyl group, 3,3,3,-trifluoropropyl group, 4,4,4-trifluorobutyl group, perfluoroethyl group, perfluoropropyl group, perfluorobutyl group, and the like.

In the present invention, $R^3$ to $R^{10}$ may be the same or different ones, however, it is preferable that all of them are the same. In addition, as for bonding positions of diamines, p-position relative to a nitrogen atom bonded to phenylenediamine skeleton is convenient in view of synthesis, although not being especially limited thereto.

A method for producing a salt between a borate anion of the formula (1) and a diimmonium cation of the formula (2) is not especially limited, and it can be produced by a known method or by a modified method of a known method. For example, a salt between a borate anion and a diimmonium cation can be produced by co-existing a borate anion of the formula (1) in a system of oxidizing a 1,4-phenylenediamine derivative by means of an oxidizing agent such as a silver salt, or by electrolytic oxidation. For example, it can be produced by a similar method to one described in JP-B-43-25335.

Specifically, a 1,4-phenylenediamine derivative wherein all of the substituents ($R^3$ to $R^{10}$) are the same can be obtained by reducing a product obtained by Ullmann reaction of p-phenylenediamine and 1-chloro-4-nitrobenzene to obtain an amine compound represented by the following formula (4),

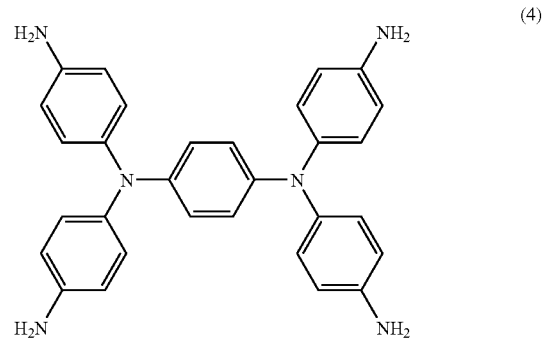

(4)

reacting the amine compound with a halide compound corresponding to desired $R^3$ to $R^{10}$ (for example, $BrCH_2CH(CH_3)_2$, when all of $R^3$ to $R^{10}$ are i-$C_4H_9$) in a water-soluble polar solvent such as DMF (N,N-dimethylformamide), DMI (1,3-dimethyl-2-imidazolidinone) and NMP (N-methylpyrrolidone) preferably at 50 to 140° C. In the above method, plurality kinds of substituents may be introduced by using plurality halide compounds in combination.

Subsequently, the 1,4-phenylenediamine derivative thus synthesized is dissolved in a water-soluble polar solvent, such as DMF, DMI and NMP, with a borate of the formula (1) (for example, sodium tetrakis(pentafluorophenyl) borate), and by the addition of an oxidizing agent such as a silver salt and reacting the mixture at 5 to 70° C., a salt between a borate anion of the formula (1) and a diimmonium cation of the formula (2) can be obtained. In addition, instead of using a silver salt, electrolytic oxidation may be adopted. In this case, a borate of the formula (1) is used in an amount of not less than two moles per one mole of a 1,4-phenylenediamine derivative.

Alternatively, a diimmonium dye having a borate anion represented by the formula (1) can be produced also by reacting a well-known diimmonium salt with a borate anion represented by the formula (1) in an organic solvent. As a salt having a borate anion of the formula (1) which can be used in such a method, alkali metal salt, alkaline earth metal salt and transition metal salt and the like, of borate anion represented by the formula (1) may be included. An alkali metal salt is preferable and lithium salt, sodium salt, potassium salt, for example, lithium salt, sodium salt and potassium salt of tetrakis(pentafluorophenyl) borate are more preferable.

In addition, as a diimmonium dye, a salt comprising diimmonium cation of the formula (2) and, hexafluoroantimonate ion, perchlorate ion, hexafluorophosphate ion and tetrafluoroborate ion can be used.

For the amount of the borate anion used for the reaction between the borate compound and the well-known diimmonium dye in an organic solvent, the borate compound is used in an amount of not lower than two moles, preferably in the range of 2 to 5 moles and more preferably 2 to 4 moles, per one mole of the diimmonium salt. The amount below two moles would provide low substitution ratio and the amount over 5 moles would not be economical.

As an organic solvent used in the reaction, for example, an aromatic solvent such as toluene and, xylene; a ketone-based solvent such as acetone, methyl ethyl ketone and methyl isobutyl ketone; an ester-based solvent such as ethyl acetate and butyl acetate; a nitrile-based solvent such as acetonitrile; an alcohol-based solvent such as methanol, ethanol and isopropyl alcohol; an ether-based solvent such as tetrahydrofuran and dibutyl ether; a glycol ether-based solvent such as butylcellosolve and propylene glycol n-propylether; an amide-based solvent such as formamide and N,N-dimethylformamide; and a halogen-based solvent such as methylenechloride and chloroform can be used. These solvents may be used singly or in a mixed form of two more members. A solvent having high solubility to both of a borate compound and a diimmonium salt may be preferably used.

The amount of the solvent to be used is preferably in the range of 1 to 100 times, and more preferably 2 to 50 times, the total weight of a borate compound and a diimmonium salt. The amount below one time would provide poor solubility of a borate compound and a diimmonium salt, while the amount over 100 times would not be economical. In view of suppressing decomposition of a diimmonium salt, the reaction temperature is preferably not higher than 60° C., and more preferably in the range of 10 to 50° C. The reaction is usually completed spontaneously.

When a desired compound is separated by standing still of a reaction solution, it can be recovered by filtration. When a desired compound is not deposited even by standing still of a reaction solution, the desired compound can be separated by adding deionized water into the reaction solution thereby forming a desired compound and recovering it by filtration. The amount of deionized water to be used is preferably in the range of 5 to 1000 times weight, and more preferably 10 to 500 times, of the reaction solution. The amount less than 5 times would reduce yield, while the amount over 1000 times would not be economical due to generation of too much amount of waste water. The product recovered may be washed with deionized water to remove unnecessary ions derived from raw materials.

The borate in such an embodiment, in particular, in the case of a salt between a borate anion and a diimmonium cation, has high near-infrared ray absorption ability at a wavelength in the range of 900 to 1200 nm, and high transparency in visible region, and thus can advantageously be used as a near-infrared ray absorbing dye. By the addition of this borate, near-infrared ray absorption material can be obtained. In addition, it can also be used as optical recording material.

Also in the case when a borate of the present invention is a salt between a borate anion of the formula (1) and a cyanine dye based cation, the borate has near-infrared ray absorption ability. A cyanine dye based cation in this case is not especially limited, so long as it has high near-infrared ray absorption ability at a wavelength in the range of 700 to 1000 nm. Preferably, an indolium-based cation can be used. Specifically, cations represented by the following formulae (a) to (i) may be included, although they are by no means limited thereto. Borates in such embodiments have high near-infrared ray absorption ability at a wavelength in the range of 700 to 1000 nm, and high transparency in visible region, and thus can advantageously be used as a near-infrared ray absorbing dye. By the addition of this borate, near-infrared ray absorption material can be obtained. In addition, it can also be used as optical recording material.

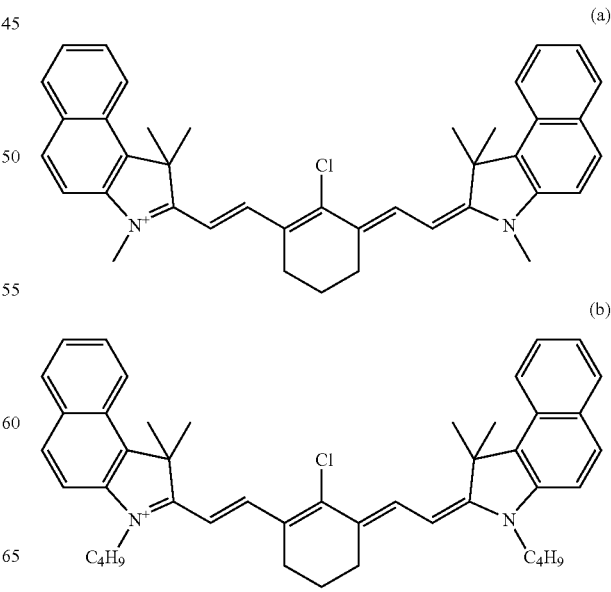

-continued

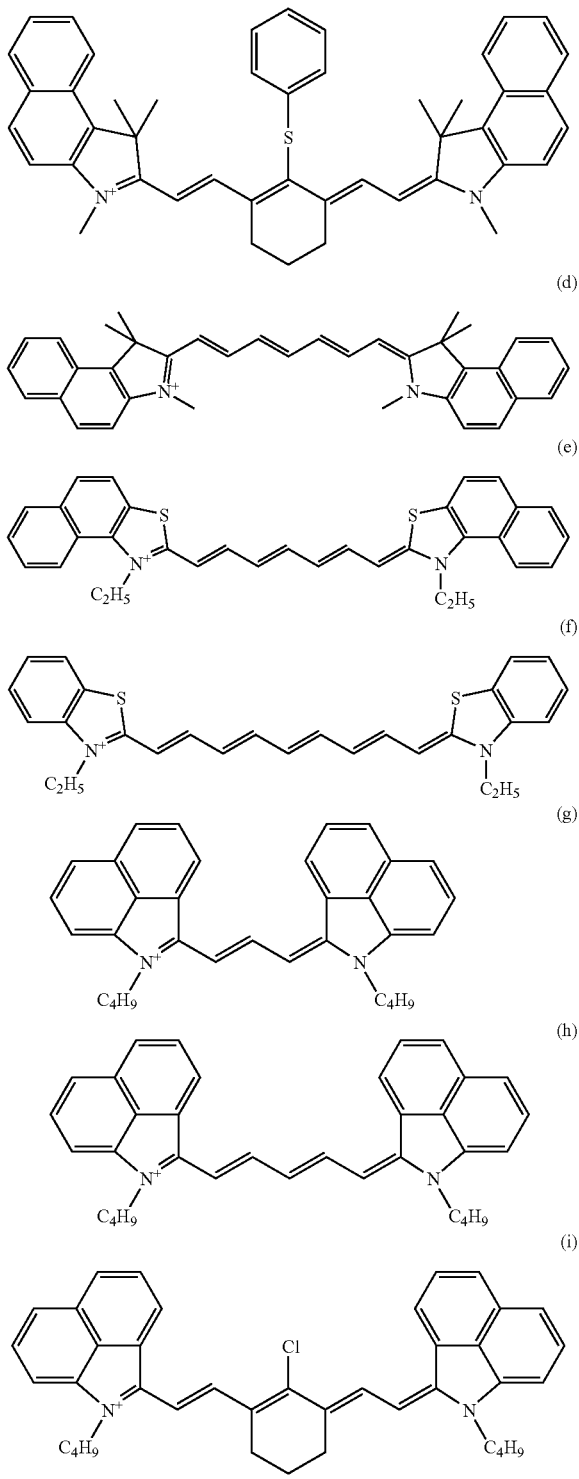

(3) A Near-Infrared Ray Absorbing Dye

A borate of the present invention can improve durability, in particular heat resistance and moisture resistance of near-infrared ray absorption material (dye). Therefore, the second aspect of the present invention relates to a near-infrared ray absorption material containing the borate of the present invention and a near-infrared ray absorbing dye. As described above, because a borate of the present invention can improve durability, in particular heat resistance and moisture resistance of near-infrared ray absorption material (dye), the near-infrared ray absorption material of the present invention can fulfill superior durability, in particular heat resistance and moisture resistance. In addition, the near-infrared ray absorption material of the present invention is superior also in transparency in visible region.

In the present invention, as described in the item (2), when a borate of the present invention is a salt between a borate anion of the formula (1) and a cation having near-infrared ray absorption ability, a borate of itself can be a near-infrared ray absorbing dye. Therefore, in such a case, the near-infrared ray absorption material of the second aspect of the present invention may be a borate of the present invention of itself. In this case, the near-infrared ray absorption material may be composed of one members of a borate or may be composed of a mixture of two or more members of borates. Even in this case, to assist desired near-infrared ray absorption ability or to attain absorption at another near-infrared ray wavelength, another near-infrared ray absorbing dye(s), as described below, may be used in combination. In addition, a salt between a borate anion of the formula (1) and a cation having near-infrared ray absorption ability, and a salt between a borate anion of the formula (1) and a cation having no near-infrared ray absorption ability may be used in combination. By such use, durability, in particular heat resistance and moisture resistance of the dye can further be improved. In addition, when a borate of the present invention is a salt between a borate anion of the formula (1) and a cation having no near-infrared ray absorption ability, such combined use of a near-infrared ray absorbing dye, as described below, is essential. By the presence of a borate, durability, in particular heat resistance and moisture resistance of a near-infrared ray absorbing dye can be improved.

A near-infrared ray absorbing dye which can be used in near-infrared ray absorption material of the present invention is not especially limited and, for example, in addition to a salt between a borate anion of the formula (1) and a cation having near-infrared ray absorption ability, as described above, a well-known near-infrared ray absorbing dyes can be used. Specifically, a cyanine-based, polymethine-based, squarylium-based, porphyrin-based, dithiol metal complex-based, phthalocyanine-based, diimmonium-based near-infrared ray absorption dye, and the like may be included. Among these, cyanine-based and diimmonium-based near-infrared ray absorbing dyes are superior in transparency in visible region, and a phthalocyanine-based near-infrared ray absorbing dye is superior in durability of a near-infrared ray absorbing dye and thus these dyes are preferably used.

In the present invention, the diimmonium-based dye is a salt comprising a diimmonium cation of the formula (2) and a counter anion. The counter anion is not especially limited, and chloride ion, bromide ion, iodide ion, perchlorate, nitrate ion, benzenesulfonate ion, p-toluenesulfonate ion, methyl sulfate ion, ethyl sulfate ion, propyl sulfate ion, tetrafluoroborate ion, tetraphenylborate ion, tetrakis(pentafluorophenyl) borate ion, bis(trifluoromethanesulfone)imide ion, bis(pentafluoroethanesulfone) imide ion, pentafluoroethanesulfone trifluoromethanesulfoneimide ion, trifluoromethanesulfone heptafluoropropanesulfoneimide ion, nonafluorobutanesulfone trifluoromethanesulfoneimide ion, 1,3-disulfonyl-hexafluoropropyleneimide ion, hexafluorophosphate ion, benzenesulfinate ion, acetate ion, trifluoroacetate ion, propionate ion, benzoate ion, oxalate ion, succinate ion, malonate ion, oleate ion, stearate ion, citrate ion, hydrogen diphosphate ion, dihydrogen phosphate ion, pentachlorostannate ion, chlorosulfonate ion, fluorosulfonate ion, trifluoromethane sulfonate ion, hexafluoroarsenate ion, hexafluoroantimonate ion, molybdate ion, tungstate ion, titanate ion, zirconate ion, sulfate ion, vanadate ion, borate ion, and the like can be used. In this case, because a diimmonium cation is a bivalent cation, as represented by the formula (2), for example, when a monovalent anion such as a chloride ion is used, a diimmonium-based dye according to the present invention has two anions bound per one dimmonium cation. Among the salts, a salt between diimmonium cation and hexafluoroantimonate ion, perchlorate ion, hexafluorophosphate ion, tetrafluoroborate ion, bis(trifluoromethanesulfone)imide ion and tetrakis(pentafluorophenyl)borate ion, particularly preferably, a salt between a diimmonium cation and tetrakis(pentafluorophenyl)borate ion is preferably used in the present invention. Here, a salt between a diimmonium cation and a tetrakis(pentafluorophenyl)borate ion is one example of a borate having near-infrared ray absorption ability in the first aspect of the present invention.

A cyanine-based dye used in the present invention is not especially limited, so long as it is one superior in transparency in visible region and near-infrared ray absorption ability, and a salt between an indolium-based cation and a counter anion can preferably be used. As the indolium-based cation, cations represented by the formulae (a) to (i) can preferably be used, however not limited thereto. As the counter anion, a similar counter anion listed in a diimmonium-based dye can be used without limitation especially. Here, a salt between an indolium-based cation and tetrakis(pentafluorophenyl)borate ion is one example of a borate having near-infrared ray absorption ability in the first aspect of the present invention.

In more specifically, commercially available products can be used such as ADS812MI produced from American Dye Source Inc. as a cyanine-based dye containing a cation represented by the general formula (a); S0712 produced from FEW Chemicals GmbH as a cyanine-based dye containing a cation represented by the general formula (b); S0726 produced from FEW Chemicals GmbH as a cyanine-based dye containing a cation represented by the general formula (c); ADS780MT produced from American Dye Source Inc. as a cyanine-based dye containing a cation represented by the general formula (d); S0006 produced from FEW Chemicals GmbH as a cyanine-based dye containing a cation represented by the general formula (e); S0081 produced from FEW Chemicals GmbH as a cyanine-based dye containing a cation represented by the general formula (f); S0773 produced from FEW Chemicals GmbH as a cyanine-based dye containing a cation represented by the general formula (g); S0772 produced from FEW Chemicals GmbH as a cyanine-based dye containing a cation represented by the general formula (h); and S0734 produced from FEW Chemicals GmbH as a cyanine-based dye containing a cation represented by the general formula (i), and the like.

A phthalocyanine-based compound which can be used in the present invention is not especially limited, so long as it has excellent near-infrared ray absorption ability, and a well-known phthalocyanine-based compound can be used. A compound represented by the following formula (X) or a compound represented by the following formula (Y) may be preferably included.

A phthalocyanine-based compound represented by the formula (X):

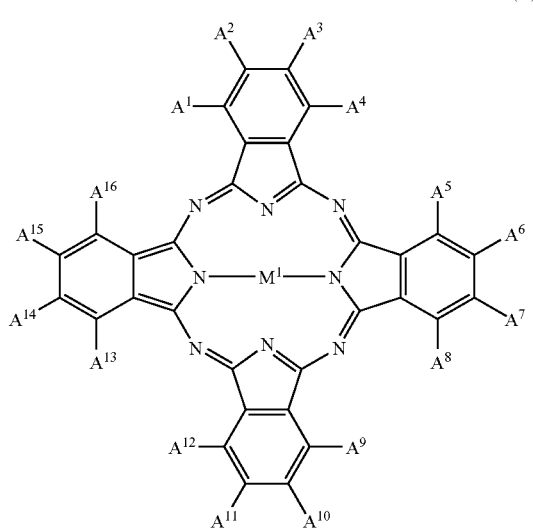

(X)

In the formula (X), $A^1$ to $A^{16}$ represent a functional group and each independently represents a hydrogen atom, a halogen atom, hydroxyl group, hydroxylsulfonyl group, carboxylic group, thiol group, alkyl group having carbon atoms of 1 to 20 which may be substituted, alkoxyl group having carbon atoms of 1 to 20 which may be substituted, aryl group having carbon atoms of 6 to 20 which may be substituted, aryloxy group having carbon atoms of 6 to 20 which may be substituted, aralkyl group having carbon atoms of 7 to 20 which may be substituted, aralkyloxy group having carbon atoms of 7 to 20 which may be substituted, alkylthio group having carbon atoms of 1 to 20 which may be substituted, arylthio group having carbon atoms of 6 to 20 which may be substituted, aralkylthio group having carbon atoms of 7 to 20 which may be substituted, alkylsulfonyl group having carbon atoms of 1 to 20 which may be substituted, arylsulfonyl group having carbon atoms of 6 to 20 which may be substituted, aralkylsulfonyl group having carbon atoms of 7 to 20 which may be substituted, acyl group having carbon atoms of 1 to 20 which may be substituted, alkoxycarbonyl group having carbon atoms of 2 to 20 which may be substituted, aryloxycarbonyl group having carbon atoms of 6 to 20 which may be substituted, aralkyloxycarbonyl group having carbon atoms of 2 to 20 which may be substituted, alkylcarbonyloxy group having carbon atoms of 2 to 20 which may be substituted, arylcarbonyloxy group having carbon atoms of 6 to 20 which may be substituted, aralkylcarbonyloxy group having carbon atoms of 8 to 20 which may be substituted, a heterocyclic group having carbon atoms of 2 to 20 which may be substituted, amino group which may be substituted, aminosulfonyl group which may be substituted and aminocarbonyl group which may be substituted. Functional groups $A^1$ to $A^{16}$ may be the same or different each other, and also in the case of the same kind, they may be the same or different, and functional groups themselves may be bonded together via a linking group. $M^1$ represents 2 hydrogen atoms, bivalent metal atom, trivalent or tetravalent substituted metal atom or oxy metal. In the present specification, "acyl group" means similar definition as described in page 17 of "General Dictionary of Scientific Technical Terminology", the third edition, published from Daily Industrial Newspaper Co., Ltd., and specifically is referred to as a group derived from an organic acid by removal of a hydroxyl group, and represented by a formula: RCO— (wherein R represents an aliphatic group, an alicyclic group or an aromatic group).

(In the Case when a Terminal is a Functional Group Other than an Amino Group)

In the formula (X), a halogen atom as a functional group $A^1$ to $A^{16}$ includes fluorine atom, chlorine atom, bromine atom and iodine atom. As an alkyl group having carbon atoms of 1 to 20 which may be substituted, a linear, branched or cyclic alkyl group such as methyl group, ethyl group, n-propyl group, iso-propyl group, n-butyl group, iso-butyl group, sec-butyl group, t-butyl group, n-pentyl group, n-hexyl group, cyclohexyl group, n-heptyl group, n-octyl group and 2-ethylhexyl group may be included, however, it is not limited thereto. As an alkoxyl group having carbon atoms of 1 to 20 which may be substituted, a linear, branched or cyclic alkoxy group such as methoxy group, ethoxy group, n-propyloxy group, iso-propyloxy group, n-butyloxy group, iso-butyloxy group, sec-butyloxy group, t-butyloxy group, n-pentyloxy group, n-hexyloxy group, cyclohexyloxy group, n-heptyloxy group, n-octyloxy group and 2-ethylhexyloxy group may be included, however, it is not limited thereto. As an aryl group having carbon atoms of 6 to 20 which may be substituted, phenyl group, naphthyl group, and the like may be included, however, it is not limited thereto. As an aryloxy group having carbon atoms of 6 to 20 which may be substituted, phenoxy group, naphthoxy group, and the like may be included, however, it is not limited thereto. As an aralkyl group having carbon atoms of 7 to 20 which may be substituted, benzyl group, phenethyl group, diphenylmethyl group, and the like may be included, however, it is not limited thereto. As an aralkyloxy group having carbon atoms of 7 to 20 which may be substituted, benzyloxy group, phenethyloxy group, diphenylmethyloxy group, and the like may be included, however, it is not limited thereto. As an alkylthio group having carbon atoms of 1 to 20 which may be substituted, a linear, branched or cyclic alkylthio group such as methylthio group, ethylthio group, n-propylthio group, iso-propylthio group, n-butylthio group, iso-butylthio group, sec-butylthio group, t-butylthio group, n-pentylthio group, n-hexylthio group, cyclohexylthio group, n-heptylthio group, n-octylthio group and 2-ethylhexylthio group may be included, however, it is not limited thereto. As an arylthio group having carbon atoms of 6 to 20 which may be substituted, phenylthio group, naphthylthio group, and the like may be included, however, it is not limited thereto. As an aralkylthio group having carbon atoms of 7 to 20 which may be substituted, benzylthio group, phenethylthio group, diphenylmethylthio group, and the like may be included, however, it is not limited thereto. As an alkylsulfonyl group having carbon atoms of 1 to 20 which may be substituted, a linear, branched or cyclic alkyl group such as methylsulfonyl group, ethylsulfonyl group, n-propylsulfonyl group, iso-propylsulfonyl group, n-butylsulfonyl group, iso-butylsulfonyl group, sec-butylsulfonyl group, t-butylsulfonyl group, n-pentylsulfonyl group, n-hexylsulfonyl group, cyclohexylsulfonyl group, n-heptylsulfonyl group, n-octylsulfonyl group and 2-ethylhexylsulfonyl group may be included, however, it is not limited thereto. As an arylsulfonyl group having carbon atoms of 6 to 20 which may be substituted, phenylsulfonyl group, naphthylsulfonyl group, and the like may be included, however, it is not limited thereto. As an aralkylsulfonyl group which may be substituted, benzylsulfonyl group, phenethylsulfonyl group, diphenylmethylsulfonyl group, and the like may be included, however, it is not limited thereto. As an acyl group having carbon atoms of 1 to 20 which may be substituted, a linear, branched or cyclic alkylcarbonyl group such as methylcarbonyl group, ethylcarbonyl group, n-propylcarbonyl group, iso-propylcarbonyl group, n-butylcarbonyl group, iso-butylcarbonyl group, sec-butylcarbonyl group, t-butylcarbonyl group, n-pentylcarbonyl group, n-hexylcarbonyl group, cyclohexylcarbonyl group, n-heptylcarbonyl group, n-octylcarbonyl group and 2-ethylhexylcarbonyl group; an arylcarbonyl group such as benzylcarbonyl group and phenylcarbonyl group; and an aralkylcarbonyl group such as benzoyl group may be included, however, it is not limited thereto. As an alkoxycarbonyl group having carbon atoms of 2 to 20 which may be substituted, methoxycarbonyl group, ethoxycarbonyl group, n-propyloxycarbonyl group, iso-propyloxycarbonyl group, n-butyloxycarbonyl group, iso-butyloxycarbonyl group, sec-butyloxycarbonyl group, t-butyloxycarbonyl group, n-pentyloxycarbonyl group, n-hexyloxycarbonyl group, cyclohexyloxycarbonyl group, n-heptyloxycarbonyl group, n-octyloxycarbonyl group, 2-ethylhexyloxycarbonyl group, and the like may be included, however, it is not limited thereto. As an aryloxycarbonyl group having carbon atoms of 7 to 20 which may be substituted, phenoxycarbonyl group, naphthylcarbonyl group, and the like may be included, however, it is not limited thereto. As an aralkyloxycarbonyl group having carbon atoms of 8 to 20 which may be substituted, benzyloxycarbonyl group, phenethyloxycarbonyl group, diphenylmethyloxycarbonyl group, and the like may be included, however, it is not limited thereto. As an alkylcarbonyloxy group having carbon atoms of 2 to 20 which may be substituted, acetyloxy group, ethylcarbonyloxy group, n-propylcarbonyloxy group, iso-propylcarbonyloxy group, n-butylcarbonyloxy group, iso-butylcarbonyloxy group, sec-butylcarbonyloxy group, t-butylcarbonyloxy group, n-pentylcarbonyloxy group, n-hexylcarbonyloxy group, cyclohexylcarbonyloxy group, n-heptylcarbonyloxy group, 3-heptylcarbonyloxy group, n-octylcarbonyloxy group, and the like may be included, however, it is not limited thereto. As an arylcarbonyloxy group having carbon atoms of 7 to 20 which may be substituted, benzoyloxy group, and the like may be included, however, it is not limited thereto. As an aralkylcarbonyloxy group having carbon atoms of 8 to 20 which may be substituted, benzylcarbonyloxy group, and the like may be included, however, it is not limited thereto. As a heterocyclic group having carbon atoms of 2 to 20 which may be substituted, pyrrole group, imidazole group, piperidine group, morpholine group, and the like may be included, however, it is not limited thereto.

In addition, as a substituent which may be present, if necessary, at a functional group $A^1$ to $A^{16}$ in the formula (X), namely, alkyl group, alkoxy group, aryl group, aryloxy group, aralkyl group, aralkyloxy group, alkylthio group, arylthio group, aralkylthio group, alkylsulfonyl group, arylsulfonyl group, aralkylsulfonyl group, acyl group, alkoxycarbonyl group, aryloxycarbonyl group, aralkyloxycarbonyl group, alkylcarbonyloxy group, arylcarbonyloxy group, aralkylcarbonyloxy group and heterocyclic group, for example, halogen atom, acyl group, alkyl group, phenyl group, alkoxy group, halogenated alkyl group, halogenated alkoxy group, nitro group, amino group, alkylamino group, alkylcarbonylamino group, arylamino group, arylcarbonylamino group, carbonyl group, alkoxycarbonyl group, alkylaminocarbonyl group, alkoxysulfonyl group, alkylthio group, carbamoyl group, aryloxycarbonyl group, cyano group and heterocyclic group may be included, however, it is not limited thereto. These substituents may be present in plural and when they are present in plural, they may be the same or different each other, and even in the case of the same kind, they may be the same or different. These substrates themselves may be bonded together via a linking group.

(In the Case when a Terminal is a Functional Group of an Amino Group)

As a substituent to a functional group $A^1$ to $A^{16}$ in the formula (X), namely, an amino group which may be substituted, an aminosulfonyl group which may be substituted and an aminocarbonyl group which may be substituted, hydrogen atom; a linear, branched, or cyclic alkyl group such as methyl group, ethyl group, n-propyl group, n-butyl group, sec-butyl group, n-pentyl group, n-hexyl group, 2-ethylhexyl group and cyclohexyl group; aryl group such as phenyl group, naphthyl group; an aralkyl group such as benzyl group and phenethyl group; acetyl group; a linear, branched, or cyclic alkylcarbonyl group such as ethylcarbonyl group, n-propylcarbonyl group, iso-propylcarbonyl group, n-butylcarbonyl group, iso-butylcarbonyl group, sec-butylcarbonyl group, t-butylcarbonyl group, n-pentylcarbonyl group, n-hexylcarbonyl group, cyclohexylcarbonyl group, n-heptylcarbonyl group, 3-heptylcarbonyl group, n-octylcarbonyl group; arylcarbonyl group such as benzoyl group and naphthylcarbonyl group; an aralkylcarbonyl group such as benzylcarbonyl group, and the like may be included, however, it is not limited thereto and these substituents may further be substituted with substituents. These substituents may be present in 0, one or two and when two substituents are present, they may be the same or different each other, and even in the case of the same kind, they may be the same or different and functional groups themselves may be bonded together via a linking group.

As a substituent which may further be present on alkyl group, aryl group, aralkyl group, alkylcarbonyl group, arylcarbonyl group and aralkylcarbonyl group, which are substituents for the amino group which may be substituted, aminosulfonyl group which may be substituted and aminocarbonyl group which may be substituted, for example, halogen atom, acyl group, alkyl group, phenyl group, alkoxy group, halogenated alkyl group, halogenated alkoxy group, nitro group, amino group, alkylamino group, alkylcarbonylamino group, arylamino group, arylcarbonylamino group, carbonyl group, alkoxycarbonyl group, alkylaminocarbonyl group alkoxysulfonyl group, alkylthio group, carbamoyl group, aryloxycarbonyl group, cyano group and heterocyclic group may be included, however, it is not limited thereto. These substituents may be present in plural, and when they are present in plural, they may be the same or different each other, and even in the case of the same kind, they may be the same or different and substituents themselves may be bonded together via a linking group.

In addition, as an example of a bivalent metal as metal $M^1$, Cu(II), Co(II), Zn(II), Fe(II), Ni(II), Ru(II), Rh(II), Pd(II), Pt(II), Mn(II), Mg(II), Ti(II), Be(II), Ca(II), Ba(II), Cd(II), Hg(II), Pb(II), Sn(II), and the like may be included, however, it is not limited thereto. As an example of a trivalent substituted metal atom, Al—F, Al—Cl, Al—Br, Al—I, Fe—Cl, Ga—F, Ga—Cl, Ga—I, Ga—Br, In—F, In—Cl, In—Br, In—I, Tl—F, Tl—Cl, Tl—Br, Tl—I, Al—$C_6H_5$, Al—$C_6H_4$(CH_3), In—$C_6H_5$, In—$C_6H_4$(CH_3), In—$C_6H_5$, Mn(OH), Mn(O$C_6H_5$), Mn[OSi(CH_3)_3], Ru—Cl, and the like may be included, however, it is not limited thereto. As an example of a tetravalent substituted metal atom, $CrCl_2$, $SiF_2$, $SiCl_2$, $SiBr_2$, $SiI_2$, $ZrCl_2$, $GeF_2$, $GeCl_2$, $GeBr_2$, $GeI_2$, $SnF_2$, $SnCl_2$, $SnBr_2$, $TiF_2$, $TiCl_2$, $TiBr_2$, $Ge(OH)_2$, $Mn(OH)_2$, $Si(OH)_2$, $Sn(OH)_2$, $Zr(OH)_2$, $Cr(R_1)_2$, $Ge(R_1)_2$, $Si(R_1)_2$, $Sn(R_1)_2$, $Ti(R_1)_2$ {$R_1$ represents alkyl group, phenyl group, naphthyl group, and derivatives thereof}, $Cr(OR_2)_2$, $Ge(OR_2)_2$, $Si(OR_2)_2$, $Sn(OR_2)_2$, $Ti(OR_2)_2$ {$R_2$ represents alkyl group, phenyl group, naphthyl group, trialkylsilyl group, dialkylalkoxysilyl group and derivatives thereof}, $Sn(SR_3)_2$, $Ge(SR_3)_2$ {$R_3$ represents alkyl group, phenyl group, naphthyl group, and derivatives thereof}, and the like may be included, however, it is not limited thereto. As an example of an oxymetal, VO, MnO, TiO, and the like may be included, however, it is not limited thereto.

A phthalocyanine-based compound represented by formula (Y)

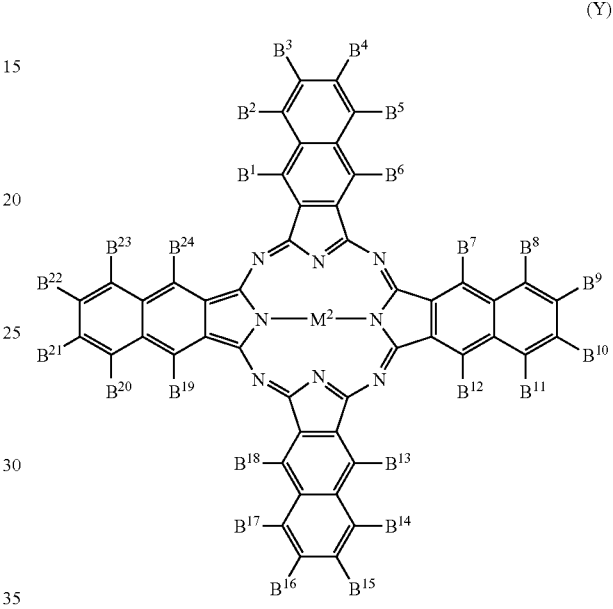

(Y)

In the formula (Y), $B^1$ to $B^{24}$ represent functional groups and each independently represents a hydrogen atom, a halogen atom, hydroxyl group, hydroxylsulfonyl group, carboxylic acid group, thiol group, alkyl group having carbon atoms of 1 to 20 which may be substituted, alkoxyl group having carbon atoms of 1 to 20 which may be substituted, aryl group having carbon atoms of 6 to 20 which may be substituted, aryloxy group having carbon atoms of 6 to 20 which may be substituted, aralkyl group having carbon atoms of 7 to 20 which may be substituted, aralkyloxy group having carbon atoms of 7 to 20 which may be substituted, alkylthio group having carbon atoms of 1 to 20 which may be substituted, arylthio group having carbon atoms of 6 to 20 which may be substituted, aralkylthio group having carbon atoms of 7 to 20 which may be substituted, alkylsulfonyl group having carbon atoms of 1 to 20 which may be substituted, arylsulfonyl group having carbon atoms of 6 to 20 which may be substituted, aralkylsulfonyl group having carbon atoms of 7 to 20 which may be substituted, acyl group having carbon atoms of 1 to 20 which may be substituted, alkoxycarbonyl group having carbon atoms of 2 to 20 which may be substituted, aryloxycarbonyl group having carbon atoms of 6 to 20 which may be substituted, aralkyloxycarbonyl group having carbon atoms of 2 to 20 which may be substituted, alkylcarbonyloxy group having carbon atoms of 2 to 20 which may be substituted, arylcarbonyloxy group having carbon atoms of 6 to 20 which may be substituted, aralkylcarbonyloxy group having carbon atoms of 8 to 20 which may be substituted, a heterocyclic group having carbon atoms of 2 to 20 which may be substituted, amino group which may be substituted and aminosulfonyl group which may be substituted and aminocarbonyl group which may be substituted. Functional groups $B^1$ to $B^{24}$ may be the same or different each other, and even in the case of the same kind, they may be the same or different and functional groups themselves may be bonded together via a linking group. $M^2$ represents 2 hydrogen atoms, bivalent metal atom, trivalent or tetravalent substituted metal atom or oxy metal.

(In the Case when a Terminal is a Functional Group Other than an Amino Group)

In the formula (Y), a halogen atom as a functional group $B^1$ to $B^{24}$ includes fluorine atom, chlorine atom, bromine atom and iodine atom. As an alkyl group having carbon atoms of 1 to 20 which may be substituted, a linear, branched, or cyclic alkyl group such as methyl group, ethyl group, n-propyl group, iso-propyl group, n-butyl group, iso-butyl group, sec-butyl group, t-butyl group, n-pentyl group, n-hexyl group, cyclohexyl group, n-heptyl group, n-octyl group and 2-ethylhexyl group may be included, however, it is not limited thereto. As an alkoxyl group having carbon atoms of 1 to 20 which may be substituted, a linear, branched, or cyclic alkoxy group such as methoxy group, ethoxy group, n-propyloxy group, iso-propyloxy group, n-butyloxy group, iso-butyloxy group, sec-butyloxy group, t-butyloxy group, n-pentyloxy group, n-hexyloxy group, cyclohexyloxy group, n-heptyloxy group, n-octyloxy group and 2-ethylhexyloxy group may be included, however, it is not limited thereto. As an aryl group having carbon atoms of 6 to 20 which may be substituted, phenyl group, naphthyl group, and the like may be included, however, it is not limited thereto. As an aryloxy group having carbon atoms of 6 to 20 which may be substituted, phenoxy group, naphthoxy group, and the like may be included, however, it is not limited thereto. As an aralkyl group having carbon atoms of 7 to 20 which may be substituted, benzyl group, phenethyl group, diphenylmethyl group, and the like may be included, however, it is not limited thereto. As an aralkyloxy group having carbon atoms of 7 to 20 which may be substituted, benzyloxy group, phenethyloxy group and diphenylmethyloxy group, and the like may be included, however, it is not limited thereto. As an alkylthio group having carbon atoms of 1 to 20 which may be substituted, a linear, branched or cyclic alkylthio group such as methylthio group, ethylthio group, n-propylthio group, iso-propylthio group, n-butylthio group, iso-butylthio group, sec-butylthio group, t-butylthio group, n-pentylthio group, n-hexylthio group, cyclohexylthio group, n-heptylthio group, n-octylthio group and 2-ethylhexylthio group may be included, however, it is not limited thereto. As an arylthio group having carbon atoms of 6 to 20 which may be substituted, phenylthio group, naphthylthio group, and the like may be included, however, it is not limited thereto. As an aralkylthio group having carbon atoms of 7 to 20 which may be substituted, benzylthio group, phenethylthio group, diphenylmethylthio group, and the like may be included, however, it is not limited thereto. As an alkylsulfonyl group having carbon atoms of 1 to 20 which may be substituted, a linear, branched or cyclic alkyl group such as methylsulfonyl group, ethylsulfonyl group, n-propylsulfonyl group, iso-propylsulfonyl group, n-butylsulfonyl group, iso-butylsulfonyl group, sec-butylsulfonyl group, t-butylsulfonyl group, n-pentylsulfonyl group, n-hexylsulfonyl group, cyclohexylsulfonyl group, n-heptylsulfonyl group, n-octylsulfonyl group and 2-ethylhexylsulfonyl group may be included, however, it is not limited thereto. As an arylsulfonyl group having carbon atoms of 6 to 20 which may be substituted, phenylsulfonyl group, naphthylsulfonyl group, and the like may be included, however, it is not limited thereto. As an aralkylsulfonyl group which may be substituted, benzylsulfonyl group, phenethylsulfonyl group, diphenylmethylsulfonyl group, and the like may be included, however, it is not limited thereto. As an acyl group having carbon atoms of 1 to 20 which may be substituted, a linear, branched, or cyclic alkylcarbonyl group such as methylcarbonyl group, ethylcarbonyl group, n-propylcarbonyl group, iso-propylcarbonyl group, n-butylcarbonyl group, iso-butylcarbonyl group, sec-butylcarbonyl group, t-butylcarbonyl group, n-pentylcarbonyl group, n-hexylcarbonyl group, cyclohexylcarbonyl group, n-heptylcarbonyl group, n-octylcarbonyl group and 2-ethylhexylcarbonyl group; an arylcarbonyl group such as benzylcarbonyl group, phenylcarbonyl group; and an aralkylcarbonyl group such as benzoyl group may be included, however, it is not limited thereto. As an alkoxycarbonyl group having carbon atoms of 2 to 20 which may be substituted, methoxycarbonyl group, ethoxycarbonyl group, n-propyloxycarbonyl group, iso-propyloxycarbonyl group, n-butyloxycarbonyl group, iso-butyloxycarbonyl group, sec-butyloxycarbonyl group, t-butyloxycarbonyl group, n-pentyloxycarbonyl group, n-hexyloxycarbonyl group, cyclohexyloxycarbonyl group, n-heptyloxycarbonyl group, n-octyloxycarbonyl group, 2-ethylhexyloxycarbonyl group, and the like may be included, however, it is not limited thereto. As an aryloxycarbonyl group having carbon atoms of 7 to 20 which may be substituted, phenoxycarbonyl group, naphthylcarbonyl group, and the like may be included, however, it is not limited thereto. As an aralkyloxycarbonyl group having carbon atoms of 8 to 20 which may be substituted, benzyloxycarbonyl group, phenethyloxycarbonyl group, diphenylmethyloxycarbonyl group, and the like may be included, however, it is not limited thereto. As an alkylcarbonyloxy group having carbon atoms of 2 to 20 which may be substituted, acetyloxy group, ethylcarbonyloxy group, n-propylcarbonyloxy group, iso-propylcarbonyloxy group, n-butylcarbonyloxy group, iso-butylcarbonyloxy group, sec-butylcarbonyloxy group, t-butylcarbonyloxy group, n-pentylcarbonyloxy group, n-hexylcarbonyloxy group, cyclohexylcarbonyloxy group, n-heptylcarbonyloxy group, 3-heptylcarbonyloxy group, n-octylcarbonyloxy group, and the like may be included, however, it is not limited thereto. As an arylcarbonyloxy group having carbon atoms of 7 to 20 which may be substituted, benzoyloxy group, and the like may be included, however, it is not limited thereto. As an aralkylcarbonyloxy group having carbon atoms of 8 to 20 which may be substituted, benzylcarbonyloxy group, and the like may be included, however, it is not limited thereto. As a heterocyclic group having carbon atoms of 2 to 20 which may be substituted, pyrrole group imidazole group, piperidine group, morpholine group, and the like may be included, however, it is not limited thereto.

As a substituent which may be present, if necessary, at a functional group $B^1$ to $B^{24}$ in the formula (Y), namely, alkyl group, alkoxy group, aryl group, aryloxy group, aralkyl group, aralkyloxy group, alkylthio group, arylthio group, aralkylthio group, alkylsulfonyl group, arylsulfonyl group, aralkylsulfonyl group, acyl group, alkoxycarbonyl group, aryloxycarbonyl group, aralkyloxycarbonyl group, alkylcarbonyloxy group, arylcarbonyloxy group, aralkylcarbonyloxy group and heterocyclic group, for example, halogen atom, acyl group, alkyl group, phenyl group, alkoxy group, halogenated alkyl group, halogenated alkoxy group, nitro group, amino group, alkylamino group, alkylcarbonylamino group, arylamino group arylcarbonylamino group, carbonyl group, alkoxycarbonyl group, alkylaminocarbonyl group, alkoxysulfonyl group, alkylthio group, carbamoyl group, aryloxycarbonyl group, cyano group, heterocyclic group, and the like may be included, however, it is not limited thereto. These substituents may be present in plural and when they are present in plural, they may be the same or different each other, and even in the case of the same kind, they may be the same or different, and functional groups themselves may be bonded together via a linking group.

(In the Case when the Terminal is a Functional Group of an Amino Group)

As a substituent to a functional group $B^1$ to $B^{24}$ in the formula (Y), namely, an amino group which may be substituted, an aminosulfonyl group which may be substituted and an aminocarbonyl group which may be substituted, hydrogen atom; a linear, branched, or cyclic alkyl group such as methyl group, ethyl group, n-propyl group, n-butyl group, sec-butyl group, n-pentyl group, n-hexyl group, 2-ethylhexyl group and cyclohexyl group; an aryl group such as phenyl group and naphthyl group; an aralkyl group such as benzyl group, phenethyl group; a linear, branched, or cyclic alkylcarbonyl group such as acetyl group, ethylcarbonyl group, n-propylcarbonyl group, iso-propylcarbonyl group, n-butylcarbonyl group, iso-butylcarbonyl group, sec-butylcarbonyl group, t-butylcarbonyl group, n-pentylcarbonyl group, n-hexylcarbonyl group, cyclohexylcarbonyl group, n-heptylcarbonyl group, 3-heptylcarbonyl group and n-octylcarbonyl group; an arylcarbonyl group such as benzoyl group and naphthylcarbonyl group; an aralkylcarbonyl group such as benzylcarbonyl group, and the like may be included, however, it is not limited thereto and these substituents may further be substituted with substituents. These substituents may be present in 0, one or two, and when two substituents are present, they may be the same or different each other, and even in the case of the same kind, they may be the same or different, and functional groups themselves may be bonded together via a linking group.

As substituents which may further be present at alkyl group, aryl group, aralkyl group, alkylcarbonyl group, arylcarbonyl group, aralkylcarbonyl group, and the like, which are substituents to the amino group which my be substituted, aminosulfonyl group which may be substituted and an aminocarbonyl which may be substituted, for example, halogen atom, acyl group, alkyl group, phenyl group, alkoxy group, halogenated alkyl group, halogenated alkoxy group, nitro group, amino group, alkylamino group, alkylcarbonylamino group, arylamino group, arylcarbonylamino group, carbonyl group, alkoxycarbonyl group, alkylaminocarbonyl group, alkoxysulfonyl group, alkylthio group, carbamoyl group, aryloxycarbonyl group, cyano group and heterocyclic group may be included, however, it is not limited thereto. These substituents may be present in 0, one or two and when they are present in plural, they may be the same or different each other, and even in the case of the same kind, they may be the same or different and functional groups themselves may be bonded together via a linking group.

In addition, as an example of a bivalent metal as metal $M^2$, Cu(II), Co(II), Zn(II), Fe(II), Ni(II), Ru(II), Rh(II), Pd(II), Pt(II), Mn(II), Mg(II), Ti(II), Be(II), Ca(II), Ba(II), Cd(II), Hg(II), Pb(II), Sn(II), and the like may be included, however, it is not limited thereto. As an example of a trivalent substituted metal atom, such as Al—F, Al—Cl, Al—Br, Al—I, Fe—Cl, Ga—F, Ga—Cl, Ga—I, Ga—Br, In—F, In—Cl, In—Br, In—I, Tl—F, Tl—Cl, Tl—Br, Tl—I, Al—$C_6H_5$, Al—$C_6H_4(CH_3)$ In—$C_6H_5$, In—$C_6H_4(CH_3)$, In—$C_6H_5$, Mn(OH), Mn($OC_6H_5$), Mn[$OSi(CH_3)_3$], Ru—Cl, and the like may be included, however, it is not limited thereto. As an example of a tetravalent substituted metal atom, $CrCl_2$, $SiF_2$, $SiCl_2$, $SiBr_2$, $SiI_2$, $ZrCl_2$, $GeF_2$, $GeCl_2$, $GeBr_2$, $GeI_2$, $SnF_2$, $SnCl_2$, $SnBr_2$, $TiF_2$, $TiCl_2$, $TiBr_2$, $Ge(OH)_2$, $Mn(OH)_2$, $Si(OH)_2$, $Sn(OH)_2$, $Zr(OH)_2$, $Cr(R_1)_2$, $Ge(R_1)_2$, $Si(R_1)_2$, $Sn(R_1)_2$, $Ti(R_1)_2$ {$R_1$ represents alkyl group, phenyl group, naphthyl group, and derivatives thereof}, $Cr(OR_2)_2$, $Ge(OR_2)_2$, $Si(OR_2)_2$, $Sn(OR_2)_2$, $Ti(OR_2)_2$ {$R_2$ represents alkyl group, phenyl group, naphthyl group, trialkylsilyl group, dialkylalkoxysilyl group and derivatives thereof}, $Sn(SR_3)_2$, $Ge(SR_3)_2$ {$R_3$ represents alkyl group, phenyl group, naphthyl group, or derivatives thereof}, and the like may be included, however, it is not limited thereto. As an example of an oxymetal, VO, MnO, TiO, and the like may be included, however, it is not limited thereto.

Specifically, trade names of EXCOLOR IR-10A, EXCOLOR IR-12 and EXCOLOR IR-14 or TX-EX-906B, TX-EX-910B and TX-EX-902K (all produced from Nippon Shokubai Co., Ltd.) may be included.

The amount of a near-infrared ray absorbing dye to be formulated in near-infrared ray absorption material of the present invention can be selected, as appropriate, depending on applications. It may be in the range of 0.1 to 10% by weight based on solid content of a resin and preferably 1 to 8% by weight. In this case, amount to be compounded of an ionic near-infrared ray absorbing dye below 0.1% by weight is too low amount to be compounded of a dye and attainment of sufficient near-infrared ray absorption ability may be impossible. On the contrary, the amount over 10% by weight does not provide effects comparable to the addition and thus not economical, and moreover transparency in visible region may be lost on the contrary.

(4) Resin

The near-infrared ray absorption material of the present invention may further contain a resin. The resin which can be used in the present invention is not especially limited, so long as it is a resin generally usable as optical material. A resin with transparency as high as possible is preferable, and more specifically, polyolefin-based resins such as polyethylene, polypropylene, carboxylated polyolefin, chlorinated polyolefin and cycloolefin polymer; polystyrene, polyacrylate ester-based polymer, polymethacrylate ester-based polymer; vinyl-based polymers such as polyvinyl acetate, halogenated vinyl polymer and poval; polyamide-based resins such as nylon; polyurethane-based resins; polyester-based resins such as PET (polyethylene terephthalate); polycarbonate; epoxy-based resins; polyvinyl acetal-based resins such as butyral resin, and the like may be included.

Among these, a resin which can be melted or solubilized can be preferably used. In this case, when such a resin is used as being capable of being melted and having high Tg, a near-infrared ray absorption material which can be molded is obtained. For example, a resin which can be melted and having Tg not lower than 80° C. can provide a moldable material by formulating a near-infrared ray absorbing dye therein. Suitable examples of the resin include methacrylate polymer such as polymethyl methacrylate, copolymer of α-hydroxymethyl acrylate, polycarbonate, butyral resin, cyclopolyolefin polymer, ARTON (produced from JSR Corp.), Zeonor (produced from Zeon Corp.), O-PET (produced from Kanebo, Ltd.), Sumipex (produced from Sumitomo Chemical Co., Ltd.), Optorez (produced from Hitachi Chemical Co., Ltd.).

A resin which can be solubilized can provide a coating material by solubilizing a near-infrared ray absorption material therewith. Suitable examples of the resin for coating material include methacrylate ester-based polymers, ARTON (produced from JSR Corp.), Zeonor (produced from Zeon Corp.) and O-PET (produced from Kanebo, Ltd.). Particularly preferable are polymers obtained by copolymerizing methacrylate ester having a linear, branched, or polyalicyclic alkyl group with carbon atoms of 1 to 10, such as methyl methacrylate, tert-butyl methacrylate, cyclohexyl methacrylate and isobornyl methacrylate. The resin may be a polymer composed of only one kind of a methacrylate ester monomer or a copolymer composed of plurality of methacrylate ester monomers. In addition, it may be a polymer obtained by copolymerizing the methacrylate ester monomer as described above with a monomer other than the monomer. As other monomers, an aromatic monomer such as styrene and methylstyrene; a maleinimide monomer such as phenylmaleinimide and cyclohexylmaleinimide; a carboxyl group containing monomer such as methacrylic acid and acrylic acid; an acrylate ester having carbon atoms of 1 to 15; a monomer having a hydroxyl group such as hydroxyethyl methacrylate and hydroxyethyl acrylate, and the like can also be used. The amount of the monomer other than the methacrylate ester monomer to be used is below 50% by weight, preferably below 30% by weight and further preferably below 10% by weight. Specifically, Sumipex (produced from Sumitomo Chemical Co., Ltd.), Optorez (produced from Hitachi Chemical Co., Ltd.) and HALSHYBRID IR (produced from Nippon Shokubai Co., Ltd.), and the like may be included. A resin having a glass transition temperature (Tg) higher than 85° C. can effectively suppress deterioration of dye caused by heat or moisture.

Although a resin having high Tg has significantly high durability, it has such a defect as of easy cracking when used in film applications. To suppress the cracking of a resin, weight average molecular weight is preferably, as reduced to polystyrene, not smaller than 50,000 and further preferably not smaller than 100,000.

Also to make cracking difficult, a polymer structure is preferably a branched structure rather than a linear one. By taking a branched structure, even when a resin has high molecular weight, viscosity thereof becomes low and handling becomes easy. To obtain a branched polymer, a macromonomer, a multi-functional monomer, a multi-functional initiator and a multi-functional chain transfer agent can be used. As the macromonomer, AA-6, AA-2, AS-6, AB-6, AK-5 (all produced from Toagosei Co. Ltd.), and the like can be used. As the multi-functional monomer, LIGHT-ESTER EG, LIGHT-ESTER 1,4BG, LIGHT-ESTER NP, LIGHT-ESTER TMP (all produced from KYOEISHA CHEMICAL Co., Ltd.) can be used. As the multi-functional initiator, Pertetra A and BTTB-50 (all produced from NOF Corp.), Trigonox 17-40 MB and PERKADOX 12-XL25 (all produced from Kayaku Akuzo Corp.), and the like can be used. As the multi-functional chain transfer agent, pentaerythritol tetrakis(3-mercaptoproionate), trimethylolpropane tris(3-mercaptopropionate), pentaerythritol tetrakis(thioglycolate) (all produced from Sakai Chemical Industry Co., Ltd.), and the like can be used. To obtain a resin with a branched structure, a multi-functional initiator may be particularly preferably used due to easy polymerization. Pertetra A and PERKADOX 12-XL25 which can provide many branches and react under mild conditions may be particularly preferably used.

The near-infrared ray absorption material of the present invention can provide good durability even if Tg is not higher than 85° C. Although the resin is not especially limited in account of its kind, an acrylic resin and a polyester resin can be used. To attain both cracking resistance and high durability, Tg of a resin is preferably in the range of 65 to 85° C., and more preferably 70 to 80° C.

The resin may be a pressure-sensitive adhesive or an adhesive or the mixture thereof. Because the near-infrared ray absorption material using a pressure-sensitive adhesive or an adhesive enables to adhere to other functional films, an optical filter of the present invention can be produced conveniently and economically.

The resin suitable as a pressure-sensitive adhesive includes acrylic-based, silicone-based, SBR-based resins, and the like. Particularly preferable resin includes a polymer obtained by polymerization using ethyl acrylate, butyl acrylate, 2-ethylhexyl acrylate, n-octyl acrylate, and the like, as a main component. More specifically, "ACRYSET AST" (produced from Nippon Shokubai Co., Ltd.) may be cited. Tg is preferably not lower than −80° C. and not higher than 0° C. Furthermore, a advantageously used pressure-sensitive adhesive is acryl-based resin obtained by copolymerizing a (meth)acrylate ester having an alicyclic alkyl group such as cyclohexyl group and isobornyl group. Although the amount of the (meth)acrylate ester having an alicyclic alkyl group to be used in copolymerization thereof is not especially limited, the resin may be preferably used in such an amount as that Tg of resin is fallen in the range of not lower than −80° C. and not higher than 0° C.

It is also possible to copolymerize a (meth)acrylate ester having an acidic group such as a carboxyl group. In this case, aiming at improvement of moisture resistance, the amount of a (meth)acrylate ester to be copolymerized may be such that an acid value of the resin is preferably fallen in the range of not higher than 30, more preferably not higher than 15 and most preferably not higher than 5. In the present specification, "acid value" means an amount of potassium hydroxide in mg, required to neutralize 1 g (solid content) of a resin.

As a resin suitable as an adhesive, generally used silicone-based, urethane-based, acryl-based resins and polyolefin-based resins such as an ethylene-vinyl acetate copolymer, a carboxylated polyolefin, a chlorinated polyolefin, and the like may be included.

When a pressure-sensitive adhesive or an adhesive is used as a resin, it is preferable to use a salt containing anilinium, pyridinium and quinolinium cation as a salt containing an anion of the formula (1). As a near-infrared ray absorbing dye, it is preferable to use a diimmonium dye having a tetrakis (pentfluorophenyl)borate anion as a counter anion.

The amount of a resin to be formulated in the near-infrared ray absorption material of the present invention can be suitably selected, depending on applications and an amount of a dye or a solvent.

(5) Additive

The near-infrared ray absorption material of the present invention may be added with a dye showing maximal absorption wavelength in visible region of 380 to 780 nm wavelength. As such a dye, a conventionally known dye such as cyanin-based, tetraazaporphyrin-based, azulenium-based, squarylium-based, diphenylmethane-based, triphenylmethane-based, oxazine-based, azine-based, thiopyrylium-based, viologen-based, azo-based, azo-metal complex-based, bis-azo-based, anthraquinone-based, perylene-based, indanthrone-based, nitroso-based, metal-thiol complex-based, indigo-based, azomethine-based, xanthene-based, oxanol-based, indoaniline-based and quinoline-based dye can widely be used. For example, trade names of ADEKA ARKLES TW-1367, ADEKA ARKLES SG-1574, ADEKA ARKLES TW-1317, ADEKA ARKLES FD-3351, ADEKA ARKLES Y944, all produced from Asahi Denka Co. Ltd.; and trade names of NK-5451, NK-5532 and NK-5450, all produced from HAYASHIBARA BIOCHEMICAL LAB., INC., may be included.

The amount of the dye to be formulated in the near-infrared ray absorption material of the present invention can be suitably selected, depending on applications, and may be in the range of 0.1 to 10% by weight, preferably 1 to 8% by weight, based on a solid content of a resin.

Furthermore, into the near-infrared ray absorption material of the present invention, an isocyanate compound, a thiol compound, an epoxy compound, an amine-based compound, an imine-based compound, an oxazoline compound, a silane coupling agent, and a resin curing agent such as a UV curing agent may also be used in an amount so as not to impair performance thereof. However, a near-infrared ray absorption material without using a curing agent is more preferable because of providing longer pot-life of a coating solution and no requirement of aging.

In addition, into the near-infrared ray absorption material of the present invention, well-known additives used in a film or a coating agent can be used, including a dispersing agent, a leveling agent, an antifoaming agent, a viscosity modifier, a matting agent, a tackifier, an antistatic agent, an antioxidant, a UV absorbing agent, a light stabilizer, a quencher, a curing agent, an antiblocking agent, a slipping agent, and the like.

(6) Form of Near-Infrared Ray Absorption Material

The near-infrared ray absorption material of the present invention may be in a form of mixing an anion salt of the formula (1) and another compound, each in solid (for example, powder and pellet) form. In the case of a mixture with a resin which can be melted, the mixture can be processed into an arbitrary shape by heating at a temperature of not lower than melting temperature. For processing, a press machine or an extrusion molding machine can be used.

In the case of forming a near-infrared ray absorption layer on a substrate by a coating method, it is preferable to use a solvent to dissolve, disperse and suspend a near-infrared ray absorption material to make a liquid state. As the solvent which can be used in this case, for example, an aliphatic solvent such as cyclohexane and methylcyclohexane; an aromatic solvent such as toluene and xylene; a ketone-based solvent such as acetone, methyl ethyl ketone and methyl isobutyl ketone; an ester-based solvent such as ethyl acetate and butyl acetate; a nitrile-based solvent such as acetonitrile; an alcohol-based solvent such as methanol, ethanol and isopropyl alcohol; an ether-based solvent such as tetrahydrofuran and dibutyl ether; a glycol ether-based solvent such as butylcellosolve, propylene glycol n-propylether, propylene glycol n-butyl ether and propylene glycol monomethyl ether acetate; an amide-based solvent such as formamide and N,N-dimethylformamide; a halogen-based solvent such as methylene chloride and chloroform can be used. They may be used singly or in a mixed form. To improve durability of a dye, a solvent having a boiling point of not higher than 100° C., such as methyl ethyl ketone and ethyl acetate can be advantageously used. In addition, to improve appearance of coated film on coating, a solvent having a boiling point of 100 to 150° C., such as toluene, methyl isobutyl ketone and butyl acetate can be advantageously used. To improve cracking resistance of coated film, a solvent having a boiling point of 150 to 200° C., such as butylcellosolve, propylene glycol n-propylether, propylene glycol n-butyl ether and propylene glycol monomethyl ether acetate can be advantageously used.

The near-infrared ray absorption substrate of the present invention can be used as a film or sheet for optical, agriculture, construction, vehicle and image recording applications, a show case for a freezer and refrigerator, a solar cell such as a dye-sensitive type solar cell, photosensitive material using semiconductor laser light as light source, information recording material such as for an optical disk, asthenopia prevention material, photothermal conversion material such as photosensitive paper and adhesive. In particular, such a use is preferable as an optical film or sheet for such as PDP and CD, information recording material for such as an optical disk, photothermal conversion material such as photosensitive paper and pressure-sensitive adhesive/adhesive.

(7) Near-Infrared Ray Absorption Substrate (Film and Laminated Film Form)

The third aspect of the present invention relates to a near-infrared ray absorption substrate containing the near-infrared ray absorption material of the present invention. The near-infrared ray absorption substrate of the present invention may be obtained by forming the near-infrared ray absorption material into a film or by laminating a coating film containing the near-infrared ray absorption material on a transparent substrate.

The transparent substrate is not especially limited, so long as it can be used generally as an optical substance and substantially transparent. As a specific example, glass; olefin polymers such as cyclopolyolefin, amorphous cyclopolyolefin polymer; methacrylic polymer such as polymethyl methacrylate; vinyl polymer such as vinyl acetate, halogenated vinyl; polyester such as PET; polycarbonate; polyvinyl acetal such as butyral resin; polyaryl ether resin, and the like may be included. Further, the transparent substrate may be subjected to surface treatment by a conventionally known method such as corona discharge treatment, flame treatment, plasma treatment, glow discharge treatment, surface roughening treatment and chemical treatment, or coating of an anchor coating agent or a primer. In addition, the substrate resin may be incorporated with a well-known additive, heat-resistant and anti-aging agent, slipping agent, and antistatic agent. By using a well-known method such as injection molding, T die molding, calendar molding and compression molding or a casting method by dissolving in an organic solvent, it can be molded into a film or sheet shape. A substrate composing such a transparent substrate may be unstretched or stretched, or may be laminated with other substrates.

A transparent substrate used for obtaining a near-infrared ray absorbing film by a coating method, a PET film may be preferably used, in particular, an easy adhesion type PET film may be advantageously used. Specifically, COSMOSHINE A4300 (produced from Toyobo, Ltd.), Lumirror U34 (produced from Toray Ind. Inc.) and Melinex 705 (produced from Teijin DuPont Films Japan Ltd.), and the like may be included. In addition, functional films such as TAC (triacetylcellulose) film, antireflection film, antiglare film, impact absorbing film, electromagnetic interference shielding film and UV ray absorbing film, and the like can also be used. By using these, an optical filter for a plasma display or an optical semiconductor element can be produced conveniently. Use of a film is preferable.

Among these, glass, PET film, easy adhesion type PET film, TAC film, antireflection film and electromagnetic interference shielding film are suitably used as a transparent substrate.

In the case when an inorganic substrate such as glass is used as a transparent substrate, a substrate with low content of alkali components may be preferably used, in view of durability of a near-infrared ray absorbing dye. As near-infrared ray absorption material, when a substrate with high content of alkali components such as soda lime glass is used, it is preferable to use a salt having a cation such as anilinium, pyridinium and quinolinium in a salt containing an anion of the formula (1). In addition, as a near-infrared ray absorbing dye, it is preferable to use a diimmonium dye having a tetrakis(pentafluorophenyl)borate anion as a counter anion.

The thickness of a near-infrared ray absorption substrate of the present invention is generally in the approximate range of 0.1 μm to 10 mm. However, it can be determined, as appropriate, depending on objectives. The content of a near-infrared ray absorbing dye contained in a near-infrared ray absorption substrate can be also determined, as appropriate, depending on objectives.

A method for producing the near-infrared ray absorption substrate of the present invention is not especially limited and, for example, the following methods can be utilized. For example, (a) a method for producing a resin plate or film by mixing the near-infrared ray absorption material of the present invention into a resin, and subsequently heating and molding the mixture; (b) a method for producing a resin plate or film by cast polymerization of the near-infrared ray absorption material of the present invention and a monomer or an oligomer, in the presence of a polymerization catalyst; (c) a method for coating the near-infrared ray absorption material of the present invention onto the transparent substrate; (d) a method for coating the near-infrared ray absorption material of the present invention onto a releasable substrate and subsequently disposing the coating on the transparent substrate; (e) a method for coating the near-infrared ray absorption material of the present invention onto a transparent substrate and subsequently disposing the coating on another transparent substrate and curing the laminate may be included.

As the production method (a), although molding temperature and film-forming (resin plate-making) conditions may be somewhat varied depending on the kind of the resin used, usually such a method may be included which comprises adding the near-infrared ray absorption material of the present invention to a powder or pellet of a resin, heating the mixture at 150 to 350° C. to solubilize and molding the liquid to produce a resin plate or make a film by an extruder (make a resin plate).

In the production method (b) by cast polymerization of the near-infrared ray absorption material of the present invention and a monomer or an oligomer in the presence of a polymerization catalyst, the mixture may be charged in a mold and then subjected to a curing reaction, or the mixture may be flowed in a mold and then subjected to solidification till a hard product is obtained. Many resins are moldable by this process and specific examples of such a resin include acrylic resin, diethylene glycol bis(allylcarbonate) resin, epoxy resin, phenol-formaldehyde resin, polystyrene resin, silicone resin, and the like. Among these, a casting method by means of bulk polymerization of methyl methacrylate is preferable, which can provide an acrylic resin sheet superior in hardness, heat resistance and chemical resistance.

As the polymerization catalyst, a well-known initiator for radical thermal polymerization can be utilized, for example, a peroxide such as benzoyl peroxide, p-chlorobenzoyl peroxide and diisopropyl peroxycarbonate, and an azo compound such as azobisisobutylonitrile may be included. The amount to be used is generally in the range of 0.01 to 5% by weight based on total amount of the mixture. The heating temperature on thermal polymerization is generally in the range of 40 to 200° C. and the polymerization time is generally in the approximate range of 30 minutes to 8 hours. In addition to the thermal polymerization, a method for photo polymerization by means of the addition of a photo polymerization initiator or a sensitizer can also be utilized.

As the production method (c), a method for coating the near-infrared ray absorption material of the present invention onto a transparent substrate, a method for fixing the near-infrared ray absorption material of the present invention onto fine particles and then applying a coating material having the fine particles dispersed therein onto the transparent substrate, and the like may be included.

In the case of coating the near-infrared ray absorption material on a substrate, a well-known coater can be used. For example, knife coater such as comma coater, slot die coater, fountain coater such as lip coater, kiss coater such as microgravure coater, gravure coater, roll coater such as reverse coater, flow coater, spray coater, bar coater, and the like may be included. Before coating, a substrate may be subjected to surface treatment by a well-know method such as corona discharge treatment and plasma treatment. As drying and curing methods, well-known methods such as hot air, far infrared ray and UV curing can be used. After drying and curing, a film may be wound with a well-known protective film.

As the production method (d), a method for coating the near-infrared ray absorption material of the present invention onto a releasable substrate and subsequently disposing the coating on a transparent substrate, and a method for fixing the near-infrared ray absorption material of the present invention onto fine particles, and subsequently applying a coating material having the fine particles dispersed therein onto a releasable substrate and disposing the applied substrate onto the transparent substrate, and the like may be included.

In the case of producing by this method, it is preferable to use the near-infrared ray absorption material with a pressure-sensitive adhesive as a resin. If necessary, a tackifier and a curing agent may further be incorporated into the near-infrared ray absorption material.

As the releasable substrate, paper or film having a silicone-based, olefin-based, oil-based and fluorine-based releasing agent, and the like coated thereon, fluorine-based substrate and olefin-based substrate can be used. As the transparent substrate and the coater, those described above can be similarly used.

As the production method (e), a method for coating the near-infrared ray absorption material of the present invention onto a transparent substrate, subsequently disposing the coating onto another transparent substrate and curing the laminate, and the like may be included.

In the case of producing by this method, it is preferable to use the near-infrared ray absorption material with a pressure-sensitive adhesive as a resin. If necessary, a curing agent may be incorporated into the near-infrared ray absorption material. As the transparent substrate and the coater, those described above can be similarly used.

Although the amount of the near-infrared ray absorbing dye in the near-infrared ray absorption substrate of the present invention to be added may be varied depending on thickness of a resin plate or a film to be produced, absorption intensity, transmittance of visible light, and the like, in the methods (a) to (e), the near-infrared ray absorption dye of the present invention can be used in an amount generally in the range of 0.01 to 20% by weight, based on weight of a binder resin.

The near-infrared ray absorption material of the present invention can be converted to component material of a superior optical filter having high transparency in visible region and excellent near-infrared ray absorption ability. Because of higher durability, in particular, heat resistance and moisture resistance, comparing with conventional near-infrared ray absorption materials, appearance and near-infrared ray absorption ability can be maintained even over a long period of storage or use. Furthermore, because of easy production of a sheet or a film, it is usable for a plasma display or an optical semiconductor element. In addition, it can also be used for a filter or a film requiring to cut infrared ray, for example, a heat insulation film, sunglasses and optical recording material, and the like.

(8) Optical Filter for a Plasma Display

The near-infrared ray absorption material of the present invention can be advantageously used as an optical filter for a plasma display. Therefore, the fourth aspect of the present invention relates to an optical filter for a plasma display, using the near-infrared ray absorption material of the present invention. Such an optical filter has a total light transmittance in visible region of not lower than 40%, preferably not lower than 50%, further preferably not lower than 60%, and a transmittance of near-infrared ray at a wavelength of 800 to 1000 nm of not higher than 30%, preferably not higher than 15% and further preferably not higher than 5%.

The optical filter of the present invention may be mounted with, in addition to a near-infrared ray absorption layer comprising the near-infrared ray absorption material, electromagnetic interference shielding layer, antireflection layer, glare prevention (antiglare) layer, scratch prevention layer, color adjustment layer, and a supporting substrate such as glass.

Constitution of each layer of the optical filter may arbitrary selected, however, such an optical filter is preferable as has a combination of at least two layers composed of at least one layer of an antireflection layer and an antiglare layer, and a near-infrared ray absorption layer, and an optical filter having at least 3 layers by further combination of an electromagnetic interference shielding layer therewith is more preferable.

An antireflection layer or an antiglare layer may be the most front layer at a human interface side and the combination of a near-infrared ray absorption layer and an electromagnetic interference shielding layer can be arbitrarily selected. In addition, between the 3 layers, other layers such as a scratch prevention layer, a color adjustment layer, an impact absorption layer, a supporting substrate and a transparent substrate may be inserted.

Each layer may be adhered using a pressure-sensitive adhesive or an adhesive, and a near-infrared ray absorption layer itself may act as a pressure-sensitive adhesive or an adhesive. In particular, because the near-infrared ray absorption material of the present invention obtained by being mixed with a pressure-sensitive adhesive or an adhesive having a Tg of not lower than −80° C. and not higher than 0° C., can exhibit excellent adhesion to another transparent substrate, an optical filter for a plasma display of the present invention can easily be produced, by adhesion of other layer, and the like to an antireflection layer, an antiglare layer, an impact absorption layer and an electromagnetic interference shielding layer, via this near-infrared ray absorption material. On the adhesion of each layer, it may be subjected to physical treatment such as corona treatment and plasma treatment, or a well-known highly polar polymer such as polyethyleneimine, oxazoline-based polymer, polyester and cellulose may be used as an anchor coating agent.

To the optical filter for a plasma display, it is preferable to mount an antireflection layer or an antiglare layer at the most front layer at a human interface side, to provide easy-to-see view field.

An antireflection layer can suppress reflection at a surface and thus prevent show up of exterior light such as a fluorescent light to the surface. The antireflection layer mat be made by a thin film of an inorganic substance such as metal oxide, fluoride, silicide, boride, carbide, nitride and sulfide, or by lamination of a resin with different refractive index, such as acrylic resin and a fluorocarbon resin, in a single layer or multiple layers. In the former case, a method for forming an antireflection coating on a transparent substrate using vapor deposition or sputtering method in single layer or multiple layers may be used. In the latter case, a method for applying an antireflection coating onto the surface of a transparent substrate, using knife coater such as comma coater, slot die coater, fountain coater such as lip coater, gravure coater, flow coater, spray coater and bar coater may be used.

An antiglare layer is formed by making an ink from fine powder of silica, a melamine resin, an acrylic resin, and the like, applying the ink onto any of the layers of a filter of the present invention by a conventional coating method, and then thermal curing or photo curing the coating. In addition, a film after antiglare treatment may be adhered onto the filter.

A scratch prevention film can be formed by applying a coating solution obtained by dissolving or dispersing an acrylate such as urethane acrylate, epoxy acrylate and multifunctional acrylate, and a photopolymerization initiator in an organic solution by a conventionally known coating method, onto any of the layers of a filter of the present invention, and then drying and photo curing.

The optical filter having an antireflection layer or an antiglare layer, and a near-infrared ray absorption layer can be obtained by laminating a layer comprising the near-infrared ray absorption substrate of the present invention and onto the back surface of an antireflection layer or an antiglare layer. As a lamination method, the film-like near-infrared ray absorption material of the present invention, and an antireflection layer or an antiglare layer may be adhered each other by a pressure-sensitive adhesive, or a solution of the near-infrared ray absorption material of the present invention may directly be applied on the back surface of an antireflection layer or an antiglare layer. In the case when a near-infrared ray absorption layer is set on the back surface of an antireflection layer or an antiglare layer, it is preferable to use a UV absorbing film as a transparent substrate, to suppress deterioration of a dye by UV ray.

It is preferable to provide an electromagnetic interference shielding layer in an optical filter for a plasma display, so as to remove electromagnetic wave generating from a panel.

As the electromagnetic interference shielding layer, such a film can be used as obtained by patterning a metal mesh on a film by means of technique such as etching or printing, and then smoothing with a resin, or obtained by vapor deposition of metal on a fiber mesh and then embedding in a resin.

An optical filter having two layers of a near-infrared ray absorption layer and an electromagnetic interference shielding layer can be obtained by making a composite between the electromagnetic interference shielding material and the near-infrared ray absorption material. As a method for making such a composite, a film-shaped near-infrared ray absorption material of the present invention and an electromagnetic interference shielding layer may be adhered each other by a pressure-sensitive adhesive, or a solution of the near-infrared ray absorption material of the present invention may directly be applied on the back surface of the electromagnetic interference shielding layer. In addition, the near-infrared ray absorption material can also be used as a resin to smooth a metal mesh on a film. Further, the near-infrared ray absorption material of the present invention can also be used as a resin to embed fiber vapor deposited with metal.

As an optical filter having three layers of a near-infrared ray absorption layer, and an antireflection layer or an antiglare layer, and an electromagnetic interference shielding layer, a filter obtained by adhesion of three pieces including the near-infrared ray absorption layer composed of the near-infrared ray absorption material of the present invention, and the antireflection layer or antiglare layer, and the electromagnetic interference shielding layer can be used. If necessary, a supporting substrate such as glass or a functional film such as a color adjustment film may be adhered.

To simplify production process or film constitution of the optical filter, it is preferable to use a composite film having multifunction. For example, the following optical filters may be used as an optical filter like an optical filter obtained by adhering a composite film containing a near-infrared ray absorption layer, and an antireflection layer or an antiglare layer, to an electromagnetic interference shielding layer using a pressure-sensitive adhesive; or an optical filter obtained by adhering a composite film containing a near-infrared ray absorption layer, and an electromagnetic interference shielding layer, to an antireflection layer or an antiglare layer using a pressure-sensitive adhesive; or an optical filter obtained by adhering a composite film containing an electromagnetic interference shielding layer and an antireflection layer or an antiglare layer, to a near-infrared ray absorption layer using a pressure-sensitive adhesive. As for a composite film containing an electromagnetic interference shielding layer, and an antireflection layer or an antiglare layer, the near-infrared ray absorption material may act as a pressure-sensitive adhesive.

The optical filter for a plasma display of the present invention may be set apart from a display device or may directly be adhered to a display device. In the case when it is set apart from a display device, it is preferable to use glass as a supporting substrate. In the case when it is directly adhered to a display device, an optical filter without using glass is preferable.

(9) Plasma Display

By mounting the optical filter laminated with the near-infrared ray absorption material of the present invention on a plasma display, good picture quality can be maintained for a long time. Therefore, the fifth aspect of the present invention relates to a plasma display using the near-infrared ray absorption material of the present invention, the near-infrared ray absorption substrate of the present invention or an optical filter of the present invention. The plasma display having an optical filter directly adhered to a display device can provide vivid picture quality. When an optical filter is directly adhered, it is preferable to use reinforced glass as glass for a display device, or an optical filter mounted with an impact absorption layer.

As a pressure-sensitive adhesive for the use in adhesion to a display device, rubber such as styrene butadiene rubber, polyisoprene rubber, polyisobutylene rubber, natural rubber, neoprene rubber, chloroprene rubber and butyl rubber; a polyalkyl acrylate such as polymethyl acrylate, polyethyl acrylate and polybutyl acrylate, and the like may be included, and they may be used alone, however, one added with piccolight, polybale, rosin ester, and the like, as a pressure-sensitive adhesive may also be used. In addition, a pressure-sensitive adhesive having impact absorption ability as is shown in JP-A-2004-263084 can be used, however, it is not limited thereto.

The thickness of the pressure-sensitive adhesive layer may be usually in the range of 5 to 2000 μm, and preferably 10 to 1000 μm. It is also permitted that a releasable film is disposed on the surface of a pressure-sensitive adhesive layer, so as to prevent dust from adhesion onto the pressure-sensitive adhesive layer, and to protect the pressure-sensitive adhesive layer till being disposed on the surface of a plasma display. In this case, by forming a part without a pressure-sensitive adhesive layer between a pressure-sensitive adhesive layer and a releasable film at the peripheral part of the filter, or by forming a non-tackfying part by sandwiching a non-sticky film, to provide a peal-starting area, workability on adhesion can be carried out easily.

An impact absorption layer can protect a display device from external impact. It is preferably used for an optical filter without using a supporting substrate. As an impact absorption substance, an ethylene-vinyl acetate copolymer, acrylic polymer, polyvinyl chloride, urethane-based and silicone-based resins, and the like, as shown in JP-A-2004-246365 and JP-A-2004-264416, can be used, however, it is not limited thereto.

EXAMPLES

Now the present invention is explained specifically with reference to Examples, however, these Examples should by no means limit the present invention. As used herein, "part" means "part by weight". The near-infrared ray absorption ability, transparency in visible region and durability were evaluated in accordance with the following methods.

(1) Evaluation of Near-Infrared Ray Absorption Ability (Transmittance of Near-Infrared Ray)

For the measurement of visible-near-infrared spectrum, UV-3100 (produced from Shimadzu Corp.) was used and transmittance at a wavelength of 1090 nm or 835 nm was measured.

(2) Evaluation of Transparency in Visible Region (Transmittance of Visible Light)

For the measurement of total light transmittance, Σ90 system (produced from Nippon Denshoku Industries Co., Ltd.) was used.

(3) Evaluation of Heat Resistance

A test sample was left in an oven at 100° C. for 120 hours to measure transmittance spectrum in visible-near-infrared region and color difference ($L^*a^*b^*$ in 2° view field, C light source) before and after the test. For the measurement of visible-near-infrared spectrum, UV-3100 (produced from Shimadzu Corp.) was used and change in transmittance ($\Delta T$) at a wavelength of 1090 nm or 835 nm was measured. For the measurement of color difference, SE2000 (produced from Nippon Denshoku Industries Co., Ltd.) was used and change in $b^*$ ($\Delta b^*$) was measured.

(4) Evaluation of Moisture Resistance

A test sample was left in a chamber at 80° C. and 95% RH for 120 hours to measure transmittance spectrum in visible-near-infrared region and color difference ($L^*a^*b^*$ in 2° view field, C light source) before and after the test. For the measurement of visible-near-infrared spectrum, UV-3100 (produced from Shimadzu Corp.) was used and change in transmittance ($\Delta T$) at a wavelength of 1090 nm or 835 nm was measured. For measurement of color difference, SE2000 (produced from Nippon Denshoku Industries Co., Ltd) was used and change in $b^*$ ($\Delta b^*$) was measured.

Example 1-1

5 parts of N,N,N',N'-tetrakis(p-di(n-butyl)aminophenyl)-p-phenylene diimmonium hexafluoroantimonate (hereinafter referred to as "diimmonium SbF6 salt") was dissolved into 95 parts of methyl ethyl ketone (hereinafter referred to as "MEK"), to prepare a solution 1 of a near-infrared ray absorbing dye. Then, 5 parts of sodium tetrakis(pentafluorophenyl) borate (TEPBNa, produced from Nippon Shokubai Co., Ltd.) was dissolved into 95 parts of MEK, to prepare a borate solution 1. Subsequently, by using HALSHYBRID IR-G205 (produced from Nippon Shokubai Co., Ltd.: solid content of 29%) as a resin, 69 parts of the resin, 4 parts of the solution 1 of a near-infrared ray absorbing dye, 2 parts of the borate solution 1 and 22 parts of MEK were mixed, to obtain a solution A1 of a near-infrared ray absorption material, having a solid content of coating material of 21% (solid content ratio: resin/dye/borate=100/1/0.5).

Example 1-2

The solution A1 of a near-infrared ray absorption material was applied on an easy adhesion type PET film (COSMOSHINE A4300, produced from Toyobo, Ltd.) using a bar coater (No. 34) and then dried in a hot air dryer at 150° C. for 3 minutes, to obtain a near-infrared ray absorption substrate A1. The near-infrared ray absorption substrate A1 was evaluated for transmittance of near-infrared ray, total light transmittance and heat resistance and the results are shown in Table 1. In this case, the transmittance of near-infrared ray was determined at a wavelength of 1090 nm.

Example 2-1

Using HALSHYBRID IR-G205 (produced from Nippon Shokubai Co., Ltd.: solid content of 29%) as a resin, 69 parts of the resin, 4 parts of the solution 1 of a near-infrared ray absorbing dye, 8 parts of the borate solution 1 obtained in Example 1-1 and 17 parts of MEK were mixed, to obtain a solution A2 of a near-infrared ray absorption material, having a solid content of coating material of 21% (solid content ratio: resin/dye/borate=100/1/2).

Example 2-2

The solution A2 of a near-infrared ray absorption material was applied and then dried similarly as in Example 1-2, to obtain a near-infrared ray absorption substrate A2. The near-infrared ray absorption substrate A2 was evaluated for transmittance of near-infrared ray, total light transmittance and heat resistance by using the same method as in Example 1-2, and the results are shown in Table 1.

Comparative Example 1-1

Using HALSHYBRID IR-G205 (produced from Nippon Shokubai Co., Ltd.: solid content of 29%) as a binder, 69 parts of the binder, 4 parts of the solution 1 of a near-infrared ray absorbing dye and 23 parts of MEK were mixed, to obtain a solution B1 of a near-infrared ray absorption material, having a solid content of coating material of 21% (solid content ratio: resin/dye/borate=100/1/0).

Comparative Example 1-2

The solution B1 of a near-infrared ray absorption material was applied and then dried similarly as in Example 1-2, to obtain a near-infrared ray absorption substrate B1. The near-infrared ray absorption substrate B1 was evaluated for transmittance of near-infrared ray, total light transmittance and heat resistance by using the same method as in Example 1-2, and the results are shown in Table 1.

TABLE 1

|  | Resin (Solid content ratio) | Dye (Solid content ratio) | Borate (Solid content ratio) | Near-infrared ray transmittance (%) | Total light transmittance (%) | Heat resistance ΔT (%) | Heat resistance Δb* |
|---|---|---|---|---|---|---|---|
| Example 1-2 (A1) | X1 100 | Y1 1.0 | Z1 0.5 | 29.6 | 88.7 | 3.1 | 0.9 |
| Example 2-2 (A2) | X1 100 | Y1 1.0 | Z1 2.0 | 32.0 | 88.7 | 1.2 | 0.5 |
| Comp. Examp. 1-2 (B1) | X1 100 | Y1 1.0 | None — | 29.3 | 88.3 | 7.0 | 0.9 |

X1: HALSHYBRID IR-G205 (produced from Nippon Shokubai Co., Ltd.)
Y1: N,N,N',N'-tetrakis(p-di(n-butyl)aminophenyl)-p-phenylene diimmonium hexafluoroantimonate,
Z1: Sodium tetrakis(pentafluorophenyl)borate It is noted from the results shown in the Table 1 that while the near-infrared ray absorption substrates A1 and A2 of the present invention, comparing with the near-infrared ray absorption substrate B1 wherein the borate of the present invention was not used, have equivalent transmittance of near-infrared ray and total light transmittance, change in optical characteristics (change in transmittance) at 100° C. after 120 hours is significantly smaller in the near-infrared ray absorption substrates A1 and A2 of the present invention than the near-infrared ray absorption substrate B1, indicating that the near-infrared ray absorption material of the present invention is difficult to be deteriorated.

Example 3-1

1.05 parts of sodium tetrakis(pentafluorophenyl)borate (TEPBNa, produced from Nippon Shokubai Co., Ltd.) and 0.70 part of a diimmonium SbF6 salt were dissolved into 10 parts of methyl ethyl ketone (MEK) at 25° C. Subsequently, whole amount of the resultant solution was collectively added into 500 parts of deionized water and left standing at 25° C. for 1 hour. A precipitate was recovered by filtration and dried at 80° C., to obtain 0.83 part of a black solid.

The resultant black solid was dissolved in MEK and subjected to elemental analysis with fluorescent X-ray spectrum, to find that antimony was not detected. In addition, F-NMR measured by dissolving in deuterated dimethyl sulfoxide (DMSO) showed a peak coincident with a peak of TEPB but no peaks derived from SbF6 were detected. In addition, visible-near-infrared absorbing spectrum measured by dissolving in MEK was coincident with spectrum of a diimmonium dye as a raw material, and thus it was confirmed that a diimmonium structure was maintained.

Figure 2:
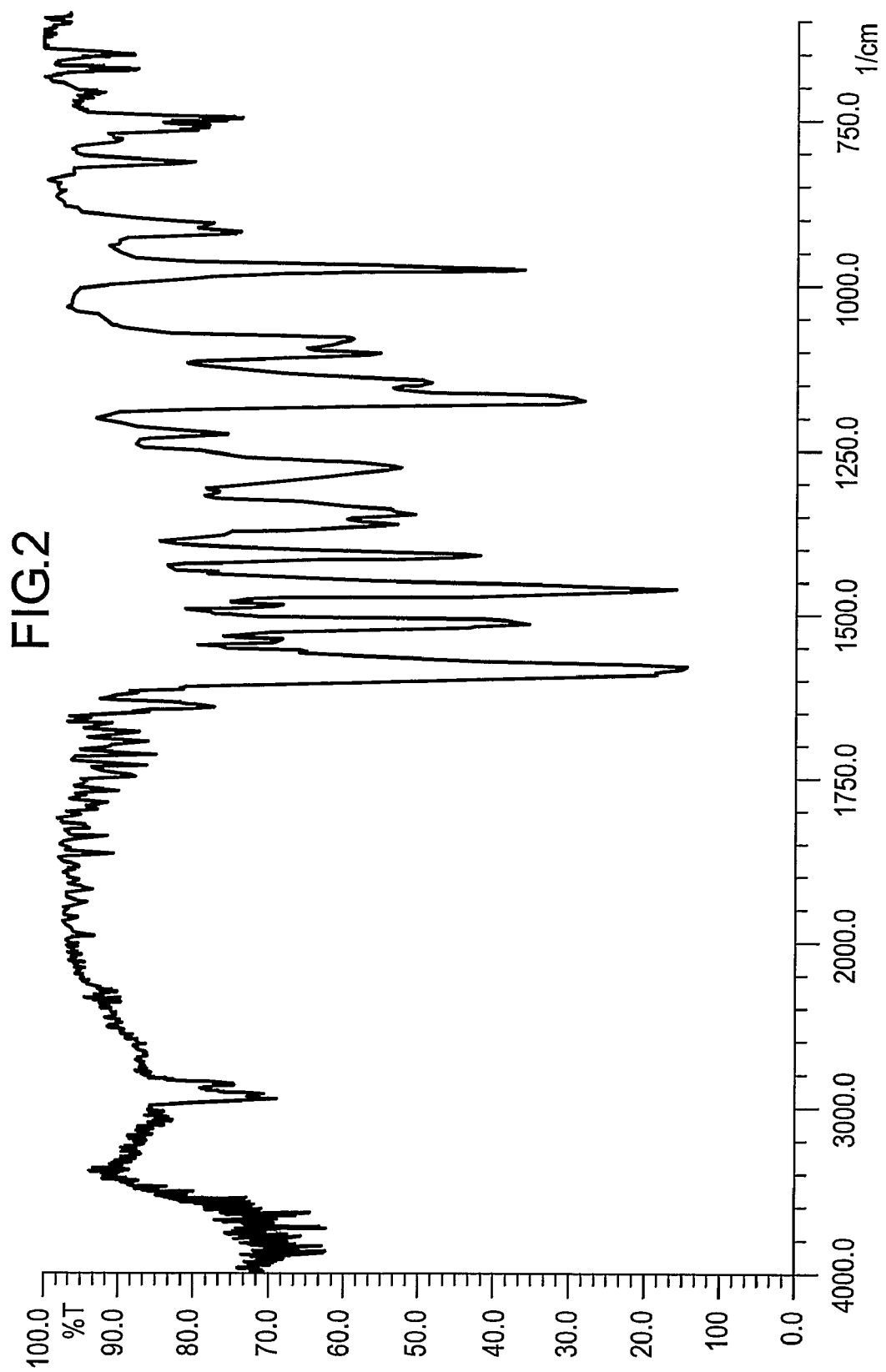
FIG. 2 is an IR spectrum of a diimmonium TEPB salt obtained in Example 3-1.

From the above results, it was confirmed that the black solid was tetrakis(pentafluorophenyl)borate of diimmonium as the raw material (hereinafter referred to as "diimmonium TEPB salt"). Visible-near-infrared absorbing spectrum of the diimmonium TEPB salt is shown in FIG. 1 and IR spectrum of the diimmonium TEPB salt measured by a KBr method is shown in FIG. 2.

Example 3-2

By dissolving 2 parts of a diimmonium TEPB salt into 98 parts of MEK, a solution 2 of a near-infrared ray absorbing dye was prepared. Using HALSHYBRID IR-G205 (produced from Nippon Shokubai Co., Ltd.: solid content of 29%) as a binder, 69 parts of the binder, 17 parts of the solution 2 of a near-infrared ray absorbing dye, 11 parts of MEK were mixed, to obtain a solution A3 of a near-infrared ray absorption material having a solid content of coating material of 21% (solid content ratio: resin/dye/borate=100/1.7/0.0).

Example 3-3

The solution A3 of a near-infrared ray absorption material was applied and dried similarly as in Example 1-2, to obtain a near-infrared ray absorption substrate A3. The near-infrared ray absorption substrate A3 was evaluated by using the same method as in Example 1-2, and the results are shown in Table 2.

Comparative Example 2-1

Figure 3:
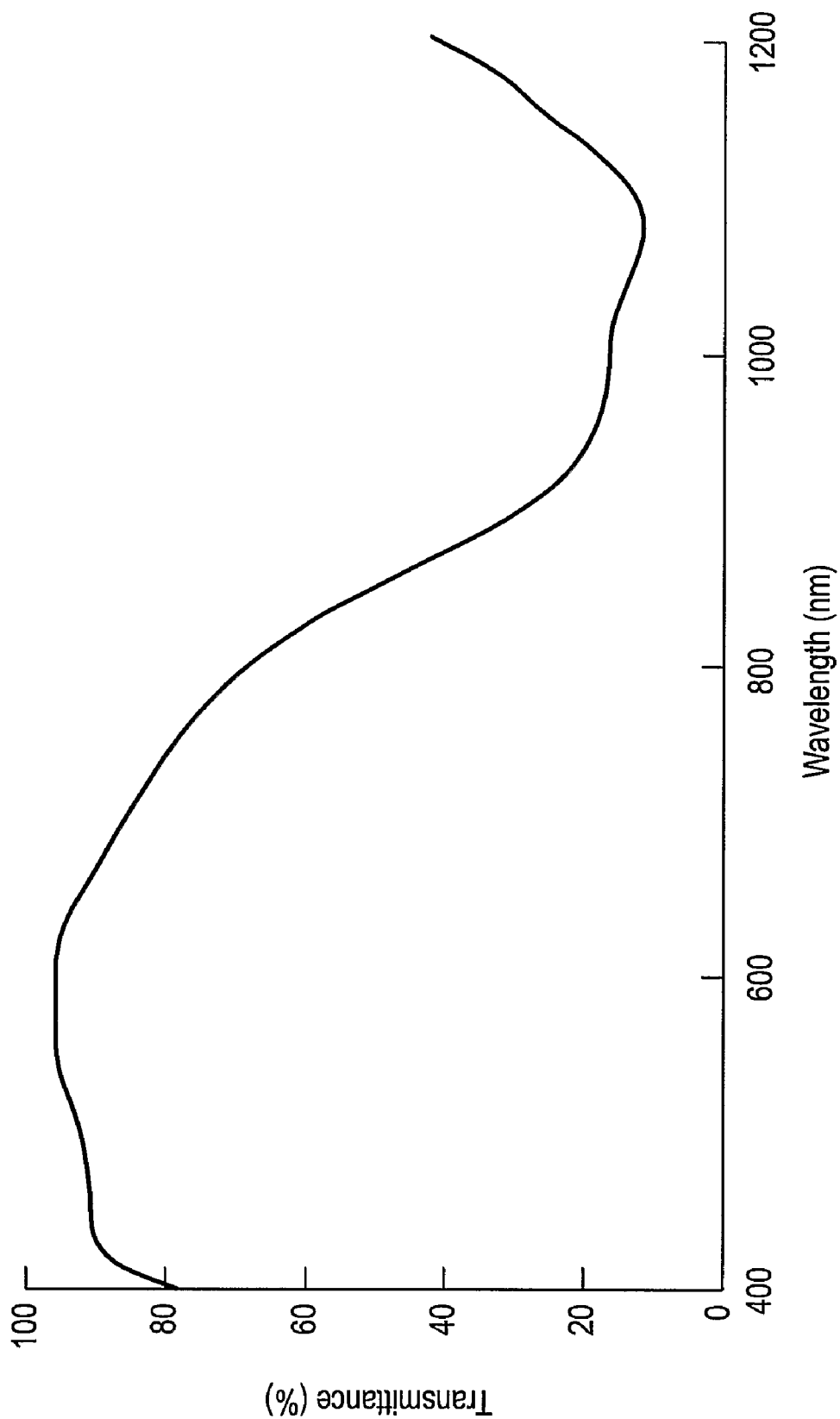
FIG. 3 is a visible-near-infrared absorbing spectrum of a diimmonium SbF6 salt used in Comparative Example 2-1.
Figure 4:
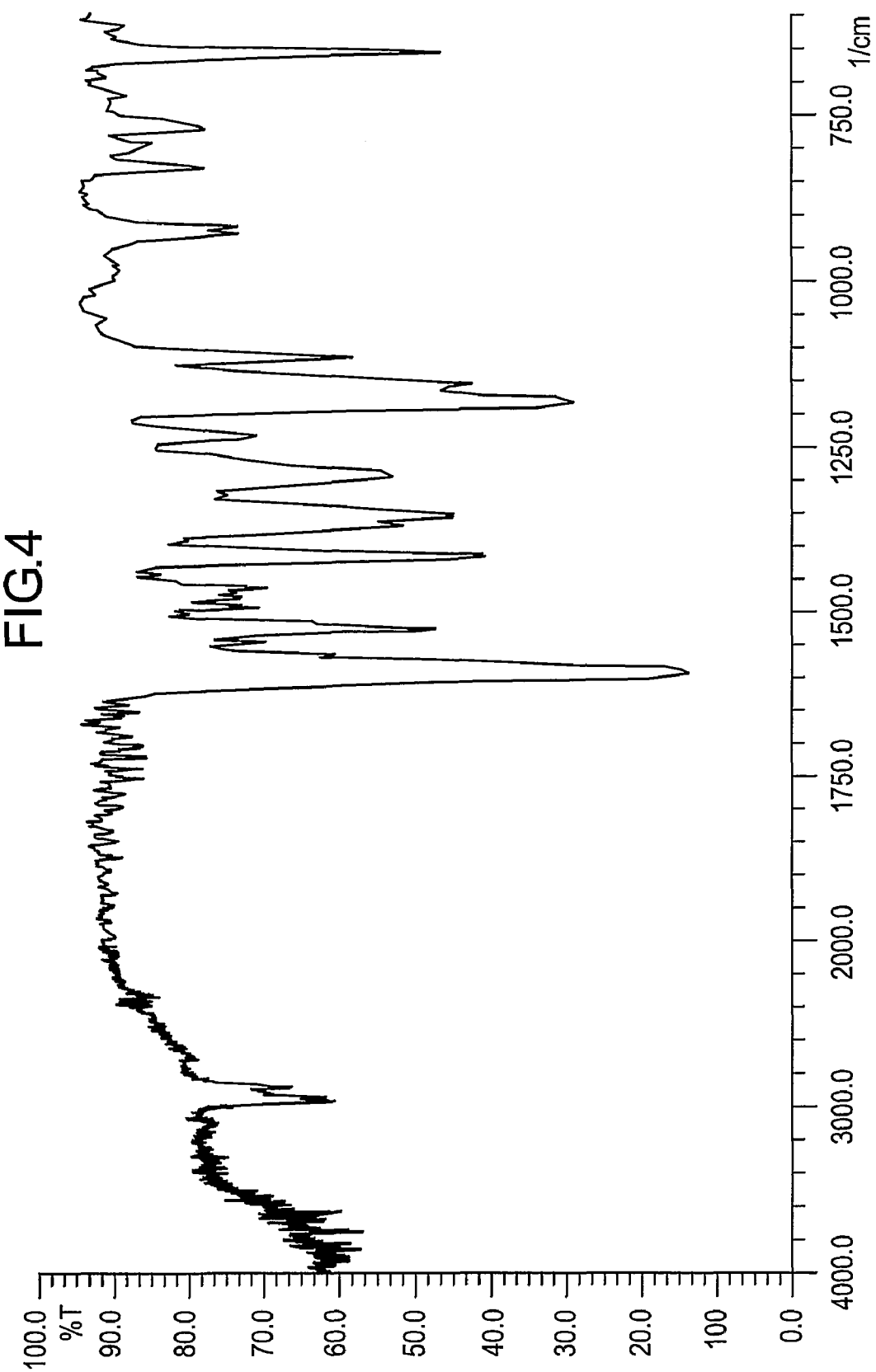
FIG. 4 is an IR spectrum of a diimmonium SbF6 salt used in Comparative Example 2-1.

A diimmonium SbF6 salt was used. Visible-near-infrared absorbing spectrum of the diimmonium SbF6 salt measured in a MEK solution is shown in FIG. 3 and IR spectrum of the diimmonium SbF6 salt measured by a KBr method is shown in FIG. 4.

Comparative Example 2-2

By dissolving 2 parts of a diimmonium SbF6 salt into 98 parts of MEK, a solution 3 of a near-infrared ray absorbing dye was prepared. Using HALSHYBRID IR-G205 (produced from Nippon Shokubai Co., Ltd.: solid content of 29%) as a binder, 69 parts of the binder, 10 parts of the solution 3 of a near-infrared ray absorbing dye, 17 parts of MEK were mixed, to obtain a solution B2 of a near-infrared ray absorption material having solid content of coating material of 21% (solid content ratio: resin/dye/borate=100/1.0/0.0).

Comparative Example 2-3

The solution B2 of a near-infrared ray absorption material was applied and dried similarly as in Example 1-2, to obtain a near-infrared ray absorption substrate B2. The near-infrared ray absorption substrate B2 was evaluated by using the same method as in Example 1-2, and the results are shown in Table 2.

Comparative Example 3-1

0.51 part of sodium tetraphenylborate (produced from Dojindo Lab. under the name of Kalibor) and 0.70 part of a diimmonium SbF6 salt were dissolved into 10 parts of MEK at 25° C. and left standing, to generate a precipitate. While washing the solution and the precipitate with 5 parts of MEK, whole amount of the solution was collectively added into 500 parts of deionized water and left standing at 25° C. for 1 hour. The precipitate was recovered by filtration and dried in vacuum at room temperature, to obtain 0.83 part of a red brown solid.

The resultant red brown solid was dissolved in MEK and subjected to elemental analysis with fluorescent X-ray spectrum, to find that antimony was not detected. In addition, mass spectrum of an anion showed a peak derived from tetraphenylborate. In addition, when the solid was dissolved in MEK, color of the solution gradually changed to green and visible-near-infrared absorbing spectrum was found to show larger absorption in visible range and smaller absorption in near-infrared region than the diimmonium SbF6 salt as the raw material.

Figure 5:
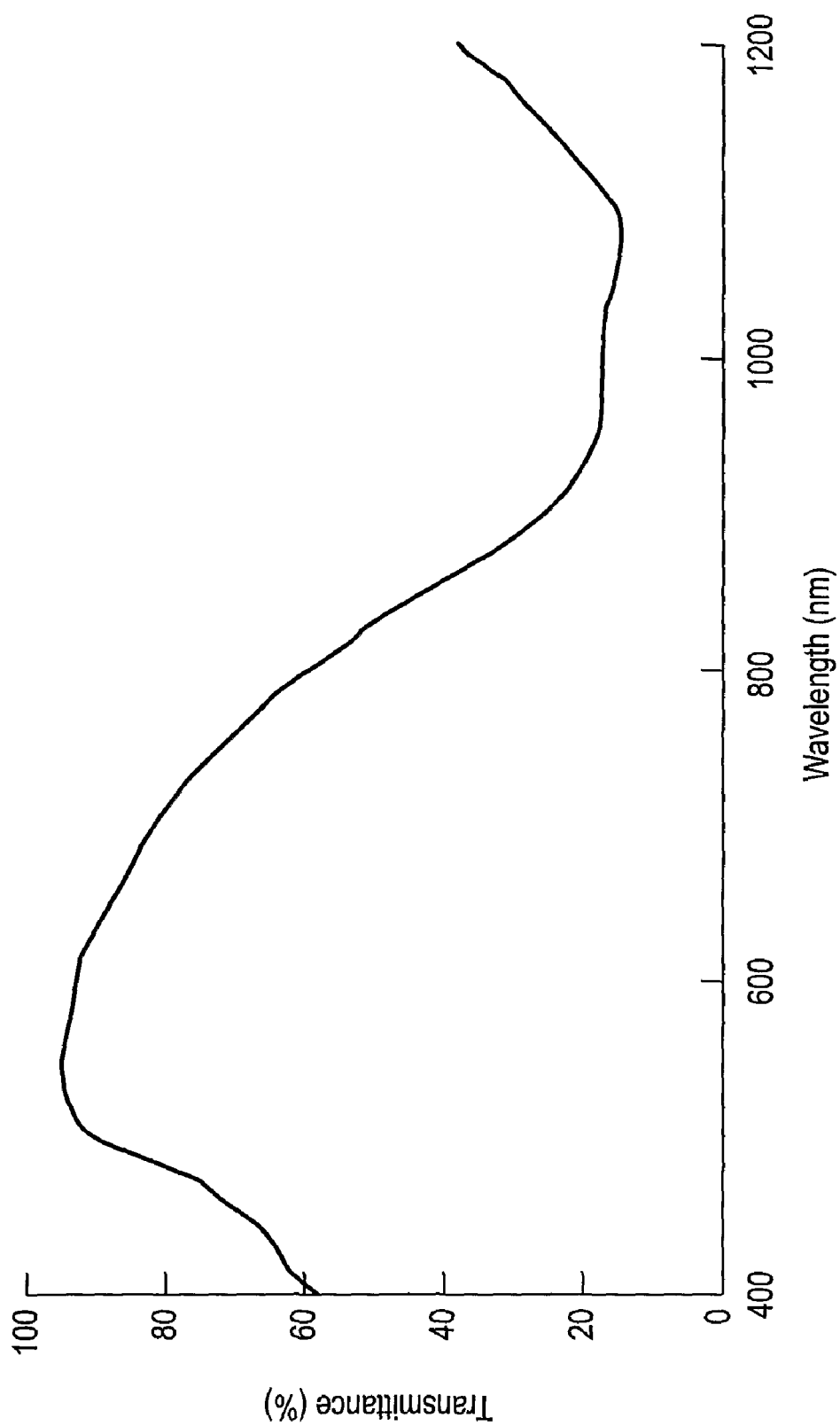
FIG. 5 is a visible-near-infrared absorbing spectrum of a diimmonium BPh4 salt used in Comparative Example 3-1.
Figure 6:
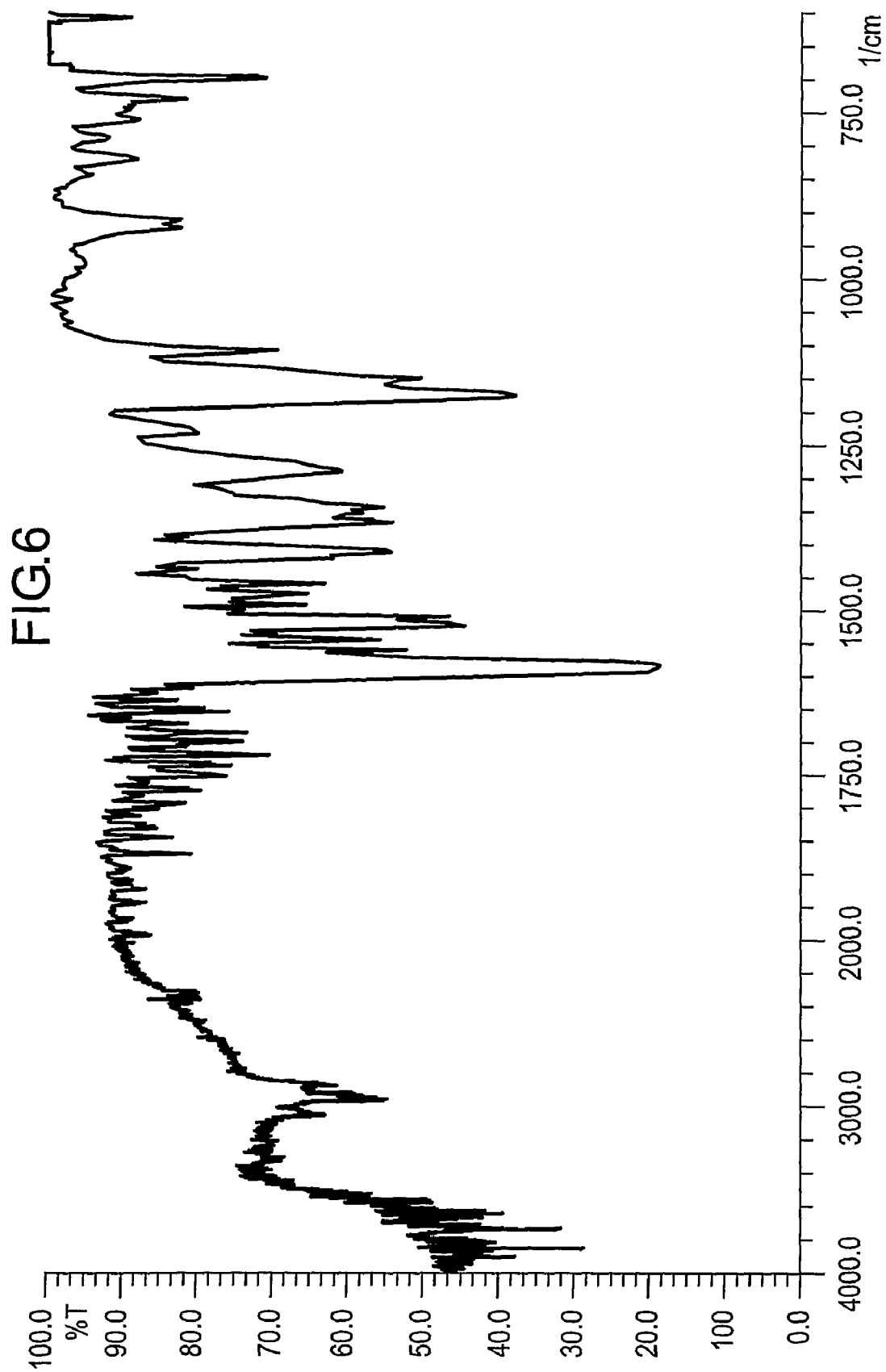
FIG. 6 is an IR spectrum of a diimmonium BPh4 salt used in Comparative Example 3-1.

From the above results, it was confirmed that although the red brown solid was tetraphenylborate of diimmonium as the raw material (referred to as "diimmonium BPh4 salt"), it was unstable and labile to change into the aminium salt. Visible-near-infrared absorbing spectrum of the diimmonium BPh4 salt measured in a MEK solution is shown in FIG. 5 and IR spectrum of the diimmonium BPh4 salt measured by a KBr method is shown in FIG. 6.

Comparative Example 3-2

By dissolving 2 parts of a diimmonium BPh4 salt into 98 parts of MEK, a solution 4 of a near-infrared ray absorbing dye was prepared. Using HALSHYBRID IR-G205 (from Nippon Shokubai Co., Ltd.: solid content of 29%) as a binder, 69 parts of the binder, 11 parts of the dye solution 4 obtained, 16 parts of MEK were mixed, to obtain a solution B3 of a near-infrared ray absorption material having a solid content of coating material of 21% (solid content ratio: resin/dye/borate=100/1.1/0).

Comparative Example 3-3

The solution B3 of a near-infrared ray absorption material was applied and dried similarly as in Example 1-2, to obtain a near-infrared ray absorption substrate B3. The near-infrared ray absorption substrate B3 was evaluated for by using the same method as in Example 1-2, and the results are shown in Table 2.

TABLE 2

| | Resin (Solid content ratio) | Dye (Solid content ratio) | Borate (Solid content ratio) | Near-infrared ray transmittance (%) | Total light transmittance (%) | Heat resistance ΔT (%) | Heat resistance Δb* |
|---|---|---|---|---|---|---|---|
| Example 3-3 (A3) | X1 100 | Y2 1.7 | None — | 27.9 | 88.3 | 2.5 | 0.6 |
| Comp. Examp. 2-3 (B2) | X1 100 | Y3 1.0 | None — | 23.7 | 88.1 | 6.5 | 1.3 |
| Comp. Examp. 3-3 (B3) | X1 100 | Y4 1.1 | None — | 86.8 | 90.1 | 7.6 | -2.3 |

X1: HALSHYBRID IR-G205 (produced from Nippon Shokubai Co., Ltd.)
Y2: N,N,N',N'-tetrakis(p-di(n-butyl)aminophenyl)-p-phenylene diimmonium tetrakis(pentafluorophenyl)borate
Y3: N,N,N',N'-tetrakis(p-di(n-butyl)aminophenyl)-p-phenylene diimmonium hexafluoroantimonate
Y4: N,N,N',N'-tetrakis(p-di(n-butyl)aminophenyl)-p-phenylene diimmonium tetraphenylborate It is noted from the results shown in the Table 2 that although the near-infrared ray absorption substrate A3 of the present invention, comparing with the near-infrared ray absorption substrate B2 wherein a diimmonium-based dye having no borate anion of the present invention was used, has equivalent transmittance of near-infrared ray and total light transmittance, change in optical characteristics (change in transmittance and change in color difference) at 100° C. after 120 hours is significantly smaller in the near-infrared ray absorption substrate A3 of the present invention than the near-infrared ray absorption substrate B2, suggesting that the near-infrared ray absorption material of the present invention is difficult to be deteriorated.

It is also noted from the results shown in the Table 2 that although the near-infrared ray absorption substrate A3 of the present invention, comparing with the near-infrared ray absorption substrate B3 wherein a diimmonium-based dye composed of a borate anion having an aryl group having no electron withdrawing group was used, has equivalent total light transmittance, near-infrared ray absorption ability is remarkably higher in the near-infrared ray absorption material A3. In addition, it is also noted that change in optical characteristics (change in transmittance and change in color difference) at 100° C. after 120 hours is significantly smaller in the near-infrared ray absorption substrate A3 of the present invention than the near-infrared ray absorption substrate B3, suggesting that the near-infrared ray absorption material of the present invention is difficult to be deteriorate.

Example 4-1

407.0 parts of methylmethacrylate, 93.0 parts of n-butyl acrylate as monomers were mixed, to obtain a monomer mixture. 6.0 parts of PERKADOX 12-XL25 (from Kayaku Akuzo Corp.) and 100 parts of toluene were mixed, to obtain an initiator solution. 350 parts of the monomer mixture and 250 parts of toluene were added into a flask, and a thermometer, a stirrer, a nitrogen gas introduction tube, a reflux cooler and a dropping funnel were set thereto. 150 parts of the monomer mixture and 31.8 parts of the initiator solution were mixed and added into the dropping funnel. While passing nitrogen gas at 20 ml/minute, the flask was heated so as to have the inner temperature reach 100° C. 74.2 parts of the initiator solution was added to the flask to start the polymerization. After 20 minutes from charging of the polymerization initiator, the monomers and the initiator solution in the dropping funnel were added over 60 minutes. After the addition, the dropping funnel was washed with 75 parts of toluene and the washed solution was added into the flask. Subsequently, the solution was subjected to aging for 60 minutes and 150 parts of toluene was added as a diluent. The solution was further subjected to aging for 60 minutes and 150 parts of toluene was added as a diluent. Then, the solution was subjected to further aging for 60 minutes and 150 parts of toluene was added as a diluent. The solution was subjected to further aging for 60 minutes and then raised the temperature up to 110° C. After raising the temperature, the solution was subjected to further aging for 300 minutes and 100 parts of toluene was added as a diluent. By cooling to room temperature, a resin A was obtained. The resin A had a solid content of 34.4%, weight average molecular weight of 198,000 and Tg of 77° C.

Example 4-2

By dissolving 6 parts of N,N,N',N'-tetrakis(p-di(n-butyl) aminophenyl)-p-phenylene diimmonium bis(trifluoromethanesulfone)imide salt and 5 parts of EXCOLOR IR-10A (produced from Nippon Shokubai Co., Ltd.) were dissolved into 89 parts of MEK, to prepare a solution of a near-infrared ray absorbing dye. Then, 5 parts of tetrakis (pentafluorophenyl)borate 1-methylimidazolium was dissolved into 95 parts of MEK, to prepare a borate solution 2. Subsequently, 58 parts of the resin A, 10 parts of the solution 5 of a near-infrared ray absorbing dye, 10 parts of the borate solution 2 and 24 parts of MEK were mixed, to obtain a solution A4 of a near-infrared ray absorption material having a solid content of coating material of 21% (solid content ratio: resin/dye/borate=100/5.5/2.5).

Example 4-3

The solution A4 of a near-infrared ray absorption material was applied on an easy adhesion type PET film (COSMOSHINE A4300, produced from Toyobo, Ltd.) using a bar coater (No. 34) and then dried in a hot air dryer at 150° C. for 3 minutes, to obtain a near-infrared ray absorption substrate A4. The near-infrared ray absorption substrate A4 was evaluated for transmittance of near-infrared ray, total light transmittance and heat resistance and the results are shown in Table 3. In this case, the transmittance of near-infrared ray was determined at a wavelength of 1090 nm.

Example 5-1

By dissolving 5 parts of N,N-dimethylcyclohexylammonium tetrakis(pentafluorophenyl)borate into 95 parts of MEK, a borate solution 3 was prepared. Then, 58 parts of the resin A, 10 parts of the solution 5 of a dye absorbing near-infrared, 10 parts of the borate solution 3 and 24 parts of MEK were mixed, to obtain a solution A5 of a near-infrared ray absorption material having a solid content of coating material of 21% (solid content ratio: resin/dye/borate=100/5.5/2.5).

Example 5-2

The solution A5 of a near-infrared ray absorption material was applied and dried similarly as in Example 4-3, to obtain a near-infrared ray absorption substrate 5. The near-infrared ray absorption substrate A5 was evaluated by using the same method as in Example 4-3, and the results are shown in Table 3.

Comparative Example 4-1

58 parts of the resin A, 10 parts of the solution 5 of a near-infrared ray absorbing dye and 32 parts of MEK were mixed, to obtain a solution B4 of a near-infrared ray absorption material having a solid content of coating material of 21% (solid content ratio: resin/dye/borate=100/5.5/0).

Comparative Example 4-2

The solution B4 of a near-infrared ray absorption material was applied and dried similarly as in Example 4-3 to obtain a near-infrared ray absorption substrate B4. The near-infrared ray absorption substrate B4 was evaluated by using the same method as in Example 4-3, and the results are shown in Table 3.

TABLE 3

| | Resin (Solid content ratio) | Dye (Solid content ratio) | Borate (Solid content ratio) | Near-infrared ray transmittance (%) | Total light transmittance (%) | Moisture resistance ΔT (%) | Moisture resistance Δb* |
|---|---|---|---|---|---|---|---|
| Example 4-3 (A4) | X2 100 | Y5 5.5 | Z2 2.5 | 1.0 | 65.3 | 0.6 | 2.3 |
| Example 5-2 (A5) | X2 100 | Y5 5.5 | Z3 2.5 | 1.8 | 67.8 | 2.3 | 5.9 |
| Comp. Examp. 4-2 (B4) | X2 100 | Y5 5.5 | None — | 1.4 | 65.9 | 5.7 | 11.6 |

X2: Resin A
Y5: Mixture of an N,N,N',N'-tetrakis(p-di(n-butyl)aminophenyl)-p-phenylene diimmonium bis(trifluoromethanesulfone)imide salt and EXCOLOR IR-10A (produced from Nippon Shokubai Co., Ltd.)
Z2: Tetrakis(pentafluorophenyl)borate 1-methylimidazolium
Z3: Tetrakis(pentafluorophenyl)borate N,N-dimethylcyclohexylammonium It is noted from the results shown in the Table 3 that although the near-infrared ray absorption substrates A4 and A5 of the present invention, comparing with the near-infrared ray absorption substrate B4 wherein a borate anion of the present invention was not used, have equivalent transmittance of near-infrared ray and total light transmittance, change in optical characteristics (change in transmittance and change in color difference) at 80° C. and 95% RH after 120 hours is significantly smaller in the near-infrared ray absorption substrates A4 and A5 of the present invention than the near-infrared ray absorption substrate B4, suggesting that the near-infrared ray absorption material of the present invention is difficult to be deteriorated.

Example 6-1

2-Ethylhexyl acrylate (478.2 parts), cyclohexyl methacrylate (120 parts) and hydroxyethyl acrylate (1.8 parts) as monomers were weighed and thoroughly mixed, to obtain a monomer mixture. The monomer mixture (240 parts) and ethyl acetate (147 parts) were added into a flask equipped with a thermometer, a stirrer, an inert gas introduction tube, a reflux cooler and a dropping funnel. The monomer mixture for dropping composed of the monomer mixture (360 parts), ethyl acetate (16 parts) and NYPER BMT-K40 (0.72 parts) as a polymerization initiator were charged into the dropping funnel and mixed well. While passing nitrogen gas at 20 ml/minute, the inner temperature of the flask was raised to 84° C. and NYPER BMT-K40 (0.96 parts) as a polymerization initiator was charged into the flask to start the polymerization. After 10 minutes from charging the polymerization initiator, the monomer mixture for dropping charged in the dropping funnel was started to be added dropwise. The monomer mixture for dropping was dropped evenly over 90 minutes. After the dropping had been completed, ethylacetate (50 parts) was charged into the flask. Then, the reaction solution was aged at 82° C. for 4.3 hours. After the completion of the reaction, ethyl acetate (44.4 parts) was added and finally the reaction solution was diluted with toluene so as to give the nonvolatile content of about 45%, to obtain an acrylic polymer solution. This was referred to as pressure-sensitive adhesive A. The pressure-sensitive adhesive A had a calculated to have Tg of −51° C. and an acid value of 0.

Example 6-2

By dissolving 2.5 parts of a diimmonium SbF6 salt and 2.5 parts of EXCOLOR IR-10A (produced from Nippon Shoukubai Co., Ltd.) into 95 parts of MEK, a solution 6 of a near-infrared ray absorbing dye was prepared. Then, using the pressure-sensitive adhesive A as a resin, 89 parts of the pressure-sensitive adhesive A, 16 parts of the solution 6 of a near-infrared ray absorbing dye, 16 parts of the borate solution 1 and 18 parts of MEK were mixed to obtain a solution A6 of a near-infrared ray absorption material having a solid content of coating material of 30% (solid content ratio: resin/dye/borate=100/2/2).

Example 6-3

Figure 7:
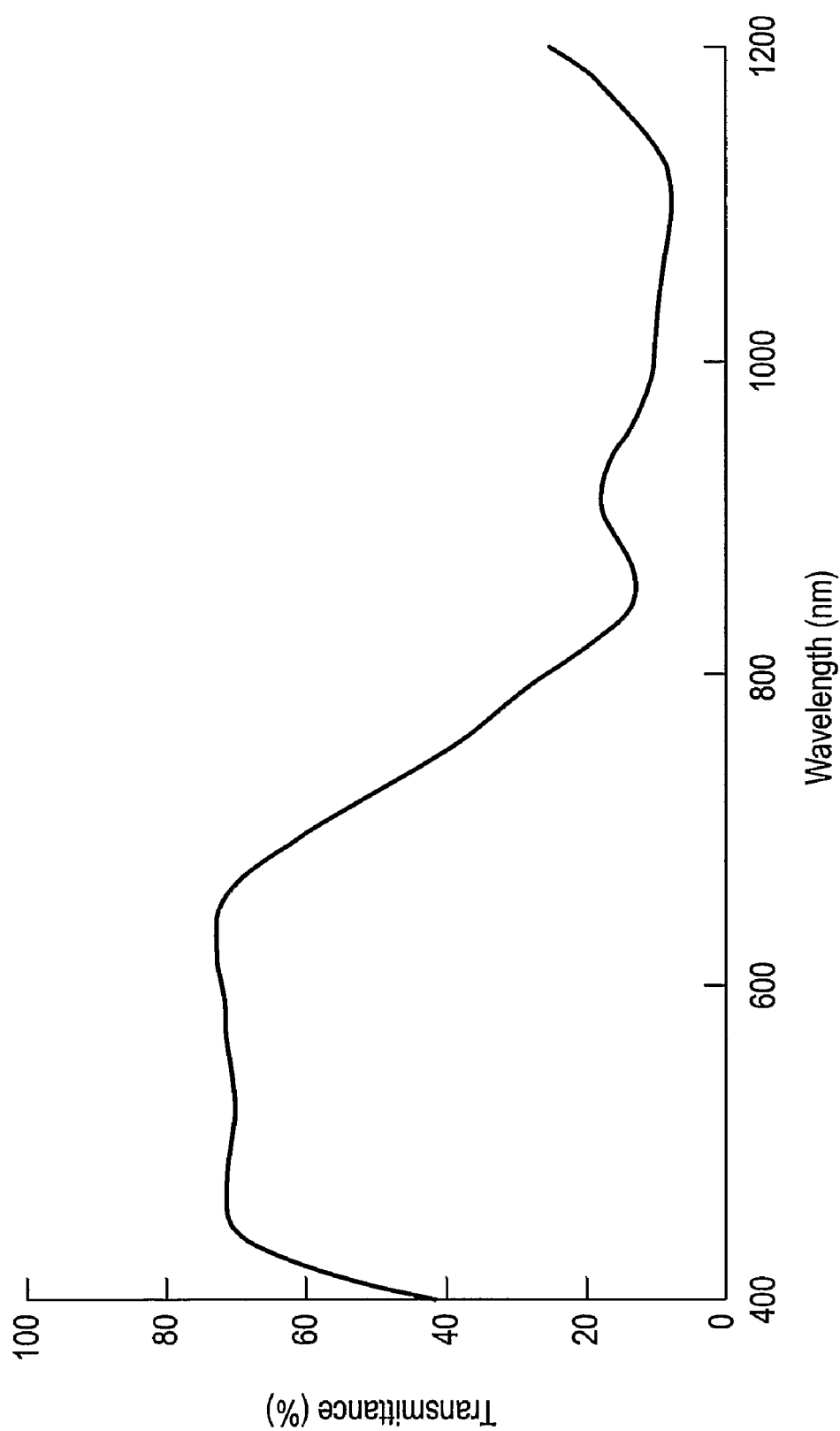
FIG. 7 is a visible-near-infrared absorbing spectrum of near-infrared ray absorption material A6 prepared in Example 6-3.

The solution A6 of a near-infrared ray absorption material was applied on an easy adhesion type PET film (COSMOSHINE A4300, produced from Toyobo, Ltd.) using a bar coater (No. 50) and dried in a hot air dryer at 150° C. for 3 minutes, to form a coating film with a thickness of 10 μm. On this film, another easy adhesion type PET film (COSMOSHINE A4300, produced from Toyobo, Ltd.) was adhered, to obtain a near-infrared ray absorption substrate A6. visible-near-infrared absorbing spectrum of this near-infrared ray absorption substrate A6 is shown in FIG. 7. This was used as a test sample for heat resistance test. The near-infrared ray absorption substrate A6 was evaluated for transmittance of near-infrared ray, total light transmittance and heat resistance and the results are shown in Table 4. In this case, the transmittance of near-infrared ray was determined at a wavelength of 1090 nm.

Comparative Example 5-1

By mixing 89 parts of the pressure-sensitive adhesive A, 16 parts of the solution 6 of a near-infrared ray absorbing dye and 31 parts of MEK, a solution B5 of a near-infrared ray absorption material having a solid content of coating material of 30% was obtained (solid content ratio: resin/dye/borate=100/2/0).

Comparative Example 5-2

Figure 8:
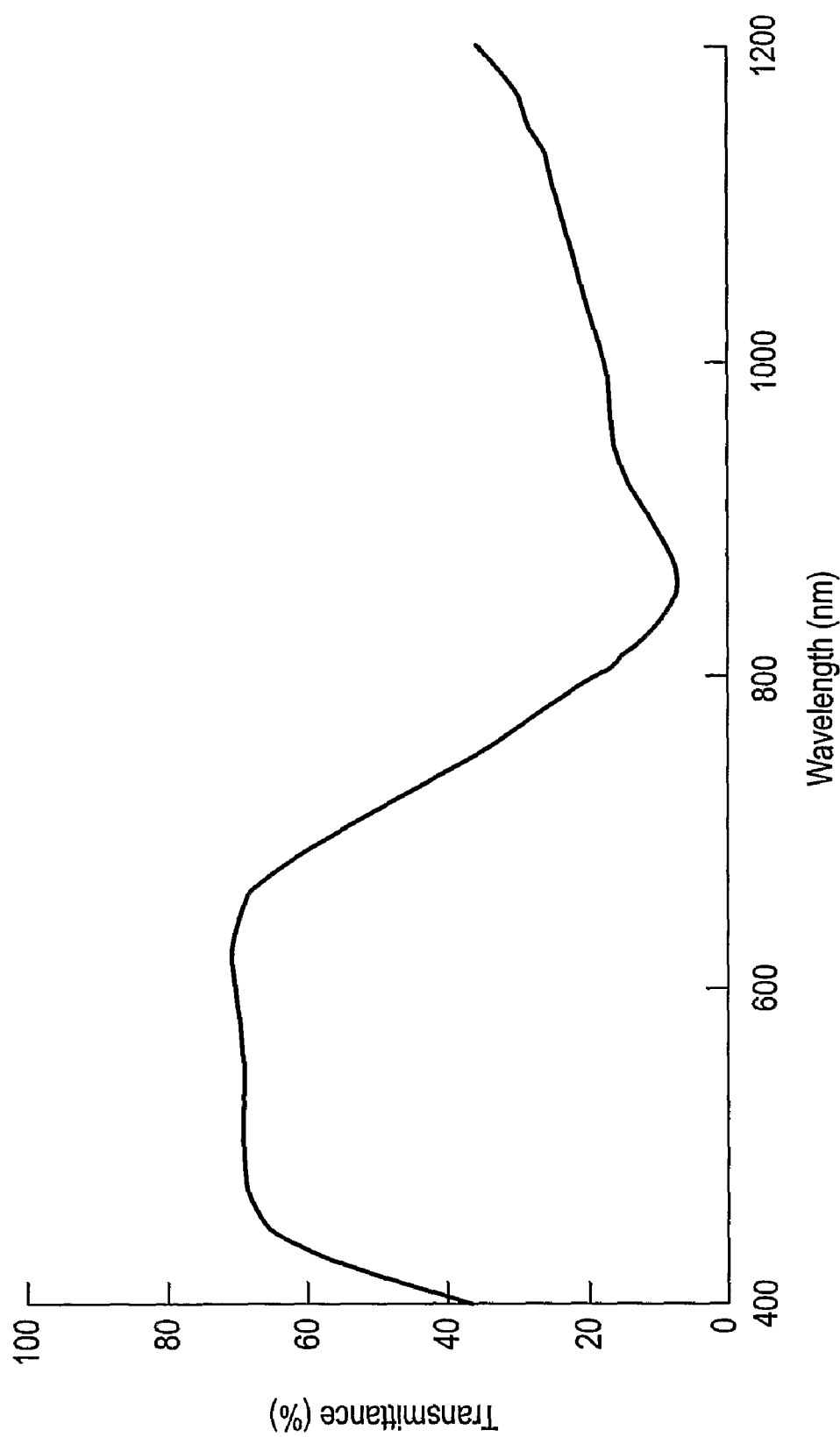
FIG. 8 is a visible-near-infrared absorbing spectrum of near-infrared ray absorption material B5 prepared in Comparative Example 5-2.

A near-infrared ray absorption substrate B5 was obtained similarly as in Example 6-3 while using the solution B5 of a near-infrared ray absorption material instead. Visible-near-infrared absorbing spectrum of this near-infrared ray absorption substrate B5 is shown in FIG. 8. This substrate was evaluated similarly as in Example 6-3 and results are shown in Table 4.

Comparative Example 6-1

By dissolving 5 parts of sodium tetraphenylborate (produced from Dojindo Lab. under the name of Kalibor) into 95 parts of MEK, a borate solution 4 was prepared. The pressure-sensitive adhesive A of 89 parts, 16 parts of the solution 6 of a near-infrared ray absorbing dye, 16 parts of the borate solution 4 and 31 parts of MEK were mixed, to obtain a solution B6 of a near-infrared ray absorption material having a solid content of coating material of 30% (solid content ratio: resin/dye/borate=100/2/2).

Comparative Example 6-2

Figure 9:
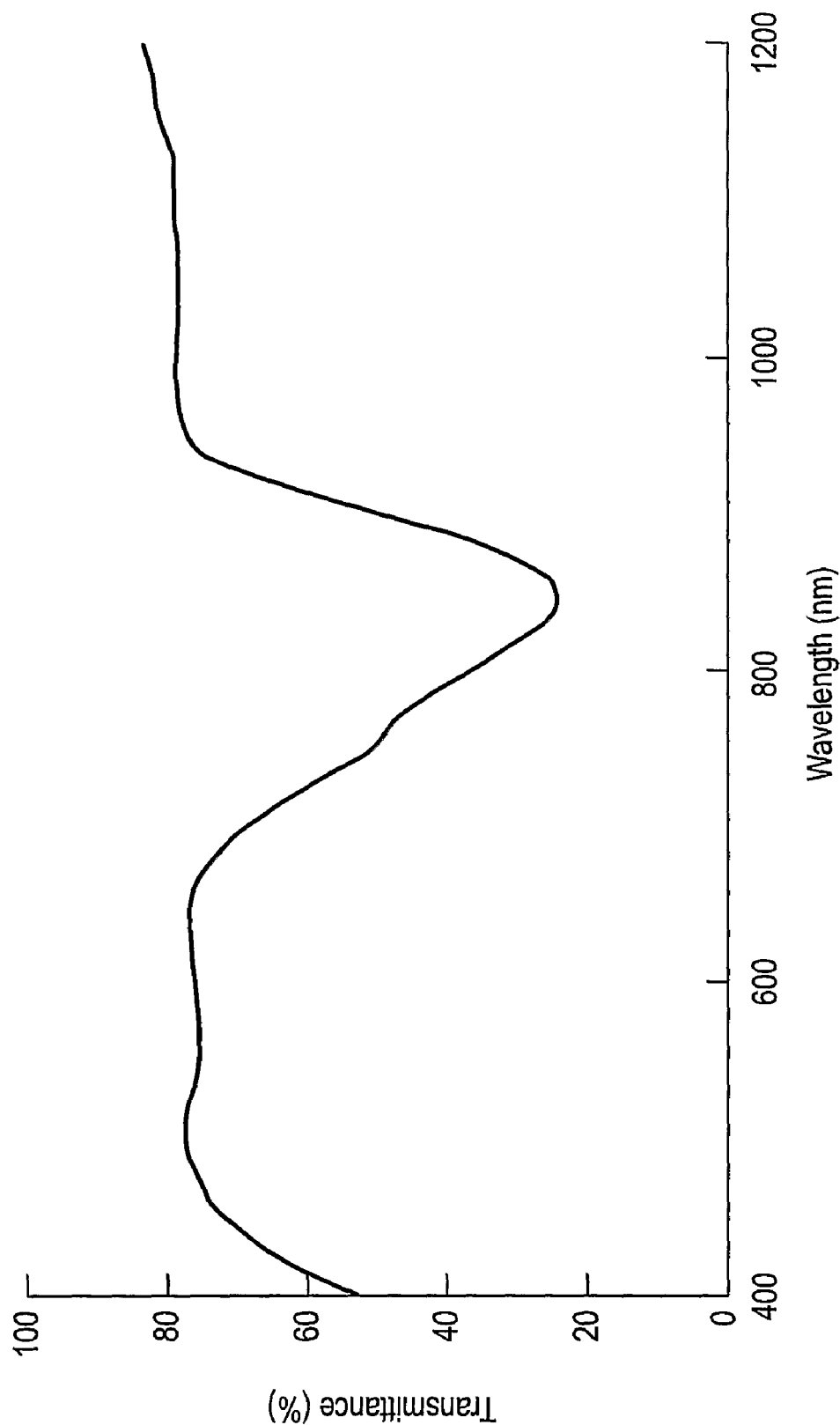
FIG. 9 is a visible-near-infrared absorbing spectrum of near-infrared ray absorption material B6 prepared in Comparative Example 6-2.

Using the solution B6 of a near-infrared ray absorption material, a near-infrared ray absorption substrate B6 was obtained similarly as in Example 6-3. Visible-near-infrared absorbing spectrum of this near-infrared ray absorption substrate B6 is shown in FIG. 9. This substrate B6 was used as a test sample for a heat resistance test. The substrate B6 was evaluated similarly as in Example 6-3 and results are shown in Table 4.

absorption substrate B6, suggesting that the near-infrared ray absorption material of the present invention shows less deterioration.

Example 7-1

Into a four necked flask equipped with a stirrer, a nitrogen introduction tube, a dropping funnel, a thermometer and a cooling tube were added 278 parts of 2-ethylhexylacrylate, 120 parts of cyclohexyl methacrylate, 2 parts of 2-hydroxyethyl acrylate and 258 parts of ethyl acetate, and the mixture was heated up to 85° C. under nitrogen atmosphere. After the inner temperature reached 85° C., 0.8 parts of NYPER BMT-K40 (produced from NOF Corp.) and 8 parts of ethyl acetate were charged, to initiate the polymerization. After 10 minutes from the start of the reaction, 417 parts of 2-ethylhexyl acry-

TABLE 4

|  | Resin (Solid content ratio) | Dye (Solid content ratio) | Borate (Solid content ratio) | Near-infrared ray transmittance (%) | Total light transmittance (%) | Heat resistance ΔT (%) | Heat resistance Δb* |
|---|---|---|---|---|---|---|---|
| Example 6-3 (A6) | X3 100 | Y6 2.0 | Z1 2.0 | 14.9 | 71.6 | 3.5 | 2.4 |
| Comp. Examp. 5-2 (B5) | X3 100 | Y6 2.0 | None — | 15.5 | 69.3 | 21.1 | 0.0 |
| Comp. Examp. 6-2 (B6) | X3 100 | Y6 2.0 | Z4 2.0 | 77.6 | 77.1 | 10.5 | 1.0 |

X3: Pressure-sensitive adhesive A
Y6: Mixture of an N,N,N',N'-tetrakis(p-di(n-butyl)aminophenyl)-p-phenylene diimmonium hexafluoroantimonate and EXCOLOR IR-10A (produced from Nippon Shokubai Co., Ltd.)
Z1: Sodium tetrakis(pentafluorophenyl)borate
Z4: Sodium tetraphenylborate Among the results shown in the Table 4, first of all, by comparing the results on the near-infrared ray absorption substrate A6 of the present invention with those on the near-infrared ray absorption substrate B5 wherein a borate solution according to the present invention was not used, it was found that although the near-infrared ray absorption substrate A6 has transmittance of near-infrared ray and total light transmittance equivalent to the near-infrared ray absorption substrate B5, change in optical characteristics (change in transmittance) at 100° C. after 120 hours is significantly smaller in the near-infrared ray absorption substrate A6 of the present invention than the near-infrared ray absorption substrate B5, suggesting that near-infrared ray absorption material of the present invention is difficult to be deteriorated.

In addition, by comparing the results on the near-infrared ray absorption substrate A6 of the present invention with those on the near-infrared ray absorption substrate B6 wherein a salt composed of a borate anion having an aryl group having no electron withdrawing group, it was found that although these absorption substances have equivalent total light transmittance, transmittance of near-infrared ray of the near-infrared ray absorption substrate A6 of the present invention was significantly smaller than the near-infrared ray absorption substrate B6, suggesting that the near-infrared ray absorption substrate A6 can fulfill significantly higher efficiency of cutting near-infrared ray. Furthermore, by comparing heat resistance between the near-infrared ray absorption substrate A6 of the present invention and the near-infrared ray absorption substrate B6, a near-infrared ray absorption substrate A6 of the present invention exhibited significantly smaller change in optical characteristics (change in transmittance) at 100° C. after 120 hours than the near-infrared ray late, 180 parts of cyclohexyl methacrylate, 3 parts of 2-hydroxyethyl acrylate, 0.6 parts of NYPER BMT-K40 and 10 parts of ethyl acetate were added dropwise over 90 minutes. After each 120, 150, 180 and 210 minutes from the end of the dropping, 1 part of azobisisobutylonitrile and 10 parts of ethyl acetate were charged to continue the reaction for 2 hours under reflux, and finally diluted with ethylacetate so as to give the solid content of 40%, to obtain a pressure-sensitive adhesive B solution. The polymer obtained had a weight average molecular weight of 350,000, a calculated Tg of –40° C. and an acid value of 0.

Example 7-2

By dissolving 4 parts of a diimmonium TEPB salt and 2 parts of EXCOLOR IR-10A (produced from Nippon Shoukubai Co., Ltd.) into 94 parts of MEK, a solution 7 of a near-infrared ray absorbing dye was prepared. Then, 10 parts of N,N-dimethyl-4-methylanilinium tetrakis(pentafluorophenyl)borate was dissolved into 90 parts of MEK, to prepare a borate solution 5. Then, 50 parts of the pressure-sensitive adhesive B solution, 10 parts of the solution 7 of a near-infrared ray absorbing dye and 10 parts of the borate solution 5 were mixed, to obtain a solution A7 of a near-infrared ray absorption material having a solid content of coating material of 31% (solid content ratio: resin/dye/borate=100/3/5).

Example 7-3

The solution A7 of a near-infrared ray absorption material was applied on an easy adhesion type PET film (COSMO-SHINE A4300, produced from Toyobo, Ltd.), so that thickness of a layer of pressure-sensitive adhesive after drying was 20 μm, and dried in a hot air dryer at 100° C. for 2 minutes. By adhesion of this pressure sensitive adhesive film onto a glass plate, a near-infrared ray absorption substrate A7 was obtained. This was used as a test sample for moisture resistance test. This substrate A7 was evaluated for transmittance of near-infrared ray, total light transmittance and moisture resistance and results are shown in Table 5. In this case, the transmittance of near-infrared ray was determined at a wavelength of 1090 nm.

Example 8-1

By dissolving 10 parts of quinolinium terakis(pentafluorophenyl)borate into 90 parts of MEK, a borate solution 6 was prepared. Then, 50 parts of the pressure-sensitive adhesive B solution, 10 parts of the solution 7 of a dye absorbing near-infrared and 10 parts of the borate solution 6 were mixed, to obtain a solution A8 of a near-infrared ray absorption material having a solid content of coating material of 31% (solid content ratio: resin/dye/borate=100/3/5).

Example 8-2

A near-infrared ray absorption substrate A8 was obtained similarly as in Example 7-3 while using the solution A8 of a near-infrared ray absorption material instead. This substrate A8 was evaluated similarly as in Example 7-3 and results are shown in Table 5.

Comparative Example 7-1

By dissolving 4 parts of a diimmonium $SbF_6$ salt and 2 parts of EXCOLOR IR-10A (produced from Nippon Shoukubai Co., Ltd.) into 94 parts of MEK, a solution 8 of a near-infrared ray absorbing dye was prepared. Then, 50 parts of the pressure-sensitive adhesive B solution, 10 parts of the solution 8 of a near-infrared ray absorbing dye and 10 parts of ethyl acetate were mixed, to obtain a solution B7 of a near-infrared ray absorption material having a solid content of coating material of 29% (solid content ratio: resin/dye/borate=100/3/0).

Comparative Example 7-2

A near-infrared ray absorption substrate B7 was obtained similarly as in Example 7-3 while using the solution B7 of a near-infrared ray absorption material instead. This substrate B7 was used as a test sample for moisture resistance test. This substrate B7 was evaluated similarly as in Example 7-3 and results are shown in Table 5.

TABLE 5

| | Resin (Solid content ratio) | Dye (Solid content ratio) | Borate (Solid content ratio) | Near-infrared ray transmittance (%) | Total light transmittance (%) | Moisture resistance ΔT (%) | Moisture resistance Δb* |
|---|---|---|---|---|---|---|---|
| Example 7-3 (A7) | X4 100 | Y7 3.0 | Z5 5 | 1.2 | 52.8 | 4.6 | 11.2 |
| Example 8-2 (A8) | X4 100 | Y7 3.0 | Z6 5 | 2.8 | 55.8 | 0.8 | 4.7 |
| Example 9-2 (A9) | X4 100 | Y7 3.0 | None — | 0.6 | 49.8 | 38.6 | 28.7 |
| Comp. Examp. 7-2 (B7) | X4 100 | Y8 3.0 | None — | 42.8 | 58.2 | 32.4 | 0.5 |

X4: Pressure-sensitive adhesive B
Y7: Mixture of N,N,N',N'-tetrakis(p-di(n-butyl)aminophenyl)-p-phenylene diimmonium terakis(pentafluorophenyl)borate and EXCOLOR IR-10A(from Nippon Shokubai Co., Ltd.)
Y8: Mixture of N,N,N',N'-tetrakis(p-di(n-butyl)aminophenyl)-p-phenylene diimmonium hexafluoroantiomonate and EXCOLOR IR-10A(from Nippon Shokubai Co., Ltd.)
Z5: N,N-dimethyl-4-methylanilinium tetrakis(pentafluorophenyl)borate
Z6: Quinolinium terakis(pentafluorophenyl)borate Example 9-1

By mixing 50 parts of the pressure-sensitive adhesive B solution, 10 parts of the solution 7 of a near-infrared ray absorbing dye and 10 parts of ethyl acetate, a solution A9 of a near-infrared ray absorption material having a solid content of coating material of 29% was obtained (solid content ratio: resin/dye/borate=100/3/0).

Example 9-2

A near-infrared ray absorption substrate A9 was obtained similarly as in Example 7-3 while using the solution A9 of a near-infrared ray absorption material instead. This was used as a test sample for a moisture resistance test. This substrate A9 was evaluated similarly as in Example 7-3 and results are shown in Table 5.

Among the results shown in the Table 5, first of all, by comparing the results on the near-infrared ray absorption substrate A9 with those on the near-infrared ray absorption substrate B7 wherein a borate anion of the present invention was not used, it was found that although the near-infrared ray absorption substrate A9 has total light transmittance equivalent to the near-infrared ray absorption substrate B7, transmittance of near-infrared ray is significantly smaller in the near-infrared ray absorption substrate A9 of the present invention, suggesting that the near-infrared ray absorption substrate A9 of the present invention can fulfill significantly higher efficiency of cutting near-infrared ray than the near-infrared ray absorption substrate B7.

In addition, the near-infrared ray absorption substrates A7 and A8 wherein both of a diimmonium dye having a borate anion of the present invention, and a borate of the present invention were used, and also the near-infrared ray absorption substrates A9 of the present invention, have significantly smaller change in optical characteristics (change in transmittance) at 80° C. and 95% RH after 120 hours than the near-infrared ray absorption substrate A6, suggesting that the near-infrared ray absorption material of the present invention is difficult to be deteriorated, even when a pressure-sensitive adhesive is used on a glass substrate.

Example 10

1. Synthesis of Polymerizable Polysiloxane (M-1)

Into a four necked flask of 300 ml and equipped with a stirrer, a thermometer and a cooling tube were charged 144.5 parts of tetramethoxysilane, 23.6 parts of γ-methacryloxypropyltrimethoxysilane, 19.0 parts of water, 30.0 parts of methanol and 5.0 parts of Amberlyst 15 (Tradename, a cation exchange resin produced from Organo Corp.), and the resultant mixture was stirred at 65° C. for 2 hours to react. After cooling the reaction mixture to room temperature, a distillation tower, and cooling tube and an effluent exit connected thereto were set, instead of the cooling tube, and the inner temperature of the flask was raised up to about 80° C. over 2 hours under normal pressure, and the same temperature was maintained till methanol did not flow out. Furthermore, the mixture was maintained at 90° C. under a pressure of 2.67×10 kPa till methanol did not flow out, to additionally carry out the reaction. Again, the mixture was cooled to room temperature, and then Amberlyst 15 was filtered off, to obtain polymerizable polysiloxane (M-1) with number average molecular weight of 1,700.

2. Synthesis of an Organic Polymer (P-1)

Into a one L flask equipped with a stirrer, a dropping port, a thermometer and a cooling tube was charged 260 parts of n-butyl acetate as an organic solvent, and nitrogen gas was introduced and the inner temperature of the flask was raised up to 110° C. while stirring. Then a mixed solution of 12 parts of polymerizable polysiloxane (M-1), 19 parts of tert-butyl methacrylate, 94 parts of butyl acrylate, 67 parts of 2-hydroxyethyl methacrylate, 48 parts of perfluorooctylethyl methacrylate (LIGHT-ESTER FM-108, produced from KYOEISHA CHEMICAL Co., Ltd.) and 2.5 parts of 2,2'-azobis-(2-methylbutyronitrile) was dropped from the dropping port over 3 hours. After continuing stirring at the same temperature for 1 hour even after the dropping had been completed, 0.1 part of tert-butylperoxy-2-ethylhexanoate was added twice in 30 minutes interval, and the mixture was copolymerized by heating for another 2 hours, to obtain a n-butyl acetate solution of an organic polymer (P-1) with a number average molecular weight of 12,000 and a weight average molecular weight of 27,000. The resultant solution had a solid content of 48.2%.

3. Synthesis of Dispersion (S-1) of a Composite of Organic Polymer with Inorganic Fine Particles Into a four necked flask of 500 ml and equipped with a stirrer, two dropping ports (dropping port A and dropping port B) and a thermometer were charged in advance 200 parts of n-butyl acetate and 500 parts of methanol, and the inner temperature was adjusted to 40° C. Then, while stirring inside the flask, a mixture solution (raw material solution A) composed of 10 g of the solution of organic polymer in n-butyl acetate (P-1), 30 parts of tetramethoxysilane and 5 parts of n-butyl acetate was dropped from the dropping port A, and a mixture solution (raw material solution B) composed of 5 parts of an aqueous 25% ammonia solution, 10 parts of deionized water and 15 parts of methanol was dropped from the dropping port B over 2 hours. After the dropping had been completed, a distillation tower and a cooling tube and an effluent exit connected thereto were set, instead of the cooling tube, and the inner temperature of the flask raised up to 100° C. under a pressure of 40 kPa, and then ammonia, methanol and n-butyl acetate were removed so as to give the solid content of 30%, to obtain a dispersion (S-1) having dispersed in n-butyl acetate a dispersion (S-1) of a composite of organic polymer with inorganic fine particles having a ratio of inorganic fine particles to the organic polymer in the composite of 70/30. The average particle diameter of the resultant composite was 23.9 nm. The ratio of inorganic fine particles and the organic polymer in the organic polymer composite with inorganic fine particles was determined by elemental analysis on the dispersion of the organic polymer composite with inorganic fine particles, after drying at 130° C. for 24 hours under a pressure of 1.33×10 kPa. In this case, the ash is regarded as a content of the organic polymer composite with inorganic fine particles. In addition, the average particle diameter was determined by using a solution of 1 part of the dispersion (S-1) of the organic polymer composite with inorganic fine particles diluted with 99 parts of n-butyl acetate, subjecting particles in the solution to photographing with a transmission electron microscope, measuring diameters of arbitrary 100 particles, to obtain an average as the average particle diameter.

4. Reflecting Film

Into a solution obtained by mixing 8 parts of dipentaerythritol hexaacrylate (DPE-6A, produced from KYOEISHA CHEMICAL Co., Ltd.) and 2 parts of pentarythritol triacrylate (PE-3A, produced from KYOEISHA CHEMICAL Co., Ltd.) and dissolving the mixture into 40 parts of MEK, a solution of 0.5 part of a photopolymerization initiator (Irgacure 907, produced from Nippon Ciba Geigy K.K.) in 2 parts of MEK was added, to prepare a coating solution for a hard coat layer.

By mixing 9 parts of the dispersion (S-1) of the organic polymer composite with inorganic fine particles, 0.3 part of Desmodule N3200 (Tradename, an isocyanate curing agent, produced from Sumitomo Bayer Urethane Co., Ltd.) and 0.003 part of di-n-butyltin dilaurate and 110 parts of methyl isobutyl ketone, a coating solution for a low refractive index layer was prepared.

The coating solution for a hard coat layer was applied on a PET film (COSMOSHINE A4300, produced from Toyobo, Ltd.) with a thickness of 188 μm using the bar coater and, after drying at 100° C. for 15 minutes, the coated layer was cured by irradiation of UV ray of 200 mJ/cm² using a high pressure mercury lamp, to form a hard coat layer with a thickness of 5 μm. Then, the coated layer was cured on the hard coated layer, to form a hard coat layer with a film thickness of 5 μm. Then, by applying the coating solution for a low refractive index layer on this hard coat layer using a bar coater, an antireflection film was prepared on the PET film.

A surface at the reverse side of the antireflection film side of the film was roughened using steel wool, and a black ink was applied to measure reflection spectrum from a mirror surface, at incident angle of 5° for the surface of the antireflection film side, using a UV-visible spectrometer (UV-3100, produced from Shimadzu Corp.), and a minimal value of reflectance was determined at wavelength where reflectance became minimal. Reflectance of the antireflection film obtained was 0.45% at a wavelength of 550 nm.

5. Optical Filter

On the back surface side of the antireflection film obtained, the solution 7 of a near-infrared ray absorption material was applied by an applicator, so as to give the thickness of a pressure-sensitive adhesive layer after drying of 20 μm, and dried in a hot air dryer at 100° C. for 2 minutes. By adhesion of this pressure-sensitive adhesive film onto a glass plate, an optical filter was prepared. Total light transmittance, reflectance and transmittance of near-infrared ray of the optical filter were good.

Example 11-1

5 parts of hexafluorophosphate of indolium cation represented by the formula (c) (S0728, produced from FEW CHEMICALS GmbH, hereinafter referred to as "Indolium PF6 salt") was dissolved into 95 parts of MEK, to prepare a solution 9 of a near-infrared ray absorbing dye. Then, by using resin A as a resin, 125 parts of the resin, 3.3 parts of the solution 9 of a near-infrared ray absorbing dye, 20 parts of the borate solution 1 and 48 parts of MEK were mixed, to obtain a solution A11 of a near-infrared ray absorption material, having a solid content of coating material of 21% (solid content ratio: resin/dye/borate=100/0.43/2.5).

Example 11-2

The solution A11 of a near-infrared ray absorption material was applied on an easy adhesion type PET film (COSMOSHINE A4300, produced from Toyobo Co., Ltd.) using a bar coater (No. 34), and then dried in a hot air dryer at 150° C. for 3 minutes, to obtain a near-infrared ray absorption substrate A11. The near-infrared ray absorption substrate A11 was evaluated for transmittance of near-infrared ray, total light transmittance and heat resistance, and the results are shown in Table 6. In this case, transmittance of near-infrared ray was determined at a wavelength of 835 nm.

Example 12-1

2.11 parts of sodium tetrakis(pentafluorophenyl)borate (TEPBNa, produced from Nippon Shokubai Co., Ltd.) and 0.80 part of a indolium PF6 salt were dissolved into 20 parts of tetrahydrofuran (THF) at 25° C. Subsequently, the solvent of the resultant solution was evaporated by a rotary evaporator at 40° C. A precipitate was recovered and added into 800 parts of deionized water and dispersed therein with stirring. A precipitate was recovered by filtration of resultant dispersion and dried at 80° C., to obtain a black solid.

Figure 10:
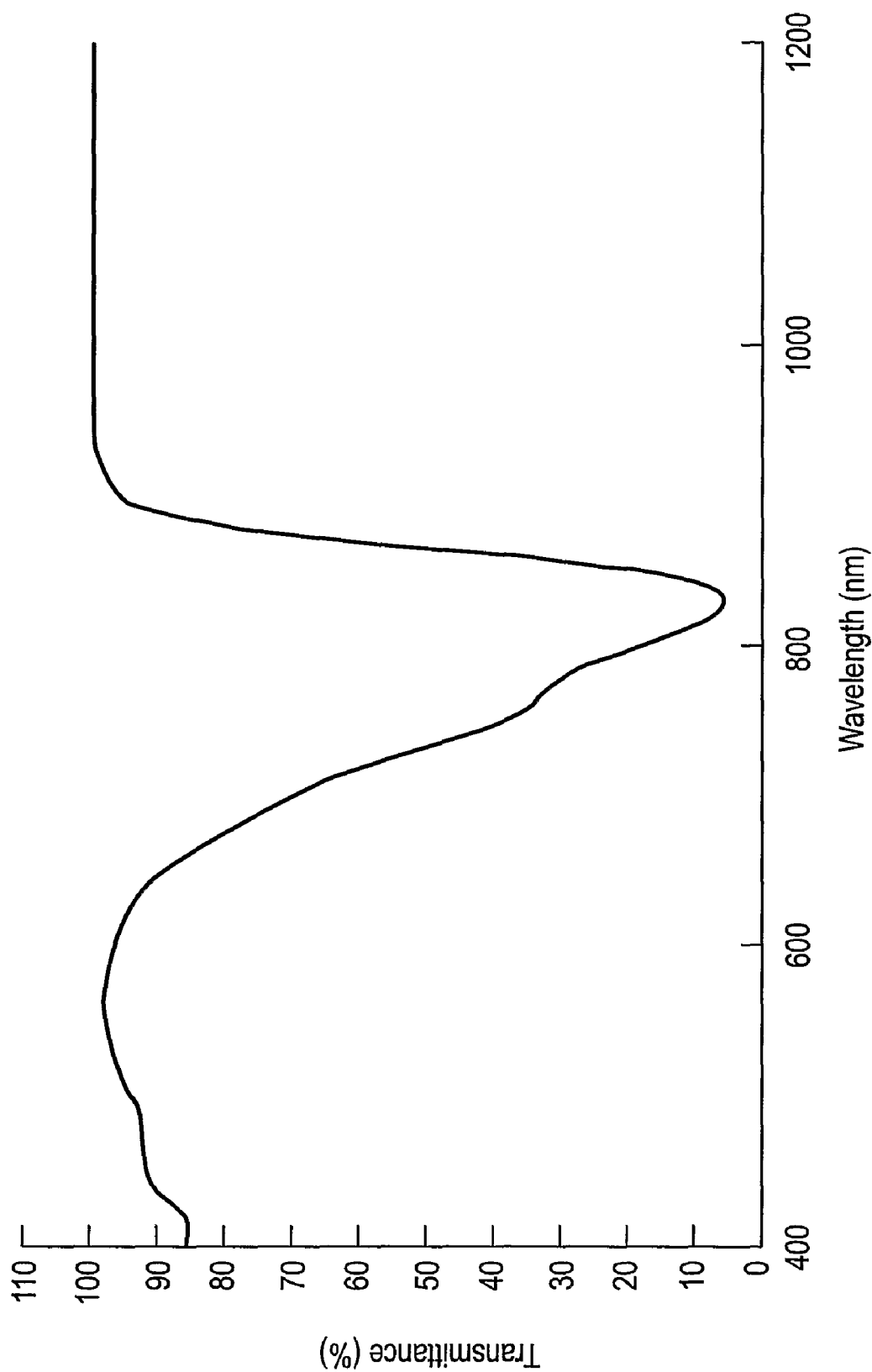
FIG. 10 is a visible-near-infrared absorbing spectrum of an indolium TEPB salt prepared in Example 12-1.
Figure 11:
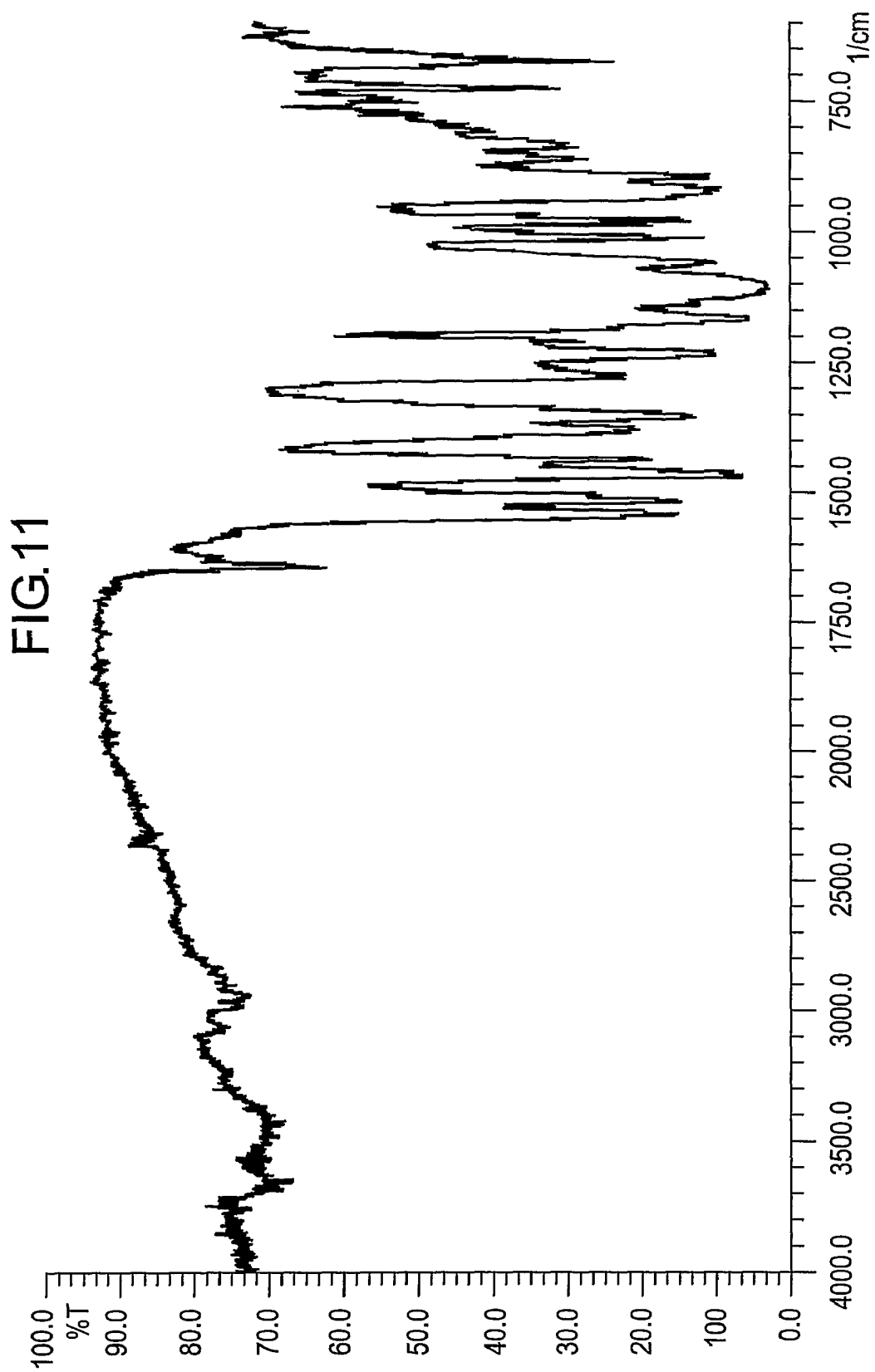
FIG. 11 is an IR spectrum of an indolium TEPB salt prepared in Example 12-1.
Figure 12:
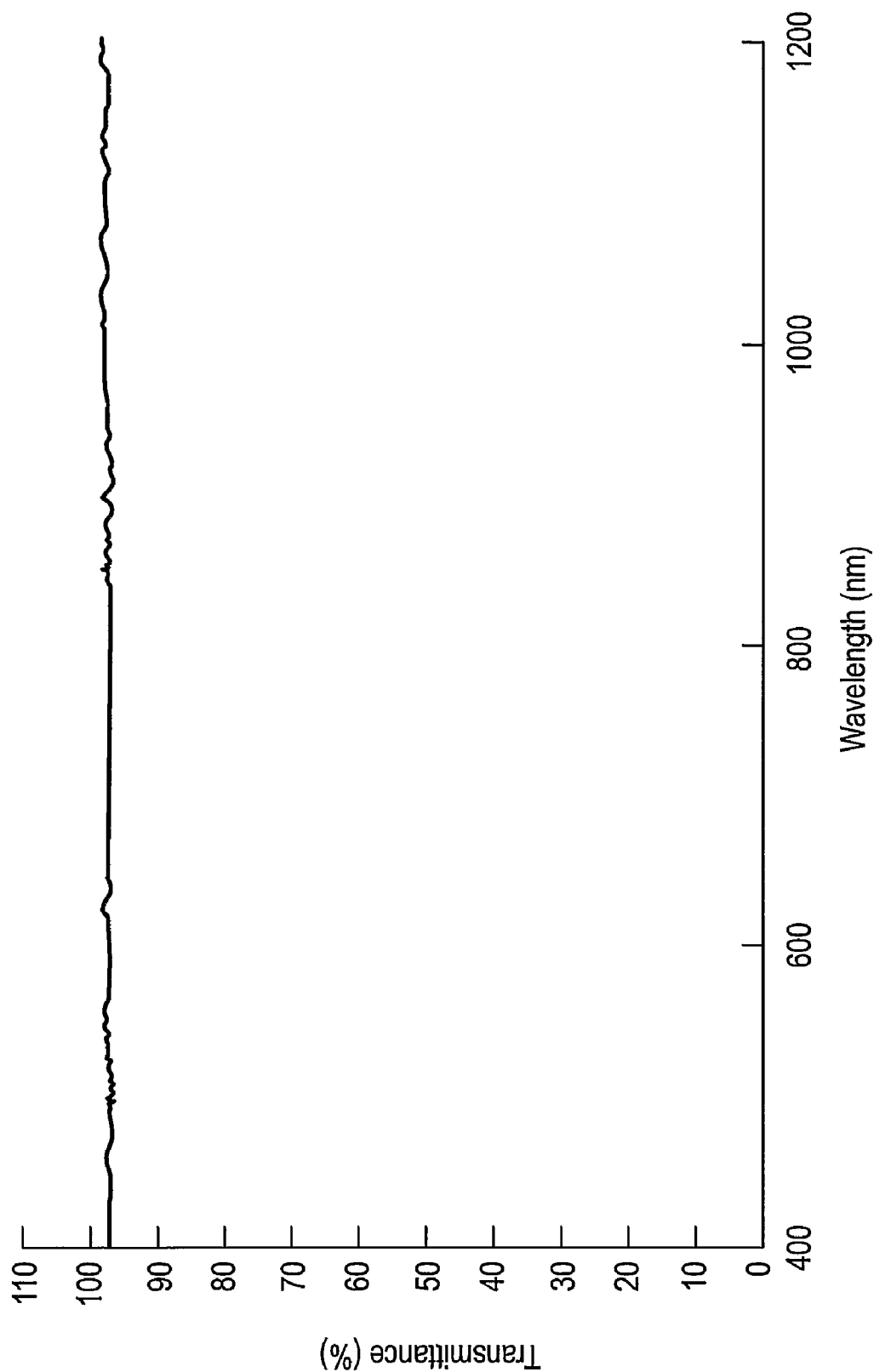
FIG. 12 is a visible-near-infrared absorbing spectrum of TEPBNa used in Example 12-1.
Figure 13:
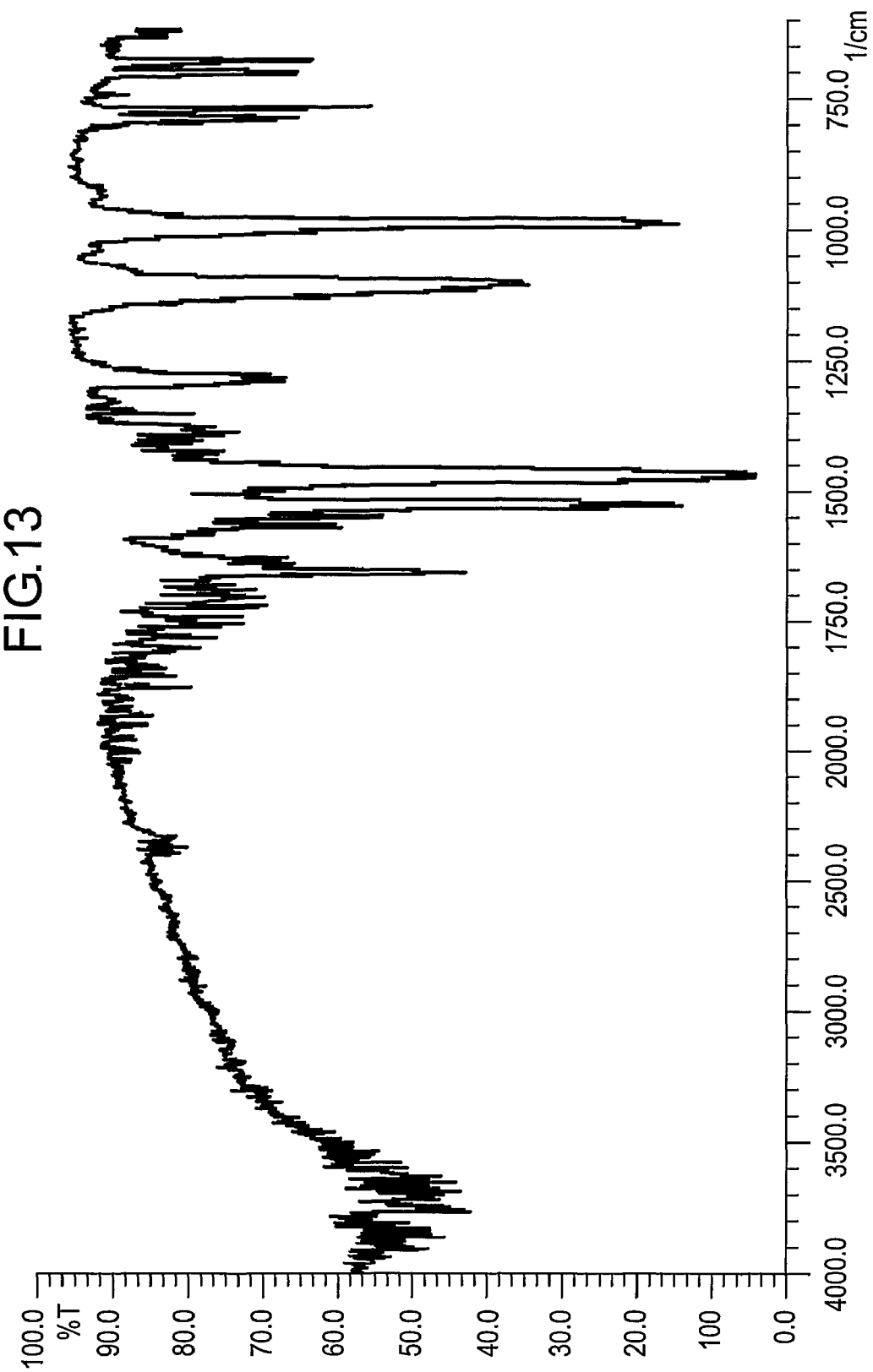
FIG. 13 is an IR spectrum of TEPBNa used in Example 12-1.
Figure 14:
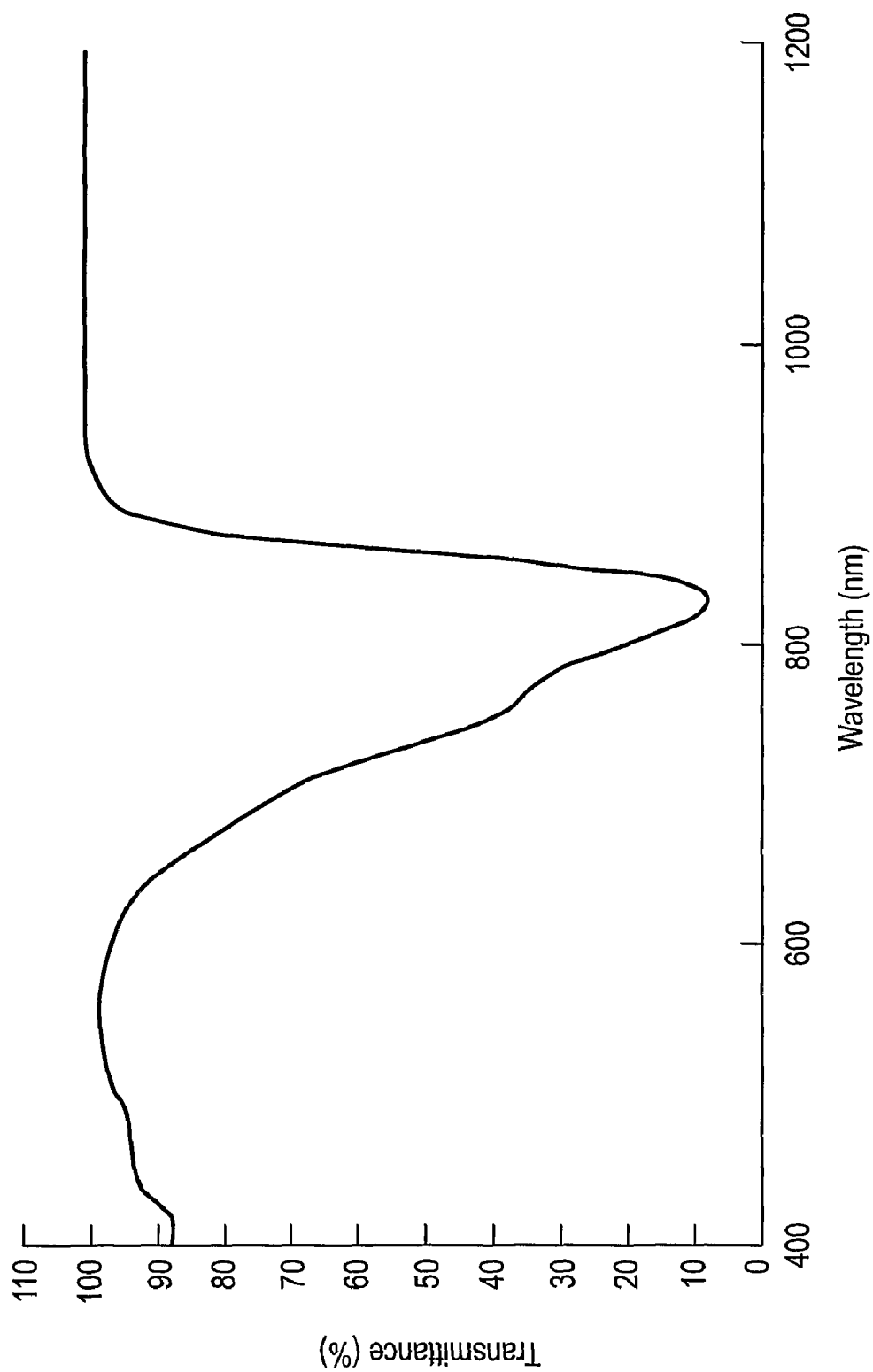
FIG. 14 is a visible-near-infrared absorbing spectrum of an indolium PF6 salt used in Example 12-1.
Figure 15:
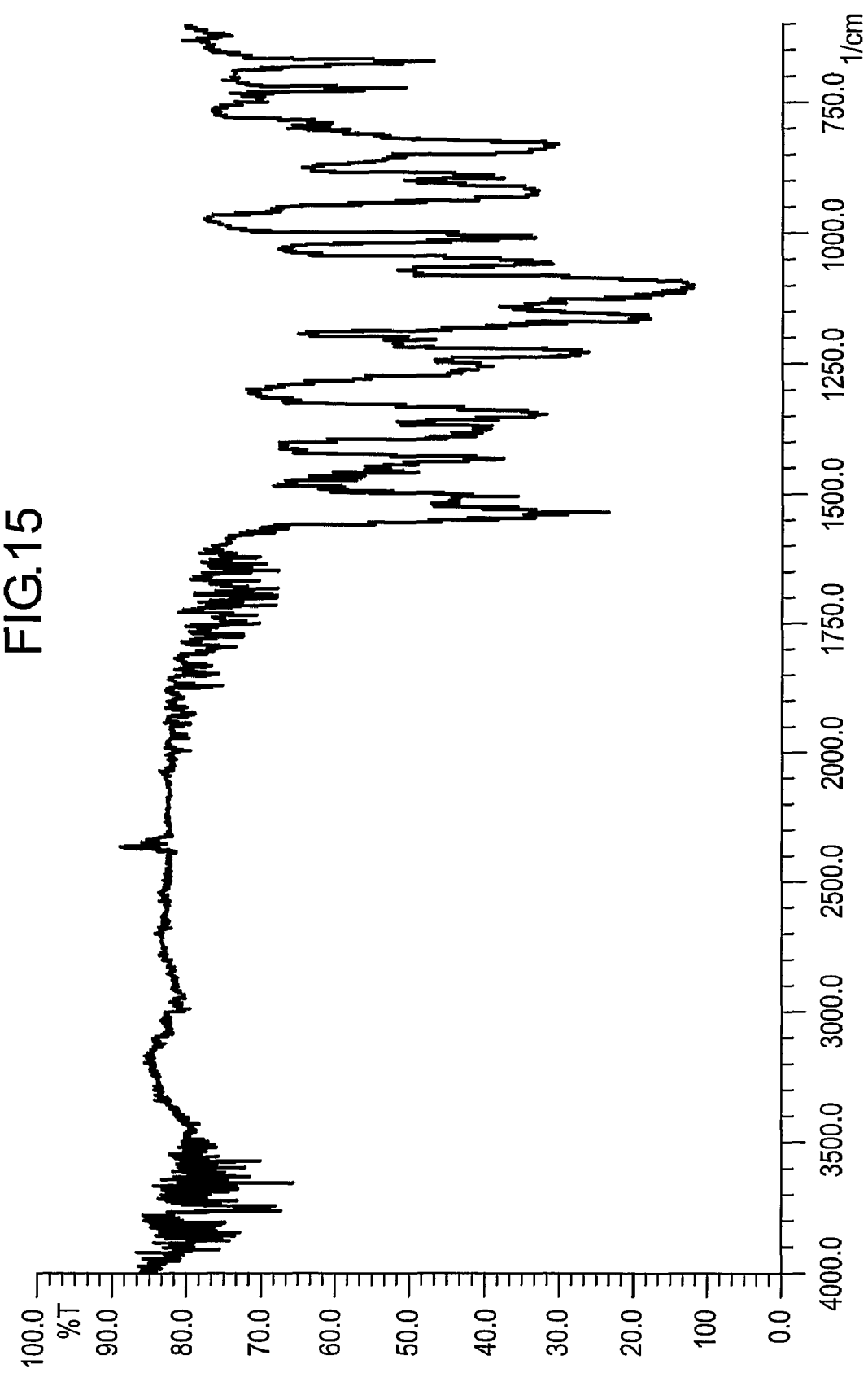
FIG. 15 is an IR spectrum of an indolium PF6 salt used in Example 12-1.

The visible-near-infrared absorbing spectrum measured by dissolving the resultant black solid in MEK was coincident with spectrum of an indolium-based dye as a raw material. In addition, the peaks peculiar to TEPB anion were detected in the IR spectrum and mass spectrum of the resultant black solid. From the above results, it was confirmed that the black solid was tetrakis(pentafluorophenyl)borate of indolium cation represented by the formula (c) (hereinafter referred to as "indolium TEPB salt"). Visible-near-infrared absorbing spectrum of the indolium TEPB salt measured by dissolving in MEK is shown in FIG. 10, and IR spectrum of the indolium TEPB salt measured by a KBr method is shown in FIG. 11. Also, visible-near-infrared absorbing spectrum of the TEPBNa measured by dissolving in MEK is shown in FIG. 12 and IR spectrum of the TEPBNa measured by a KBr method is shown in FIG. 13; and visible-near-infrared absorbing spectrum of the indolium PF6 salt measured by dissolving in MEK is shown in FIG. 14 and IR spectrum of the indolium PF6 salt measured by a KBr method is shown in FIG. 15.

Example 12-2

By dissolving 2 parts of an indolium TEPB salt into 98 parts of MEK, a solution 10 of a near-infrared ray absorbing dye was prepared. Using resin A as a resin, 63 parts of the resin, 5.5 parts of the solution 10 of a near-infrared ray absorbing dye, and 27 parts of MEK were mixed, to obtain a solution A12 of a near-infrared ray absorption material having a solid content of coating material of 21% (solid content ratio: resin/dye/borate=100/0.55/0).

Example 12-3

The solution A12 of a near-infrared ray absorption material was applied and then dried similarly as in Example 11-2, to obtain a near-infrared ray absorption substrate A12. The near-infrared ray absorption substrate A12 was evaluated for by using the same method as in Example 11-2, and the results are shown in Table 6.

Comparative Example 8-1

Using resin A as a resin, 125 parts of the resin, 3.3 parts of the solution 9 of a near-infrared ray absorbing dye, and 63 parts of MEK were mixed, to obtain a solution B8 of a near-infrared ray absorption material having a solid content of coating material of 21% (solid content ratio: resin/dye/borate=100/0.43/0).

Comparative Example 8-2

The solution B8 of a near-infrared ray absorption material was applied and then dried similarly as in Example 11-2, to obtain a near-infrared ray absorption substrate B8. The near-infrared ray absorption substrate B8 was evaluated for by using the same method as in Example 11-2, and the results are shown in Table 6.

TABLE 6

| | Resin (Solid content ratio) | Dye (Solid content ratio) | Borate (Solid content ratio) | Near-infrared ray transmittance (%) | Total light transmittance (%) | Heat resistance ΔT (%) | Heat resistance Δb* |
|---|---|---|---|---|---|---|---|
| Example 11-2 (A11) | X2 100 | Y9 0.43 | Z1 2.5 | 9.9 | 85.8 | 20.6 | 0.8 |
| Example 12-3 (A12) | X2 100 | Y10 0.55 | None — | 10.2 | 85.8 | 23.0 | −0.1 |
| Comp. Examp. 8-2 (B8) | X2 100 | Y9 0.43 | None — | 16.7 | 86.2 | 35.7 | 1.5 |

X2: Resin A
Y9: Hexafluorophosphate of indolium cation represented by the formula (c)
Y10: Tetrakis(pentafluorophenyl)borate of indolium cation represented by the formula (b)
Z1: Sodium tetrakis(pentafluorophenyl)borate It is noted from the results shown in the Table 6 that although the near-infrared ray absorption substrate A11, A12 of the present invention, comparing with the near-infrared ray absorption substrate B8 wherein no borate of the present invention was used, has equivalent total light transmittance, transmittance of near-infrared ray and change in optical characteristics at 100° C. after 120 hours are significantly smaller in the near-infrared ray absorption substrate A11, A12 of the present invention than the near-infrared ray absorption substrate B8, suggesting that the near-infrared ray absorption material of the present invention is difficult to be deteriorated.

INDUSTRIAL APPLICABILITY

Because the near-infrared ray absorption material of the present invention has high near-infrared ray absorption ability and transparency in visible region and is superior in heat resistance and moisture resistance, it is useful as an optical filter for a plasma display and an optical filter for an optical semiconductor element. It can also be used as optical information recording material.

The entire disclosure of Japanese Patent Application Nos. 2005-029504 filed on Feb. 4, 2005, 2005-137530 filed on May 10, 2005, and 2005-137561 filed on May 10, 2005 including specification, claims, drawings and summary are incorporated herein by reference in its entirety.

The invention claimed is:

1. A near-infrared ray absorption material comprising a borate which consists of a tetrakis(pentafluorophenyl) anion and a cation,
wherein the cation is a cation not having near-infrared ray absorption ability that is selected from the group consisting of: sodium, ammonium, pyridinium, anilinium, imidazolium, pyrrolidinium, quinolinium, and a combination thereof, or the cation is a cation having near-infrared ray absorption ability in the range of greater than 740 nm to 1200 nm that is selected from the group consisting of: a diimmonium cation; a cyanine dye based cation; a cation represented by the formula (2):

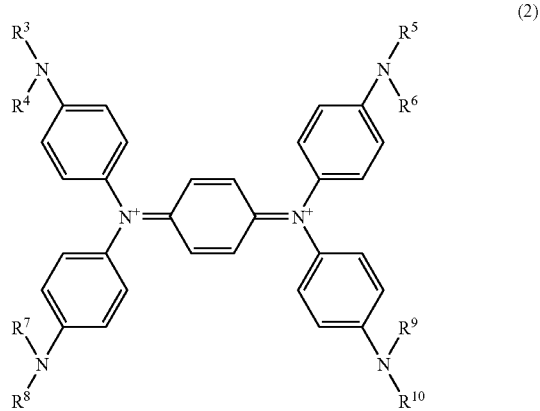

wherein $R^3$ to $R^{10}$ each independently represents a hydrogen atom, a halogen atom, an alkyl group having carbon atoms of 1 to 10, or an alkyl group having carbon atoms of 1 to 10 and having a substituent; an indolium-based cation; and a combination thereof,
with the proviso that when the cation is the cation not having near-infrared ray absorption ability, the near-infrared ray absorption material further comprises a near-infrared ray absorbing dye.

2. The near-infrared ray absorption material according to claim 1, wherein when the near-infrared ray absorption material further comprises a near-infrared ray absorbing dye, the near-infrared ray absorbing dye comprises at least one member selected from the group consisting of a diimmonium-based dye, a phthalocyanine-based dye, a cyanine-based dye, a squarylium-based dye and a metal dithiol-based dye.

3. The near-infrared ray absorption material according to claim 1, which further comprises at least one resin selected from the group consisting of a resin obtained by copolymerization of a methacrylate ester having a linear, branched, alicyclic or polycyclic alicyclic alkyl group and having carbon atoms of 1 to 10; a resin having a glass transition temperature of 65 to 85° C.; a resin having a branched structure; a pressure-sensitive adhesive and/or an adhesive; a resin having a Tg of not lower than −80° C. and not higher than 0° C. and an acid value of not higher than 30.

4. A near-infrared ray absorption substrate which comprises the near-infrared ray absorption material set forth in claim 1.

5. A near-infrared ray absorption substrate having the near-infrared ray absorption material set forth in claim 1 disposed on a transparent substrate.

6. A near-infrared ray absorption substrate according to claim 5, wherein the transparent substrate is a glass substrate, a polyethylene terephthalate film, a TAC film, an antireflection film or an electromagnetic interference shielding film.

7. An optical filter for a plasma display which uses the near-infrared ray absorption substrate set forth in claim 4.

8. An optical filter for an optical semiconductor element which uses the near-infrared ray absorption substrate set forth in claim 4.

9. A plasma display which uses the near-infrared ray absorption material set forth in claim 1, a near-infrared ray absorption substrate which comprises the near-infrared ray absorption material set forth in claim 1 or an optical filter for a plasma display which uses the near-infrared ray absorption substrate which comprises the near-infrared ray absorption material set forth in claim 1.

10. A durability enhancement agent comprising the near-infrared ray absorption material according to claim 1.

11. The near-infrared ray absorption material according to claim 1, wherein the cation has a near-infrared ray absorption ability in the range of 800 nm to 1200 nm.

12. The near-infrared ray absorption material according to claim 1, wherein a total light transmittance in visible region is not lower than 40%.

13. The near-infrared ray absorption material according to claim 1, wherein a total light transmittance in visible region is not lower than 60%.

14. The near-infrared ray absorption material according to claim 1, wherein a transmittance of near-infrared ray at a wavelength of 800 to 1000 nm is not higher than 30%.

15. The near-infrared ray absorption material according to claim 1, wherein a transmittance of near-infrared ray at a wavelength of 800 to 1000 nm is not higher than 15%.

16. The near-infrared ray absorption material according to claim 1, wherein the cation has a near-infrared ray absorption ability in the range of 900 nm to 1200 nm.

* * * * *